(12) United States Patent
Baindur et al.

(10) Patent No.: US 7,825,244 B2
(45) Date of Patent: Nov. 2, 2010

(54) INTERMEDIATES USEFUL IN THE SYNTHESIS OF ALKYLQUINOLINE AND ALKYLQUINAZOLINE KINASE MODULATORS, AND RELATED METHODS OF SYNTHESIS

(75) Inventors: Nand Baindur, Kendall Park, NJ (US); Michael David Gaul, Yardley, PA (US); Kevin Douglas Kreutter, Plainsboro, NJ (US); Guozhang Xu, Bensalem, PA (US)

(73) Assignee: Janssen Pharmaceutica NV (BE)

( * ) Notice: Subject to any disclaimer, the term of this patent is extended or adjusted under 35 U.S.C. 154(b) by 1181 days.

(21) Appl. No.: 11/422,352

(22) Filed: Jun. 6, 2006

(65) Prior Publication Data

US 2007/0021436 A1 Jan. 25, 2007

Related U.S. Application Data

(60) Provisional application No. 60/689,384, filed on Jun. 10, 2005, provisional application No. 60/730,919, filed on Oct. 27, 2005, provisional application No. 60/789,551, filed on Apr. 5, 2006.

(51) Int. Cl.
| | |
|---|---|
| C07D 239/88 | (2006.01) |
| C07D 239/94 | (2006.01) |
| C07D 215/12 | (2006.01) |
| C07D 215/14 | (2006.01) |

(52) U.S. Cl. .................. 544/283; 546/152; 546/153
(58) Field of Classification Search .......... 544/283; 546/152, 153
See application file for complete search history.

(56) References Cited

U.S. PATENT DOCUMENTS

| | | | |
|---|---|---|---|
| 3,517,005 | A | 6/1970 | Cronin et al. |
| 4,001,422 | A | 1/1977 | Danilewicz et al. |
| 4,542,132 | A | 9/1985 | Campbell et al. |
| 5,300,515 | A | 4/1994 | Takano et al. |
| 5,474,765 | A | 12/1995 | Thorpe |
| 5,762,918 | A | 6/1998 | Thorpe |
| 5,855,866 | A | 1/1999 | Thorpe et al. |
| 5,866,562 | A | 2/1999 | Schohe-Loop et al. |
| 5,948,786 | A | 9/1999 | Fujiwara et al. |
| 6,342,219 | B1 | 1/2002 | Thorpe et al. |
| 6,613,772 | B1 | 9/2003 | Schindler et al. |
| 6,776,796 | B2 | 8/2004 | Falotico et al. |
| 7,074,801 | B1 | 7/2006 | Yoshida et al. |
| 2002/0016625 | A1 | 2/2002 | Falotico et al. |
| 2004/0049032 | A1 | 3/2004 | Charrier et al. |
| 2006/0281772 | A1* | 12/2006 | Baindur et al. ......... 514/266.22 |

FOREIGN PATENT DOCUMENTS

| | | |
|---|---|---|
| EP | 08/82717 | 12/1998 |
| EP | 1 566 379 A1 | 8/2005 |
| GB | 2295387 | 5/1996 |
| JP | 59076082 | 4/1984 |
| WO | WO 96/09294 | 3/1996 |
| WO | WO 96/32907 | 10/1996 |
| WO | WO 97/28118 | 8/1997 |
| WO | WO 97/38992 | 10/1997 |
| WO | WO 99/31086 | 6/1999 |
| WO | WO 00/13681 | 3/2000 |
| WO | WO 01/32632 | 5/2001 |
| WO | WO 02/16360 A2 | 2/2002 |
| WO | WO 02/16362 | 2/2002 |
| WO | WO 02/32861 | 4/2002 |
| WO | WO 02/48152 | 6/2002 |
| WO | WO 02/069972 | 9/2002 |
| WO | WO 02/088107 | 11/2002 |
| WO | WO 02/092599 | 11/2002 |
| WO | WO 03/024931 | 3/2003 |
| WO | WO 03/024969 | 3/2003 |
| WO | WO 03/035009 | 5/2003 |
| WO | WO 03/037347 | 5/2003 |
| WO | WO 03/057690 | 7/2003 |
| WO | WO 03/064413 | 8/2003 |
| WO | WO 03/099771 | 12/2003 |
| WO | WO 2004/002960 | 1/2004 |
| WO | WO 2004/005281 | 1/2004 |
| WO | WO 2004/016597 | 2/2004 |
| WO | WO 2004/018419 | 3/2004 |
| WO | WO 2004/039782 | 5/2004 |
| WO | WO 2004/043389 | 5/2004 |
| WO | WO 2004/046120 | 6/2004 |
| WO | WO 2004/058727 | 7/2004 |
| WO | WO 2004/058749 | 7/2004 |
| WO | WO 2004/071460 | 8/2004 |
| WO | WO 2005/021500 | 3/2005 |

(Continued)

OTHER PUBLICATIONS

Baran, P. et. al., "Total synthesis of marine natural products without using protecting groups". Nature, vol. 446, Mar. 22, 2007, pp. 404-408.*

(Continued)

*Primary Examiner*—James O Wilson
*Assistant Examiner*—Tamthom N Truong

(57) ABSTRACT

The invention is directed to alkylquinoline and alkylquinazoline compounds of Formula C:

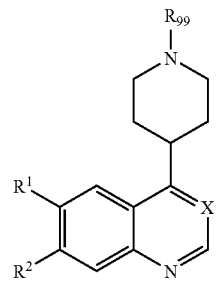

wherein $R_1$, $R_2$, $R_{99}$, and X are as defined herein, the use of such compounds in the synthesis of protein tyrosine kinase inhibitors, particularly inhibitors of FLT3 and/or c-kit and/or TrkB.

12 Claims, No Drawings

FOREIGN PATENT DOCUMENTS

| | | |
|---|---|---|
| WO | WO 2005/037825 | 4/2005 |
| WO | WO 2005/051304 | 6/2005 |
| WO | WO 2006/135646 A1 | 12/2006 |
| WO | WO 2006/135721 A1 | 12/2006 |

OTHER PUBLICATIONS

Nomoto et al., Chemical & Pharmaceutical Bulletin (1990), 38(11), 3014-19.

Ivan, Marius G. et al. Photochemistry and Photobiology (2003), 78(4), 416-419.

Sadykov, T. et al. Khimiya Geterotsiklicheskikh Soedinenii (1985), (4), 563.

Erzhanov, K. B. et al. Zhurnal Organicheskoi Khimii (1989), 25(8), 1729-32.

Fujiwara, Norio et al. Bioorganic & Medicinal Chemistry Letters (2000), 10(12), pp. 1317-1320.

Takai, Haruki et al. Chemical & Pharmaceutical Bulletin (1986), 34(5), 1907-16.

Liotta et al., Nature, Aug. 26, 2004; 430(7003), pp. 973-974.

Jaboin et al., Cancer Lett. Apr. 10, 2003;193(1), pp. 109-114.

Ashman, L., Int J Biochem Cell Biol. (1999);31(10), pp. 1037-1051.

Sattler et al., Leuk Res. (2004), 28 Suppl 1, pp. S11-20.

Advani, A., Curr Hematol Rep. (2005), 4(1), pp. 51-58.

McKenna, Hilary J. et al. Mice lacking flt3 ligand have deficient hematopoiesis affecting hematopoietic progenitor cells, dendritic cells, and natural killer cells. Blood. Jun. 2000; 95(11), pp. 3489-3497.

Drexler, H. G. and H. Quentmeier (2004), "FLT3: receptor and ligand", Growth Factors, (2004) 22(2), pp. 71-73.

Stirewalt, D. L. and J. P. Radich,(2003), "The role of FLT3 in haematopoietic malignancies", Nat Rev Cancer, (2003), 3(9): 650-65.

Scheijen, B. and J. D. Griffin, (2002), "Tyrosine kinase oncogenes in normal hematopoiesis and hematological disease", Oncogene, (2002), 21(21), pp. 3314-3333.

Kottaridis, P. D., R. E. Gale, et al. (2003), "Flt3 mutations and leukaemia", Br J Haematol (2003), 122(4), pp. 523-538.

Ansari Lari, Ali et al., FLT3 mutations in myeloid sarcoma, British Journal of Haematology. Sep. 2004 126(6), pp. 785-791.

Gilliliand et al., Blood, (2002), vol. 100, pp. 1532-1542.

Levis, M., K. F. Tse, et al., 2001, "A FLT3 tyrosine kinase inhibitor is selectively cytotoxic to acute myeloid leukemia blasts harboring FLT3 internal tandem duplication mutations." Blood (2001), 98(3), pp. 885-887.

Tse KF, et al. Inhibition of FLT3 mediated transformation by use of a tyrosine kinase inhibitor. Leukemia. Jul. 2001; 15(7), pp. 1001-1010.

Smith, B. Douglas et al., Single agent CEP 701, a novel FLT3 inhibitor, shows biologic and clinical activity in patients with relapsed or refractory acute myeloid leukemia, Blood, May 2004; 103(10), pp. 3669-3676.

Griswold, Ian J. et al. Effects of MLN518, A Dual FLT3 and KIT Inhibitor, on Normal and Malignant Hematopoiesis. Blood, Jul. 2004, 104: 2912-2918.

Yee, Kevin W. H. et al., SU5416 and SU5614 inhibit kinase activity of wild type and mutant FLT3 receptor tyrosine kinase, Blood, Sep. 2002; 100(8), pp. 2941-2949.

O'Farrell, Anne Marie et al., SU11248 is a novel FLT3 tyrosine kinase inhibitor with potent activity in vitro and in vivo, Blood, May (2003); 101(9), pp. 3597-3605.

Stone, R.M. et al., PKC 412 FLT3 inhibitor therapy in AML: results of a phase II trial, Ann Hematol. (2004); 83 Suppl 1, pp. S89-90.

Murata, K. et al., Selective cytotoxic mechanism of GTP 14564, a novel tyrosine kinase inhibitor in leukemia cells expressing a constitutively active Fms like tyrosine kinase 3 (FLT3), J Biol Chem. Aug. 29, 2003; 278(35), pp. 32892-32898.

Levis, Mark et al., Novel FLT3 tyrosine kinase inhibitors, Expert Opin. Investing. Drugs (2003) 12(12), pp. 1951-1962.

Levis, Mark et al., Small Molecule FLT3 Tyrosine Kinase Inhibitors, Current Pharmaceutical Design, (2004), 10, pp. 1183-1193.

Gould, P., International J. Pharm. (1986), 33, pp. 201-217.

Berge et al., J. Pharm. Sci., Jan. 1977, 66(1), pp. 1-19.

Boothroyd et al., Tet Lett (1995), 36(14), pp. 2411-2414.

Sitzmann et al., J. Org Chem, (1985), 50, pp. 5879-5881.

Tyrrell et al., Synthesis, (2004), 4, pp. 469-483.

Kristensen et al., Organic Letters, (2001), 3(10), pp. 1435-1437.

Stevenson et al., J. Org. Chem., (1986), 51, pp. 616-620.

Hall et al., Inorganic Chemistry (1997), 36(14), pp. 3096-3101.

Bertani et al., Organometallics, (1996), 15(4), pp. 1236-1241.

Quentmeier H, Reinhardt J, Zaborski M, Drexler HG, FLT3 mutations in acute myeloid leukemia cell lines, Leukemia, (2003), 17, pp. 120-124.

Sadick, MD et al., Analysis of Heregulin-Induced ErbB2 Phosphorylation with a High-Throughput Kinase Receptor Activation Enzyme-Linked Immunsorbent Assay, Analytical Biochemistry, (1996), 235, pp. 207-214.

Baumann CA et al., Development of a quantitative, high-throughput cell-based enzyme-linked immunosorbent assay for detection of colony-stimulating factor-1 receptor tyrosine kinase inhibitors, J Biochem Biophys Methods, (2004), 60, pp. 69-79.

Libby P, "Vascular biology of atherosclerosis: overview and state of the art", Am J Cardiol (2003), 91(3A), pp. 3A-6A.

Helisch A, Schaper W., Arteriogenesis: the development and growth of collateral arteries. Microcirculation, (2003),10(1), pp. 83-97.

Holz FG et al.,"Pathogenesis of lesions in late age-related macular disease", Am J Ophthalmol. (2004), 137(3), pp. 504-510.

Schiele TM et. al.,"Vascular restenosis—striving for therapy." Expert Opin Pharmacother. (2004), 5(11), pp. 2221-2232.

Thannickal VJ et al., Idiopathic pulmonary fibrosis: emerging concepts on pharmacotherapy, Expert Opin Pharmacother. (2004), 5(8), pp. 1671-1686.

Cybulsky AV, "Growth factor pathways in proliferative glomerulonephritis", Curr Opin Nephrol Hypertens (2000), 9(3), pp. 217-223.

Harris RC et al, "Molecular basis of injury and progression in focal glomerulosclerosis" Nephron (1999), 82(4), pp. 289-299.

Woolf AS et al., "Evolving concepts in human renal dysplasia", J Am Soc Nephrol. (2004), 15(4), pp. 998-1007.

Grant MB et al.,"The role of growth factors in the pathogenesis of diabetic retinopathy", Expert Opin Investig Drugs (2004), 13(10), pp. 1275-1293.

Sweeney SE, Firestein GS, Rheumatoid arthritis: regulation of synovial inflammation, Int J Biochem Cell Biol. (2004), 36(3), pp. 372-378.

Brodeur GM, "Neuroblastoma: biological insights into a clinical enigma." Nat RevCancer; (2003), 3(3), pp. 203-216.

Eggert A et. al. "Expression of the neurotrophin receptor TrkB is associated with unfavorable outcome in Wilms' tumor" J Clin Oncol. (2001), 19(3), pp. 689-696.

Descamps S et.al., "Nerve growth factor stimulates proliferation and survival of human breast cancer cells through two distinct signaling pathways." J Biol Chem. (2001), 276(21), pp. 17864-17870.

Bardelli A, et. al., "Mutational analysis of the tyrosine kinome in colorectal cancers." Science (2003), 300, p. 949.

Weeraratna AT et. al., "Rational basis for Trk inhibition therapy for prostate cancer." The Prostate (2000), 45(2), pp. 140-148.

Ricci et. al., "Neurotrophins and neurotrophin receptors in human lung cancer." Am J Respir Cell Mol Biol. (2001), 25(4), pp. 439-446.

Simpson WG, The calcium channel blocker verapamil and cancer chemotherapy. Cell Calcium. (1985), 6(6), pp. 449-467.

Schiele TM et. al., "Vascular restenosis—striving for therapy." Expert Opin Pharmacother. (2004), 5(11), pp. 2221-2232.

Ricci A, et. al., "Neurotrophins and neurotrophin receptors in human pulmonary arteries." J Vasc Res. (2000), 37(5), pp. 355-363.

Kim H, et. al., "Paracrine and autocrine functions of brain-derived neurotrophic factor (BDNF) and nerve growth factor (NGF) in brain-derived endothelial cells", J Biol Chem. (2004), 279(32), pp. 33538-33546.

Douma S, et. al., "Suppression of anoikis and induction of metastasis by the neurotrophic receptor TrkB", Nature. (2004), 430(7003), pp. 1034-1040.

Arnon et al., "Monoclonal Antibodies for Immunotargeting of Drugs In Cancer Therapy", in Monoclonal Antibodies and Cancer Therapy, Reisfeld et al. (eds.), pp. 243-256 (Alan R. Liss, Inc. 1985).

Hellstrom et al., "Antibodies for Drug Delivery", in Controlled Drug Delivery (2nd Ed.), Robinson et al. (eds.), pp. 623-653 (Marcel Dekker, Inc. 1987).

Thorpe, "Antibody Carriers of Cytotoxic Agents In Cancer Therapy: A Review", in Monoclonal Antibodies '84: Biological And Clinical Applications, Pinchera et al. (eds.), pp. 475-506 (1985).

Heinrich, Michael C. et al. Review Article: Inhibition of KIT Tyrosine Kinase Activity: A Novel Molecular Approach to the Treatment of KIT- Positive Malignancies, Journal of Clin. Oncology, vol. 20, No. 6; 1692-1703 (2002).

International Search Report re: PCT/US2006/022171 dated Oct. 16, 2006.

International Search Report re: PCT/US2006/022414 dated Oct. 24, 2006.

* cited by examiner

INTERMEDIATES USEFUL IN THE SYNTHESIS OF ALKYLQUINOLINE AND ALKYLQUINAZOLINE KINASE MODULATORS, AND RELATED METHODS OF SYNTHESIS

CROSS REFERENCE TO RELATED APPLICATIONS

This application claims priority to U.S. Provisional Application for Patent No. 60/689,384, filed Jun. 10, 2005, U.S. Provisional Application for Patent No. 60/730,919, filed Oct. 27, 2005, and U.S. Provisional Application for Patent No. 60/789,551, filed Apr. 5, 2006, the entire disclosures of which are hereby incorporated in their entirely.

FIELD OF THE INVENTION

The invention relates to intermediates useful in the synthesis of novel compounds that function as protein tyrosine kinase modulators, specifically inhibitors of FLT3, c-kit and TrkB, and related methods of synthesis thereof.

BACKGROUND OF THE INVENTION

The present invention relates to intermediates useful in the synthesis of quinolines and quinazolines useful as inhibitors of tyrosine kinases, including FLT3, c-kit and TrkB. Quinazolines have been reported with useful therapeutic properties: U.S. Pat. No. 4,001,422 (DE 2530894) and U.S. Pat. No. 4,542,132 (EP 135318) describe quinazolines as cardiac stimulants, and U.S. Pat. No. 3,517,005 discloses quinazolines with hypotensive and bronchodilation activity. Cardiotonic quinazolines have also been reported, see Chemical & Pharmaceutical Bulletin (1990), 38(11), 3014-19. Quinolines have been reported to possess utility for the inhibition of autophosphorylation of FLT3, see PCT International Application WO2004039782, and for the treatment of amnesia and stroke, as well as a variety of other conditions, see U.S. Pat. No. 5,300,515 (EP 497303) and U.S. Pat. No. 5,866,562; and PCT International Applications WO2004/002960 and WO2002/088107. Also of note are WO2004058727 (substituted 3,5-dihydro-4H-imidazol-4-ones for the treatment of obesity); WO 2000013681 (4-quinolinemethanol derivatives as purine receptor antagonists); DE 19756388 (U.S. Pat. No. 6,613,772) (substituted 2-aryl-4-amino-quinazolines); JP 59076082 (piperidine derivatives); WO 1999031086 (quinolinepiperazine and quinolinepiperidine derivatives and their use as combined 5-HT1A, 5-HT1B, and 5-HT1D receptor antagonists); U.S. Pat. No. 5,948,786 (piperidinylpyrimidines tumor necrosis factor inhibitors); WO 1997038992 (piperidinylpyrimidine derivatives useful as inhibitors of tumor necrosis factor); Ivan, Marius G. et al. Photochemistry and Photobiology (2003), 78(4), 416-419; Sadykov, T. et al. Khimiya Geterotsiklicheskikh Soedinenii (1985), (4), 563; Erzhanov, K. B. et al. Zhurnal Organicheskoi Khimii (1989), 25(8), 1729-32; Fujiwara, Norio et al. Bioorganic & Medicinal Chemistry Letters (2000), 10(12), 1317-1320; Takai, Haruki et al. Chemical & Pharmaceutical Bulletin (1986), 34(5), 1907-16; WO 2002069972 ((triazolylpiperazinyl)isoquinolines for treatment of neurodegenerative diseases, brain injury and cerebral ischemia); and GB 2295387 (quinazoline derivatives as adrenergic 1C receptor antagonists).

Protein kinases are enzymatic components of the signal transduction pathways which catalyze the transfer of the terminal phosphate from ATP to the hydroxy group of tyrosine, serine and/or threonine residues of proteins. Thus, compounds which inhibit protein kinase functions are valuable tools for assessing the physiological consequences of protein kinase activation. The overexpression or inappropriate expression of normal or mutant protein kinases in mammals has been a topic of extensive study and has been demonstrated to play a significant role in the development of many diseases, including diabetes, angiogenesis, psoriasis, restenosis, ocular diseases, schizophrenia, rheumatoid arthritis, atherosclerosis, cardiovascular disease and cancer. The cardiotonic benefits of kinase inhibition has also been studied. In sum, inhibitors of protein kinases have particular utility in the treatment of human and animal disease.

The Trk family receptor tyrosine kinases, TrkA, TrkB, and TrkC, are the signaling receptors that mediate the biological actions of the peptide hormones of the neurotrophin family. This family of growth factors includes nerve growth factor (NGF), brain-derived neurotrophic factor (BDNF), and two neurotrophins (NT), NT-3, and NT-4. TrkB serves as a receptor for both BDNF and NT-4. BDNF promotes the proliferation, differentiation and survival of normal neural components such as retinal cells and glial cells.

It has recently been reported (see, Nature 26 Aug. 2004; 430(7003):973-4; 1034-40) that TrkB activation is a potent and specific suppressor of anchorage independent cell death (anoikis). Anchorage independent cell survival allows tumor cells to migrate through the systemic circulation and grow at distant organs. This metastatic process is often responsible for the failure of cancer treatment and the cause of mortality in cancer. Other studies (see, Cancer Lett. 10 Apr. 2003;193 (1):109-14) have also suggested that BDNF agonism of TrkB is capable of blocking cisplatin induced cell death. Taken together, these results suggest that TrkB modulation is an attractive target for treatment of benign and malignant proliferative diseases, especially tumor diseases.

The receptor tyrosine kinase c-kit and its ligand Stem Cell Factor (SCF) are essential for hemoatpoiesis, melanogenesis and fertility. SCF acts at multiple levels of the hemoatpoietic hierarchy to promote cell survival, proliferation, differentiation, adhesion and functional activation. It is of particular importance in the mast cell and erythroid lineages, but also acts on multipotential stem and progenitor cells, megakaryocytes, and a subset of lymphoid progenitors (see, *Int J Biochem Cell Biol.* 1999 October;31(10):1037-51). Sporadic mutations of c-kit as well as autocrine/paracrine activation mechanisms of the SCF/c-kit pathway have been implicated in a variety of malignancies. Activation of c-kit contributes to metastases by enhancing tumor growth and reducing apoptosis. Additionally, c-kit is frequently mutated and activated in gastrointestinal stromal tumors (GISTs), and ligand-mediated activation of c-kit is present in some lung cancers (see, Leuk Res. 2004 May;28 Suppl 1:S11-20). The c-kit receptor also is expressed on more than 10% of blasts in 64% of de novo acute myelogenous leukemias (AMLs) and 95% of relapsed AMLs. C-kit mediates proliferation and anti-apoptotic effects in AML (see, *Curr Hematol Rep.* 2005 January; 4(1):51-8).

C-Kit expression has been documented in a wide variety of human malignancies, including mastocytosis, mast cell leukemia, gastrointestinal stromal tumour, sinonasal natural killer/T-cell lymphoma, seminoma, dysgerminoma, thyroid carcinoma; small-cell lung carcinoma, malignant melanoma, adenoid cystic carcinoma, ovarian carcinoma, acute myelogenous leukemia, anaplastic large cell lymphoma, angiosarcoma, endometrial carcinoma, pediatric T-cell ALL, lymphoma, breast carcinoma and prostate carcinoma. See, Heinrich, Michael C. et al. Review Article: Inhibition of KIT Tyrosine Kinase Activity: A Novel Molecular Approach to the Treatment of KIT-Positive Malignancies.

The fms-like tyrosine kinase 3 (FLT3) ligand (FLT3L) is one of the cytokines that affects the development of multiple hematopoietic lineages. These effects occur through the binding of FLT3L to the FLT3 receptor, also referred to as fetal liver kinase-2 (flk-2) and STK-1, a receptor tyrosine kinase (RTK) expressed on hematopoietic stem and progenitor cells. The FLT3 gene encodes a membrane-bound RTK that plays an important role in proliferation, differentiation and apoptosis of cells during normal hematopoiesis. The FLT3 gene is mainly expressed by early meyloid and lymphoid progenitor cells. See McKenna, Hilary J. et al. Mice lacking FLT3 ligand have deficient hematopoiesis affecting hematopoietic progenitor cells, dendritic cells, and natural killer cells. Blood. June 2000; 95: 3489-3497; Drexler, H. G. and H. Quentmeier (2004). "FLT3: receptor and ligand." Growth Factors 22(2): 71-3.

The ligand for FLT3 is expressed by the marrow stromal cells and other cells and synergizes with other growth factors to stimulate proliferation of stem cells, progenitor cells, dendritic cells, and natural killer cells.

Hematopoietic disorders are pre-malignant disorders of these systems and include, for instance, the myeloproliferative disorders, such as thrombocythemia, essential thrombocytosis (ET), angiogenic myeloid metaplasia, myelofibrosis (MF), myelofibrosis with myeloid metaplasia (MMM), chronic idiopathic myelofibrosis (IMF), and polycythemia vera (PV), the cytopenias, and pre-malignant myelodysplastic syndromes. See Stirewalt, D. L. and J. P. Radich (2003). "The role of FLT3 in haematopoietic malignancies." Nat Rev Cancer 3(9): 650-65; Scheijen, B. and J. D. Griffin (2002). "Tyrosine kinase oncogenes in normal hematopoiesis and hematological disease." Oncogene 21(21): 3314-33.

Hematological malignancies are cancers of the body's blood forming and immune systems, the bone marrow and lymphatic tissues. Whereas in normal bone marrow, FLT3 expression is restricted to early progenitor cells, in hematological malignancies, FLT3 is expressed at high levels or FLT3 mutations cause an uncontrolled induction of the FLT3 receptor and downstream molecular pathway, possibly Ras activation. Hematological malignancies include leukemias, lymphomas (non-Hodgkin's lymphoma), Hodgkin's disease (also called Hodgkin's lymphoma), and myeloma—for instance, acute lymphocytic leukemia (ALL), acute myeloid leukemia (AML), acute promyelocytic leukemia (APL), chronic lymphocytic leukemia (CLL), chronic myeloid leukemia (CML), chronic neutrophilic leukemia (CNL), acute undifferentiated leukemia (AUL), anaplastic large-cell lymphoma (ALCL), prolymphocytic leukemia (PML), juvenile myelomonocyctic leukemia (JMML), adult T-cell ALL, AML with trilineage myelodysplasia (AML/TMDS), mixed lineage leukemia (MLL), myelodysplastic syndromes (MDSs), myeloproliferative disorders (MPD), multiple myeloma, (MM) and myeloid sarcoma. See Kottaridis, P. D., R. E. Gale, et al. (2003). "Flt3 mutations and leukaemia." Br J Haematol 122(4): 523-38. Myeloid sarcoma is also associated with FLT3 mutations. See Ansari-Lari, Ali et al. FLT3 mutations in myeloid sarcoma. British Journal of Haematology. 2004 September 126(6):785-91.

Mutations of FLT3 have been detected in about 30% of patients with acute myelogenous leukemia and a small number of patients with acute lymphomatic leukemia or myelodysplastic syndrome. Patients with FLT3 mutations tend to have a poor prognosis, with decreased remission times and disease free survival. There are two known types of activating mutations of FLT3. One is a duplication of 4-40 amino acids in the juxtamembrane region (ITD mutation) of the receptor (25-30% of patients) and the other is a point mutation in the kinase domain (5-7% of patients). The mutations most often involve small tandem duplications of amino acids within the juxtamembrane domain of the receptor and result in tyrosine kinase activity. Expression of a mutant FLT3 receptor in murine marrow cells results in a lethal myeloproliferative syndrome, and preliminary studies (Blood. 2002; 100: 1532-42) suggest that mutant FLT3 cooperates with other leukemia oncogenes to confer a more aggressive phenotype.

Taken together, these results suggest that specific inhibitors of the individual kinases FLT3, and/or TrkB and/or c-kit, present an attractive target for the treatment of hematopoietic disorders and hematological malignancies. Accordingly, there exists a need for intermediates useful in the synthesis of such inhibitors, and methods of synthesis thereof.

FLT3 kinase inhibitors known in the art include AG1295 and AG1296; Lestaurtinib (also known as CEP 701, formerly KT-5555, Kyowa Hakko, licensed to Cephalon); CEP-5214 and CEP-7055 (Cephalon); CHIR-258 (Chiron Corp.); EB-10 and IMC-EB10 (ImClone Systems Inc.); GTP 14564 (Merk Biosciences UK). Midostaurin (also known as PKC 412 Novartis AG); MLN 608 (Millennium USA); MLN-518 (formerly CT53518, COR Therapeutics Inc., licensed to Millennium Pharmaceuticals Inc.); MLN-608 (Millennium Pharmaceuticals Inc.); SU-11248 (Pfizer USA); SU-11657 (Pfizer USA); SU-5416 and SU 5614; THRX-165724 (Theravance Inc.); AMI-10706 (Theravance Inc.); VX-528 and VX-680 (Vertex Pharmaceuticals USA, licensed to Novartis (Switzerland), Merck & Co USA); and XL 999 (Exelixis USA). The following PCT International Applications and US Patent Applications disclose additional kinase modulators, including modulators of FLT3: WO 2002032861, WO 2002092599, WO 2003035009, WO 2003024931, WO 2003037347, WO 2003057690, WO 2003099771, WO 2004005281, WO 2004016597, WO 2004018419, WO 2004039782, WO 2004043389, WO 2004046120, WO 2004058749, WO 2004058749, WO 2003024969 and U.S. patent application Ser. No. 20040049032.

See also Levis, M., K. F. Tse, et al. 2001 "A FLT3 tyrosine kinase inhibitor is selectively cytotoxic to acute myeloid leukemia blasts harboring FLT3 internal tandem duplication mutations." Blood 98(3): 885-7; Tse KF, et al. Inhibition of FLT3-mediated transformation by use of a tyrosine kinase inhibitor. Leukemia. 2001 July;15(7):1001-10; Smith, B. Douglas et al. Single-agent CEP-701, a novel FLT3 inhibitor, shows biologic and clinical activity in patients with relapsed or refractory acute myeloid leukemia Blood, May 2004; 103: 3669 -3676; Griswold, Ian J. et al. Effects of MLN518, A Dual FLT3 and KIT Inhibitor, on Normal and Malignant Hematopoiesis. Blood, July 2004; [Epub ahead of print]; Yee, Kevin W. H. et al. SU5416 and SU5614 inhibit kinase activity of wild-type and mutant FLT3 receptor tyrosine kinase. Blood, September 2002; 100: 2941 -294; O'Farrell, Anne-Marie et al. SU11248 is a novel FLT3 tyrosine kinase inhibitor with potent activity in vitro and in vivo. Blood, May 2003; 101: 3597 -3605; Stone, R. M. et al. PKC 412 FLT3 inhibitor therapy in AML: results of a phase II trial. Ann Hematol. 2004; 83 Suppl 1:S89-90; and Murata, K. et al. Selective cytotoxic mechanism of GTP-14564, a novel tyrosine kinase inhibitor in leukemia cells expressing a constitutively active Fms-like tyrosine kinase 3 (FLT3). J Biol Chem. 2003 Aug. 29; 278(35): 32892-8; Levis, Mark et al. Novel FLT3 tyrosine kinase inhibitors. Expert Opin. Investing. Drugs (2003) 12(12) 1951-1962; Levis, Mark et al. Small Molecule FLT3 Tyrosine Kinase Inhibitors. Current Pharmaceutical Design, 2004, 10, 1183-1193.

SUMMARY OF THE INVENTION

The present invention provides novel intermediates of Formula C useful in the synthesis of novel quinolines and quinazolines (the compounds of Formula I) as inhibitors of FLT3 and/or c-kit and/or TrkB, and methods of synthesis thereof.

Other features and advantages of the invention will be apparent from the following Detailed Description of the Invention and from the Claims.

DETAILED DESCRIPTION OF THE INVENTION

The present invention provides novel intermediates of Formula C useful in the synthesis of novel quinolines and quinazolines (the compounds of Formula I), which are inhibitors of FLT3 and/or c-kit and/or TrkB.

Definitions

As used herein, the following terms are intended to have the following meanings (additional definitions are provided where needed throughout the Specification):

The term "alkenyl," whether used alone or as part of a substituent group, for example, "$C_{1-4}$alkenyl(aryl)," refers to a partially unsaturated branched or straight chain monovalent hydrocarbon radical having at least one carbon—carbon double bond, whereby the double bond is derived by the removal of one hydrogen atom from each of two adjacent carbon atoms of a parent alkyl molecule and the radical is derived by the removal of one hydrogen atom from a single carbon atom. Atoms may be oriented about the double bond in either the cis (Z) or trans (E) conformation. Typical alkenyl radicals include, but are not limited to, ethenyl, propenyl, allyl (2-propenyl), butenyl and the like. Examples include $C_{2-8}$alkenyl or $C_{2-4}$alkenyl groups.

The term "$C_{a-b}$" (where a and b are integers referring to a designated number of carbon atoms) refers to an alkyl, alkenyl, alkynyl, alkoxy or cycloalkyl radical or to the alkyl portion of a radical in which alkyl appears as the prefix root containing from a to b carbon atoms inclusive. For example, $C_{1-4}$ denotes a radical containing 1, 2, 3 or 4 carbon atoms.

The term "alkyl," whether used alone or as part of a substituent group, refers to a saturated branched or straight chain monovalent hydrocarbon radical, wherein the radical is derived by the removal of one hydrogen atom from a single carbon atom. Unless specifically indicated (e.g. by the use of a limiting term such as "terminal carbon atom"), substituent variables may be placed on any carbon chain atom. Typical alkyl radicals include, but are not limited to, methyl, ethyl, propyl, isopropyl and the like. Examples include $C_{1-8}$alkyl, $C_{1-6}$alkyl and $C_{1-4}$alkyl groups.

The term "alkylamino" refers to a radical formed by the removal of one hydrogen atom from the nitrogen of an alkylamine, such as butylamine, and the term "dialkylamino" refers to a radical formed by the removal of one hydrogen atom from the nitrogen of a secondary amine, such as dibutylamine. In both cases it is expected that the point of attachment to the rest of the molecule is the nitrogen atom.

The term "alkynyl," whether used alone or as part of a substituent group, refers to a partially unsaturated branched or straight chain monovalent hydrocarbon radical having at least one carbon-carbon triple bond, whereby the triple bond is derived by the removal of two hydrogen atoms from each of two adjacent carbon atoms of a parent alkyl molecule and the radical is derived by the removal of one hydrogen atom from a single carbon atom. Typical alkynyl radicals include ethynyl, propynyl, butynyl and the like. Examples include $C_{2-8}$alkynyl or $C_{2-4}$alkynyl groups.

The term "alkoxy" refers to a saturated or partially unsaturated branched or straight chain monovalent hydrocarbon alcohol radical derived by the removal of the hydrogen atom from the hydroxide oxygen substituent on a parent alkane, alkene or alkyne. Where specific levels of saturation are intended, the nomenclature "alkoxy", "alkenyloxy" and "alkynyloxy" are used consistent with the definitions of alkyl, alkenyl and alkynyl. Examples include $C_{1-8}$alkoxy or $C_{1-4}$alkoxy groups.

The term "alkoxyether" refers to a saturated branched or straight chain monovalent hydrocarbon alcohol radical derived by the removal of the hydrogen atom from the hydroxide oxygen substituent on a hydroxyether. Examples include 1-hydroxyl-2-methoxy-ethane and 1-(2-hydroxyl-ethoxy)-2-methoxy-ethane groups.

The term "aralkyl" refers to a $C_{1-6}$ alkyl group containing an aryl substituent. Examples include benzyl, phenylethyl or 2-naphthylmethyl. It is intended that the point of attachment to the rest of the molecule be the alkyl group.

The term "aromatic" refers to a cyclic hydrocarbon ring system having an unsaturated, conjugated π electron system.

The term "aryl" refers to an aromatic cyclic hydrocarbon ring radical derived by the removal of one hydrogen atom from a single carbon atom of the ring system. Typical aryl radicals include phenyl, naphthalenyl, fluorenyl, indenyl, azulenyl, anthracenyl and the like.

The term "benzo-fused heteroaryl" refers to a bicyclic fused ring system radical wherein one of the rings is phenyl and the other is a heteroaryl ring. Typical benzo-fused heteroaryl radicals include indolyl, indolinyl, isoindolyl, benzo[b]furyl, benzo[b]thienyl, indazolyl, benzthiazolyl, quinolinyl, isoquinolinyl, cinnolinyl, phthalazinyl, quinazolinyl, and the like. A benzo-fused heteroaryl ring is a subset of the heteroaryl group.

The term "benzo-fused heterocyclyl" refers to a bicyclic fused ring system radical wherein one of the rings is phenyl and the other is a heterocyclyl ring. Typical benzo-fused heterocyclyl radicals include 1,3-benzodioxolyl (also known as 1,3-methylenedioxyphenyl), 2,3-dihydro-1,4-benzodioxinyl (also known as 1,4-ethylenedioxyphenyl),benzo-dihydro-furyl, benzo-tetrahydro-pyranyl, benzo-dihydro-thienyl and the like.

The term "cyclic heterodionyl" refers to a heterocyclic compound bearing two oxo substituents. Examples include thiazolidinedionyl, oxazolidinedionyl and pyrrolidinedionyl.

The term "cycloalkyl" refers to a saturated or partially unsaturated monocyclic or bicyclic hydrocarbon ring radical derived by the removal of one hydrogen atom from a single ring carbon atom. Typical cycloalkyl radicals include cyclopropyl, cyclobutyl, cyclopentyl, cyclopentenyl, cyclohexyl, cyclohexenyl, cycloheptyl and cyclooctyl. Additional examples include $C_{3-8}$cycloalkyl, $C_{5-8}$cycloalkyl, $C_{3-12}$cycloalkyl, $C_{3-20}$cycloalkyl, decahydronaphthalenyl, and 2,3,4,5,6,7-hexahydro-1H-indenyl.

The term "fused ring system" refers to a bicyclic molecule in which two adjacent atoms are present in each of the two cyclic moieties. Heteroatoms may optionally be present. Examples include benzothiazole, 1,3-benzodioxole and decahydronaphthalene.

The term "hetero" used as a prefix for a ring system refers to the replacement of at least one ring carbon atom with one or more atoms independently selected from N, S, O or P. Examples include rings wherein 1, 2, 3 or 4 ring members are a nitrogen atom; or, 0, 1, 2 or 3 ring members are nitrogen atoms and 1 member is an oxygen or sulfur atom.

The term "heteroaralkyl" refers to a $C_{1-6}$ alkyl group containing a heteroaryl substituent. Examples include furylmethyl and pyridylpropyl. It is intended that the point of attachment to the rest of the molecule be the alkyl group.

The term "heteroaryl" refers to a radical derived by the removal of one hydrogen atom from a ring carbon atom of a heteroaromatic ring system. Typical heteroaryl radicals include furyl, thienyl, pyrrolyl, oxazolyl, thiazolyl, imidazolyl, pyrazolyl, isoxazolyl, isothiazolyl, oxadiazolyl, triazolyl, thiadiazolyl, pyridinyl, pyridazinyl, pyrimidinyl, pyrazinyl, indolizinyl, indolyl, isoindolyl, benzo[b]furyl, benzo[b]thienyl, indazolyl, benzimidazolyl, benzthiazolyl, purinyl, 4H-quinolizinyl, quinolinyl, isoquinolinyl, cinnolinyl, phthalzinyl, quinazolinyl, quinoxalinyl, 1,8-naphthyridinyl, pteridinyl and the like.

The term "heterocyclyl" refers to a saturated or partially unsaturated monocyclic ring radical derived by the removal of one hydrogen atom from a single carbon or nitrogen ring atom. Typical heterocyclyl radicals include 2H-pyrrolyl, 2-pyrrolinyl, 3-pyrrolinyl, pyrrolidinyl, 1,3-dioxolanyl, 2-imidazolinyl (also referred to as 4,5-dihydro-1H-imidazolyl), imidazolidinyl, 2-pyrazolinyl, pyrazolidinyl, tetrazolyl, piperidinyl, 1,4-dioxanyl, morpholinyl, 1,4-dithianyl, thiomorpholinyl, thiomorpholinyl 1,1 dioxide, piperazinyl, azepanyl, hexahydro-1,4-diazepinyl and the like.

The term "oxo" refers to an oxygen atom radical; said oxygen atom has two open valencies which are bonded to the same atom, most preferably a carbon atom. The oxo group is an appropriate substituent for an alkyl group. For example, propane with an oxo substituent is either acetone or propionaldehyde. Heterocycles can also be substituted with an oxo group. For example, oxazolidine with an oxo substituent is oxazolidinone.

The term "protecting group" refers to a temporary substituent added to a molecule by chemical modification of a functional group, such as —$R_2$NH or —ROH, in order to obtain chemoselectivity in a subsequent chemical reaction. In many preparations of organic compounds, some functional groups present in the molecule cannot survive the required reagents or chemical environments. Such groups may be protected. After the step involving contraindicated reagents or chemical environments, the protecting group is removed, giving back the original functionality. Examples of protecting groups include, but are not limited to: —$CO_2$-tert-butyl, —$CO_2CH_2$Ph, —$CO_2CH_2$-9H-fluoren-9-yl, —$SO_2$Ph, and —$SO_2$toluyl.

The term "squaryl" refers to a cyclobutenyl 1,2 dione radical.

The term "substituted," refers to a core molecule on which one or more hydrogen atoms have been replaced with one or more functional radical moieties. Substitution is not limited to a core molecule, but may also occur on a substituent radical, whereby the substituent radical becomes a linking group.

The term "independently selected" refers to one or more substituents selected from a group of substituents, wherein the substituents may be the same or different.

The substituent nomenclature used in the disclosure of the present invention was derived by first indicating the atom having the point of attachment, followed by the linking group atoms toward the terminal chain atom from left to right, substantially as in:

($C_{1-6}$)alkylC(O)NH($C_{1-6}$)alkyl(Ph)

or by first indicating the terminal chain atom, followed by the linking group atoms toward the atom having the point of attachment, substantially as in:

Ph($C_{1-6}$)alkylamido($C_{1-6}$)alkyl either of which refers to a radical of the formula:

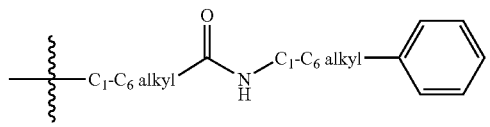

Lines drawn into ring systems from substituents indicate that the bond may be attached to any of the suitable ring atoms.

When any variable (e.g. $R_4$) occurs more than one time in any embodiment of Formula C, each definition is intended to be independent.

The terms "comprising", "including", and "containing" are used herein in their open, non-limited sense.

Nomenclature

Except where indicated, compound names were derived using nomenclature rules well known to those skilled in the art, by either standard IUPAC nomenclature references, such as *Nomenclature of Organic Chemistry, Sections A, B, C, D, E, F and H*, (Pergamon Press, Oxford, 1979, Copyright 1979 IUPAC) and *A Guide to IUPAC Nomenclature of Organic Compounds* (*Recommendations* 1993), (Blackwell Scientific Publications, 1993, Copyright 1993 IUPAC); or commercially available software packages such as Autonom (brand of nomenclature software provided in the ChemDraw Ultra® office suite marketed by CambridgeSoft.com); and ACD/Index Name™ (brand of commercial nomenclature software marketed by Advanced Chemistry Development, Inc., Toronto, Ontario).

Abbreviations

As used herein, the following abbreviations are intended to have the following meanings (additional abbreviations are provided where needed throughout the Specification):

| | |
|---|---|
| ATP | adenosine triphosphate |
| Boc | tert-butoxycarbonyl |
| DCM | dichloromethane |
| DMF | dimethylformamide |
| DMSO | dimethylsulfoxide |
| DIEA | diisopropylethylamine |
| EtOAc | ethyl acetate |
| Hex | hexane |
| LC/MS (ESI) | Liquid chromatography/mass spectrum (electrospray ionization) |
| MeOH | Methyl alcohol |
| NMR | nuclear magnetic resonance |
| RT | room temperature |
| RTK | receptor tyrosine kinase |
| TEA | triethylamine |
| TFA | trifluoroacetic acid |
| THF | tetrahydrofuran |
| TLC | thin layer chromatography |

Formula C

The present invention comprises compounds of Formula C:

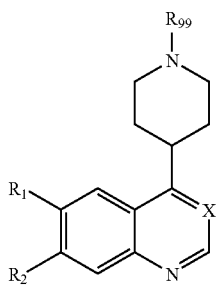

Formula C and N-oxides and stereochemical isomers thereof, wherein:
X is N or CH;
$R_1$ and $R_2$ are independently selected from:

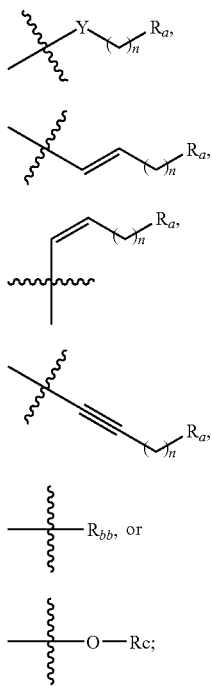

wherein n is 1, 2, 3 or 4;
Y is a direct bond, O, S, NH, or N(alkyl);
$R_a$ is alkoxy, phenoxy, heteroaryl optionally substituted with $R_5$ (wherein said heteroaryl is preferably pyrrolyl, furanyl, thiophenyl, imidazolyl, thiazolyl, oxazolyl, pyranyl, thiopyranyl, pyridinyl, pyrimidinyl, triazolyl, tetrazolyl, pyrazinyl, pyridinyl-N-oxide, or pyrrolyl-N-oxide, and most preferably pyrrolyl, furanyl, thiophenyl, imidazolyl, thiazolyl, oxazolyl, pyridinyl, pyrimidinyl, triazolyl, tetrazolyl, or pyrazinyl), hydroxyl, alkylamino, dialkylamino, oxazolidinonyl optionally substituted with $R_5$, pyrrolidinonyl optionally substituted with $R_5$, piperidinonyl optionally substituted with $R_5$, piperazinyl-2-one optionally substituted with $R_5$, cyclic heterodionyl optionally substituted with $R_5$, heterocyclyl optionally substituted with $R_5$ (wherein said heterocyclyl is preferably azepanyl, diazepanyl, azetidinyl, pyrrolidinyl, tetrahydrofuranyl, tetrahydrothiophenyl, imidazolidinyl, thiazolidinyl, oxazolidinyl, tetrahydropyranyl, tetrahydrothiopyranyl, piperidinyl, thiomorpholinyl, thiomorpholinyl 1,1-dioxide, morpholinyl, or piperazinyl), squaryl optionally substituted with $R_5$, —COOR$_y$, —CONR$_w$R$_x$, —N(R$_y$)CON(R$_w$)(R$_x$), —N(R$_w$)C(O)OR$_x$, —N(R$_w$)COR$_y$, —SR$_y$, —SOR$_y$, —SO$_2$R$_y$, —NR$_w$SO$_2$R$_y$, —NR$_w$SO$_2$R$_x$, —SO$_3$R$_y$, —OSO$_2$NR$_w$R$_x$, or —SO$_2$NR$_w$R$_x$;

$R_w$ and $R_x$ are independently selected from: hydrogen, alkyl, alkenyl, aralkyl (wherein the aryl portion of said aralkyl is preferably phenyl), or heteroaralkyl (wherein the heteroaryl portion of said heteroaralkyl is preferably pyrrolyl, furanyl, thiophenyl, imidazolyl, thiazolyl, oxazolyl, pyranyl, thiopyranyl, pyridinyl, pyrimidinyl, pyrazinyl, pyridinyl-N-oxide, or pyrrolyl-N-oxide, and most preferably pyrrolyl, furanyl, thiophenyl, imidazolyl, thiazolyl, oxazolyl, pyridinyl, pyrimidinyl, or pyrazinyl), or $R_w$ and $R_x$ may optionally be taken together to form a 5 to 7 membered ring, optionally containing a heteromoiety selected from O, NH, N(alkyl), SO, SO$_2$, or S, preferably selected from the group consisting of:

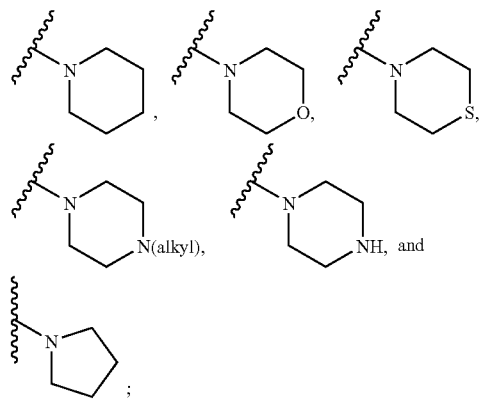

;

$R_y$ is selected from: hydrogen, alkyl, alkenyl, cycloalkyl (wherein said cycloalkyl is preferably cyclopentanyl or cyclohexanyl), phenyl, aralkyl (wherein the aryl portion of said aralkyl is preferably phenyl), heteroaralkyl (wherein the heteroaryl portion of said heteroaralkyl is preferably pyrrolyl, furanyl, thiophenyl, imidazolyl, thiazolyl, oxazolyl, pyranyl, thiopyranyl, pyridinyl, pyrimidinyl, pyrazinyl, pyridinyl-N-oxide, or pyrrolyl-N-oxide, and most preferably pyrrolyl, furanyl, thiophenyl, imidazolyl, thiazolyl, oxazolyl, pyridinyl, pyrimidinyl, or pyrazinyl), or heteroaryl (wherein said heteroaryl is preferably pyrrolyl, furanyl, thiophenyl, imidazolyl, thiazolyl, oxazolyl, pyranyl, thiopyranyl, pyridinyl, pyrimidinyl, pyrazinyl, pyridinyl-N-oxide, or pyrrolyl-N-oxide, and most preferably pyrrolyl, furanyl, thiophenyl, imidazolyl, thiazolyl, oxazolyl, pyridinyl, pyrimidinyl, or pyrazinyl);

$R_5$ is one, two, or three substituents independently selected from: halogen, cyano, trifluoromethyl, amino, hydroxyl, heteroaryl, alkoxy, —C(O)alkyl, —SO$_2$alkyl, —C(O)NH(alkyl), —C(O)N(alkyl)$_2$, —C(O)C$_{(1-4)}$alkyl-N(alkyl)$_2$, alkyl, —C$_{(1-4)}$alkyl-OH, —C$_{(1-4)}$alkyl-OCH$_3$, —C(O)C$_{(1-4)}$alkyl-OH, —C(O)C$_{(1-4)}$alkyl-OCH$_3$, a protecting group (wherein said protecting group is preferrably fluoren-9-yl-methyl-oxy carbonyl), dialkylamino, or alkylamino; provided that the same $R_5$ substituent is not present more than once, unless said $R_5$ substituent is halogen, hydroxyl, alkoxy, or alkyl;

$R_{bb}$ is hydrogen provided that both $R_1$ and $R_2$ are not hydrogen; or $R_{bb}$ is alkoxy provided that both $R_1$ and $R_2$ are not alkoxy; or $R_{bb}$ is selected from the group consisting of: halogen, dialkylamino, phenyl optionally substituted with $R_6$, heteroaryl optionally substituted with $R_6$ (wherein said heteroaryl is preferably pyrrolyl, furanyl, thiophenyl, imidazolyl, thiazolyl, oxazolyl, pyranyl, thiopyranyl, pyridinyl, pyrimidinyl, triazolyl, pyrazinyl, pyridinyl-N-oxide, or pyrrolyl-N-oxide, and most preferably pyrrolyl, furanyl, thiophenyl, imidazolyl, thiazolyl, oxazolyl, pyridinyl, pyrimidinyl, triazolyl, or pyrazinyl), piperazinyl-2-one optionally substituted with $R_6$, imidazolidinyl-2-one optionally substituted with $R_6$, oxazolidinyl-2-one optionally substituted with $R_6$, or heterocyclyl optionally substituted with $R_6$ (wherein said heterocyclyl is preferably azepanyl and diazepanyl, azetidinyl, pyrrolidinyl, tetrahydrofuranyl, tetrahydrothiophenyl, imidazolidinyl, thiazolidinyl, oxazolidinyl, tetrahydropyranyl, tetrahydrothiopyranyl, piperidinyl, thiomorpholinyl, thiomorpholinyl 1,1-dioxide, morpholinyl or piperazinyl);

$R_6$ is one, two, or three substituents independently selected from: halogen, cyano, trifluoromethyl, amino, hydroxyl, heteroaryl, alkoxy, —C(O)alkyl, —SO$_2$alkyl, —C(O)NH(alkyl), —C(O)N(alkyl)$_2$, —C(O)C$_{(1-4)}$alkyl-N(alkyl)$_2$, alkyl, —C$_{(1-4)}$alkyl-OH, —C$_{(1-4)}$alkyl-OCH$_3$, —C(O)C$_{(1-4)}$alkyl-OH, —C(O)C$_{(1-4)}$alkyl-OCH$_3$, dialkylamino, or alkylamino; provided that the same $R_6$ substituent is not present more than once, unless said $R_6$ substituent is halogen, hydroxyl, alkoxy, or alkyl;

$R_c$ is heterocyclyl optionally substituted with $R_7$ (wherein said heterocyclyl is preferably azepanyl, diazepanyl, azetidinyl, pyrrolidinyl, tetrahydrofuranyl, tetrahydrothiophenyl, imidazolidinyl, thiazolidinyl, oxazolidinyl, tetrahydropyranyl, tetrahydrothiopyranyl, piperidinyl, thiomorpholinyl, thiomorpholinyl 1,1-dioxide, morpholinyl, or piperazinyl), or heteroaryl (wherein said heteroaryl is preferably pyrrolyl, furanyl, thiophenyl, imidazolyl, thiazolyl, oxazolyl, pyridinyl, pyrimidinyl, or pyrazinyl); and $R_7$ is one, two, or three substituents independently selected from: halogen, cyano, trifluoromethyl, amino, hydroxyl, heteroaryl, alkoxy, —C(O)alkyl, —SO$_2$alkyl, —C(O)NH(alkyl), —C(O)N(alkyl)$_2$, —C(O)C$_{(1-4)}$alkyl-N(alkyl)$_2$, alkyl, —C$_{(1-4)}$alkyl-OH, —C$_{(1-4)}$alkyl-OCH$_3$, —C(O)C$_{(1-4)}$alkyl-OH, —C(O)C$_{(1-4)}$alkyl-OCH$_3$, dialkylamino, or alkylamino; provided that the same $R_7$ substituent is not present more than once, unless said $R_7$ substituent is halogen, hydroxyl, alkoxy, or alkyl; and $R_{99}$ is hydrogen or a protecting group (wherein said protecting group is preferably —CO$_2$-tert-butyl, —CO$_2$CH$_2$Ph, —CO$_2$CH$_2$-9H-fluoren-9-yl, —SO$_2$Ph, or —SO$_2$toluyl).

As used hereafter, the term "compounds of Formula C" is meant to include the N-oxides and stereochemical isomers thereof.

Embodiments of Formula C

In an embodiment of the present invention: N-oxides are optionally present on one or more of: N-1 or N-3 (when X is N) (see FIG. 1 below for ring numbers).

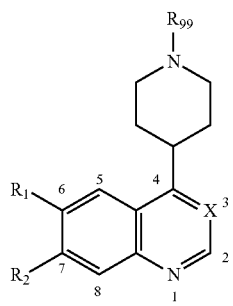

Figure 1

FIG. 1 illustrates ring atoms numbered 1 through 8, as used in the present specification.

Preferred embodiments of the invention are compounds of Formula C wherein one or more of the following limitations are present:

X is N or CH;

$R_1$ and $R_2$ are independently selected from:

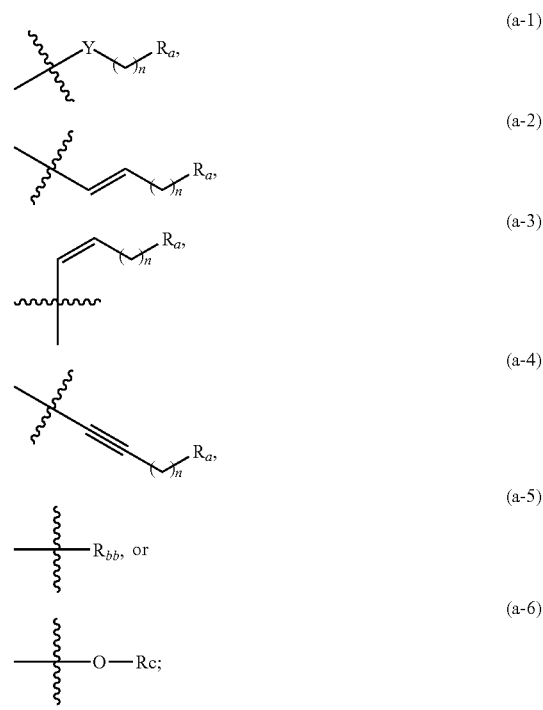

wherein n is 1, 2, 3 or 4;

Y is a direct bond, O, S, NH, or N(alkyl);

$R_a$ is alkoxy, phenoxy, heteroaryl optionally substituted with $R_5$, hydroxyl, alkylamino, dialkylamino, oxazolidinonyl optionally substituted with $R_5$, pyrrolidinonyl optionally substituted with $R_5$, piperidinonyl optionally substituted with $R_5$, piperazinyl-2-one optionally substituted with $R_5$, cyclic heterodionyl optionally substituted with $R_5$, heterocyclyl optionally substituted with $R_5$, squaryl optionally substituted with $R_5$, —COOR$_y$, —CONR$_w$R$_x$, —N(R$_y$)CON(R$_w$)(R$_x$), —N(R$_w$)C(O)OR$_x$, —N(R$_w$)COR$_y$, —SR$_y$, —SOR$_y$, —SO$_2$R$_y$, —NR$_w$SO$_2$R$_y$, —NR$_w$SO$_2$R$_x$, —SO$_3$R$_y$, —OSO$_2$NR$_w$R$_x$, or —SO$_2$NR$_w$R$_x$;

$R_w$ and $R_x$ are independently selected from: hydrogen, alkyl, alkenyl, aralkyl or heteroaralkyl, or $R_w$ and $R_x$ may optionally be taken together to form a 5 to 7 membered ring, optionally containing a heteromoiety selected from O, NH, N(alkyl), SO, $SO_2$, or S;

$R_y$ is selected from: hydrogen, alkyl, alkenyl, cycloalkyl, phenyl, aralkyl, heteroaralkyl, or heteroaryl;

$R_5$ is one, two, or three substituents independently selected from: halogen, cyano, trifluoromethyl, amino, hydroxyl, heteroaryl, alkoxy, —C(O)alkyl, —$SO_2$alkyl, —C(O)NH(alkyl), —C(O)N(alkyl)$_2$, —C(O)C$_{(1-4)}$ alkyl-N(alkyl)$_2$, alkyl, —C$_{(1-4)}$alkyl-OH, —C$_{(1-4)}$alkyl-OCH$_3$, —C(O)C$_{(1-4)}$alkyl-OH, —C(O)C$_{(1-4)}$alkyl-OCH$_3$, a protecting group (wherein said protecting group is preferrably fluoren-9-yl-methyl-oxy carbonyl), dialkylamino, or alkylamino; provided that the same $R_5$ substituent is not present more than once, unless said $R_5$ substituent is halogen, hydroxyl, alkoxy, or alkyl;

$R_{bb}$ is hydrogen provided that both $R_1$ and $R_2$ are not hydrogen; or $R_{bb}$ is alkoxy provided that both $R_1$ and $R_2$ are not alkoxy; or $R_{bb}$ is selected from the group consisting of: halogen, dialkylamino, phenyl, heteroaryl, piperazinyl-2-one optionally substituted with $R_6$, imidazolidinyl-2-one optionally substituted with $R_6$, oxazolidinyl-2-one optionally substituted with $R_6$, or heterocyclyl optionally substituted with $R_6$;

$R_6$ is one, two, or three substituents independently selected from: halogen, cyano, trifluoromethyl, amino, hydroxyl, heteroaryl, alkoxy, —C(O)alkyl, —$SO_2$alkyl, —C(O)NH(alkyl), —C(O)N(alkyl)$_2$, —C(O)C$_{(1-4)}$ alkyl-N(alkyl)$_2$, alkyl, —C$_{(1-4)}$alkyl-OH, —C$_{(1-4)}$alkyl-OCH$_3$, —C(O)C$_{(1-4)}$alkyl-OH, —C(O)C$_{(1-4)}$alkyl-OCH$_3$, dialkylamino, or alkylamino; provided that the same $R_6$ substituent is not present more than once, unless said $R_6$ substituent is halogen, hydroxyl, alkoxy, or alkyl;

$R_c$ is heterocyclyl optionally substituted with $R_7$, or heteroaryl; and $R_7$ is one, two, or three substituents independently selected from: halogen, cyano, trifluoromethyl, amino, hydroxyl, heteroaryl, alkoxy, —C(O)alkyl, —$SO_2$alkyl, —C(O)NH(alkyl), —C(O)N(alkyl)$_2$, —C(O)C$_{(1-4)}$ alkyl-N(alkyl)$_2$, alkyl, —C$_{(1-4)}$alkyl-OH, —C$_{(1-4)}$alkyl-OCH$_3$, —C(O)C$_{(1-4)}$alkyl-OH, —C(O)C$_{(1-4)}$alkyl-OCH$_3$, dialkylamino, or alkylamino; provided that the same $R_7$ substituent is not present more than once, unless said $R_7$ substituent is halogen, hydroxyl, alkoxy, or alkyl; and $R_{99}$ is hydrogen, or a protecting group (wherein said protecting group is preferably —$CO_2$-tert-butyl, —$CO_2CH_2$Ph, —$CO_2CH_2$-9H-fluoren-9-yl, —$SO_2$Ph, or —$SO_2$toluyl).

Still other preferred embodiments of the invention are compounds of Formula C wherein one or more of the following limitations are present:

X is N or CH;

$R_1$ and $R_2$ are independently selected from:

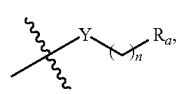
(a-1)

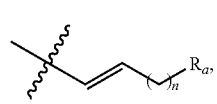
(a-2)

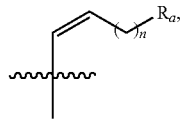
(a-3)

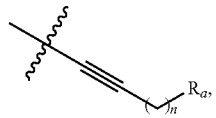
(a-4)

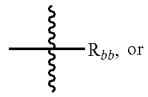
(a-5)

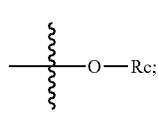
(a-6)

wherein n is 1, 2, 3 or 4;

Y is a direct bond, O, or NH;

$R_a$ is alkoxy, heteroaryl optionally substituted with $R_5$, hydroxyl, alkylamino, dialkylamino, oxazolidinonyl optionally substituted with $R_5$, pyrrolidinonyl optionally substituted with $R_5$, piperidinonyl optionally substituted with $R_5$, piperazinyl-2-one optionally substituted with $R_5$, cyclic heterodionyl optionally substituted with $R_5$, heterocyclyl optionally substituted with $R_5$, squaryl optionally substituted with $R_5$, —CONR$_w$R$_x$, —N(R$_y$)CON(R$_w$)(R$_x$), —N(R$_w$)C(O)OR$_x$, —N(R$_w$)COR$_y$, —SR$_y$, —SOR$_y$, —$SO_2$R$_y$, or —NR$_w$$SO_2$R$_y$;

$R_w$ and $R_x$ are independently selected from: hydrogen, alkyl, alkenyl, aralkyl, or heteroaralkyl, or $R_w$ and $R_x$ may optionally be taken together to form a 5 to 7 membered ring, optionally containing a heteromoiety selected from O, NH, N(alkyl), SO, $SO_2$, or S;

$R_y$ is selected from: hydrogen, alkyl, alkenyl, cycloalkyl, phenyl, aralkyl, heteroaralkyl, or heteroaryl;

$R_5$ is one, two, or three substituents independently selected from: halogen, cyano, trifluoromethyl, amino, hydroxyl, heteroaryl, alkoxy, —C(O)alkyl, —$SO_2$alkyl, —C(O)NH(alkyl), —C(O)N(alkyl)$_2$, —C(O)C$_{(1-4)}$alkyl-N(alkyl)$_2$, alkyl, —C$_{(1-4)}$alkyl-OH, —C$_{(1-4)}$alkyl-OCH$_3$, —C(O)C$_{(1-4)}$alkyl-OH, —C(O)C$_{(1-4)}$alkyl-OCH$_3$, a protecting group (wherein said protecting group is preferrably fluoren-9-yl-methyl-oxy carbonyl), dialkylamino, or alkylamino; provided that the same $R_5$ substituent is not present more than once, unless said $R_5$ substituent is halogen, hydroxyl, alkoxy, or alkyl;

$R_{bb}$ is hydrogen provided that both $R_1$ and $R_2$ are not hydrogen; or $R_{bb}$ is alkoxy provided that both $R_1$ and $R_2$ are not alkoxy; or $R_{bb}$ is selected from the group consisting of: halogen, piperazinyl-2-one optionally substituted with $R_6$, imidazolidinyl-2-one optionally substituted with $R_6$, oxazolidinyl-2-one optionally substituted with $R_6$, or heterocyclyl optionally substituted with $R_6$;

$R_6$ is one, two, or three substituents independently selected from: halogen, cyano, trifluoromethyl, amino, hydroxyl, heteroaryl, alkoxy, —C(O)alkyl, —$SO_2$alkyl, —C(O)NH(alkyl), —C(O)N(alkyl)$_2$, —C(O)C$_{(1-4)}$alkyl-N(alkyl)$_2$, alkyl, —C$_{(1-4)}$alkyl-OH, —C$_{(1-4)}$alkyl-OCH$_3$, —C(O)C$_{(1-4)}$alkyl-OH, —C(O)C$_{(1-4)}$alkyl-OCH$_3$, dialkylamino, or alkylamino; provided that the same $R_6$ substituent is not present more than once, unless said $R_6$ substituent is halogen, hydroxyl, alkoxy, or alkyl;

$R_c$ is heterocyclyl optionally substituted with $R_7$, or heteroaryl; and $R_7$ is one, two, or three substituents independently selected from: halogen, cyano, trifluoromethyl, amino, hydroxyl, heteroaryl, alkoxy, —C(O)alkyl, —SO$_2$alkyl, —C(O)NH(alkyl), —C(O)N(alkyl)$_2$, —C(O)C$_{(1-4)}$alkyl-N(alkyl)$_2$, alkyl, —C$_{(1-4)}$alkyl-OH, —C$_{(1-4)}$alkyl-OCH$_3$, —C(O)C$_{(1-4)}$alkyl-OH, —C(O)C$_{(1-4)}$alkyl-OCH$_3$, dialkylamino, or alkylamino; provided that the same $R_7$ substituent is not present more than once, unless said $R_7$ substituent is halogen, hydroxyl, alkoxy, or alkyl; and $R_{99}$ is hydrogen, or a protecting group (wherein said protecting group is preferably —CO$_2$-tert-butyl, —CO$_2$CH$_2$Ph, —CO$_2$CH$_2$-9H-fluoren-9-yl, —SO$_2$Ph, or —SO$_2$toluyl).

Particularly preferred embodiments of the invention are compounds of Formula C wherein one or more of the following limitations are present:

X is N or CH;

$R_1$ and $R_2$ are independently selected from:

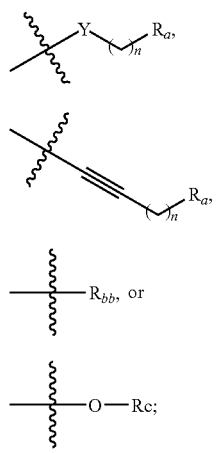

wherein n is 1, 2, 3 or 4;

Y is O or NH;

$R_a$ is alkoxy, heteroaryl optionally substituted with $R_5$, hydroxyl, alkylamino, dialkylamino, oxazolidinonyl optionally substituted with $R_5$, pyrrolidinonyl optionally substituted with $R_5$, piperidinonyl optionally substituted with $R_5$, piperazinyl-2-one optionally substituted with $R_5$, heterocyclyl optionally substituted with $R_5$, squaryl optionally susbstituted with $R_5$, —CONR$_w$R$_x$, —N(R$_y$)CON(R$_w$)(R$_x$), —N(R$_w$)C(O)OR$_x$, —N(R$_w$)COR$_y$, —SO$_2$R$_y$, or —NR$_w$SO$_2$R$_y$;

$R_w$ and $R_x$ are independently selected from: hydrogen, alkyl, alkenyl, aralkyl, or heteroaralkyl, or $R_w$ and $R_x$ may optionally be taken together to form a 5 to 7 membered ring, optionally containing a heteromoiety selected from O, NH, N(alkyl), SO, SO$_2$, or S;

$R_y$ is selected from: hydrogen, alkyl, alkenyl, cycloalkyl, phenyl, aralkyl, heteroaralkyl, or heteroaryl;

$R_5$ is one or two substituents selected from: —C(O)alkyl, —SO$_2$alkyl, —C(O)NH(alkyl), —C(O)N(alkyl)$_2$, —C(O)C$_{(1-4)}$alkyl-N(alkyl)$_2$, alkyl, —C$_{(1-4)}$alkyl-OH, —C$_{(1-4)}$alkyl-OCH$_3$, —C(O)C$_{(1-4)}$alkyl-OH, fluoren-9-yl-methyl-oxy carbonyl, or —C(O)C$_{(1-4)}$alkyl-OCH$_3$; provided that the same $R_5$ substituent is not present more than once, unless said $R_5$ substituent is alkyl;

$R_{bb}$ is hydrogen provided that both $R_1$ and $R_2$ are not hydrogen; or $R_{bb}$ is alkoxy provided that both $R_1$ and $R_2$ are not alkoxy; or $R_{bb}$ is selected from the group consisting of: halogen, piperazinyl-2-one optionally substituted with $R_6$, imidazolidinyl-2-one optionally substituted with $R_6$, oxazolidinyl-2-one optionally substituted with $R_6$, or heterocyclyl optionally substituted with $R_6$;

$R_6$ is one or two substituents independently selected from: halogen, hydroxyl, heteroaryl, alkoxy, —C(O)alkyl, —SO$_2$alkyl, —C(O)NH(alkyl), —C(O)N(alkyl)$_2$, —C(O)C$_{(1-4)}$alkyl-N(alkyl)$_2$, alkyl, —C$_{(1-4)}$alkyl-OH, —C$_{(1-4)}$alkyl-OCH$_3$, —C(O)C$_{(1-4)}$alkyl-OH, or -C(O)C$_{(1-4)}$alkyl-OCH$_3$; provided that the same $R_6$ substituent is not present more than once, unless said $R_6$ substituent is halogen, hydroxyl, or alkyl;

$R_c$ is heterocyclyl optionally substituted with $R_7$;

$R_7$ is one substituent selected from: hydroxyl, —C(O)alkyl, —SO$_2$alkyl, alkyl, or —C(O)N(alkyl)$_2$; and $R_{99}$ is hydrogen, or a protecting group (wherein said protecting group is preferably —CO$_2$-tert-butyl, —CO$_2$CH$_2$Ph, —CO$_2$CH$_2$-9H-fluoren-9-yl, —SO$_2$Ph, or —SO$_2$toluyl).

Most particularly preferred embodiments of the invention are compounds of Formula C wherein one or more of the following limitations are present:

X is N or CH;

$R_1$ and $R_2$ are independently selected from:

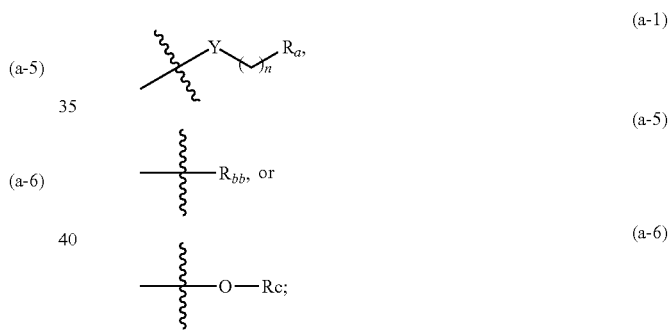

wherein n is 1, 2, 3 or 4;

Y is O;

$R_a$ is alkoxy, heteroaryl optionally substituted with $R_5$, hydroxyl, alkylamino, dialkylamino, oxazolidinonyl optionally substituted with $R_5$, pyrrolidinonyl optionally substituted with $R_5$, piperazinyl-2-one optioanlly substituted with $R_5$, heterocyclyl optionally substituted with $R_5$, —CONR$_w$R$_x$, —N(R$_y$)CON(R$_w$)(R$_x$), —SO$_2$R$_y$, or —NR$_w$SO$_2$R$_y$;

$R_w$ and $R_x$ are independently selected from: hydrogen, alkyl, alkenyl, aralkyl, or heteroaralkyl, or $R_w$ and $R_x$ may optionally be taken together to form a 5 to 7 membered ring, optionally containing a heteromoiety selected from O, NH, N(alkyl), SO, SO$_2$, or S;

$R_y$ is selected from: hydrogen, alkyl, alkenyl, cycloalkyl, phenyl, aralkyl, heteroaralkyl, or heteroaryl;

$R_5$ is one substituent selected from: —C(O)alkyl, —SO$_2$alkyl, —C(O)NH(alkyl), —C(O)N(alkyl)$_2$, —C(O)C$_{1-4}$alkyl-N(alkyl)$_2$, alkyl, —C$_{(1-4)}$alkyl-OH, —C$_{(1-4)}$alkyl-OCH$_3$, —C(O)C$_{(1-4)}$alkyl-OH, fluoren-9-yl-methyl-oxy carbonyl, or —C(O)C$_{(1-4)}$alkyl-OCH$_3$;

$R_{bb}$ is hydrogen provided that both $R_1$ and $R_2$ are not hydrogen; or $R_{bb}$ is alkoxy provided that both $R_1$ and $R_2$ are not alkoxy; or $R_{bb}$ is selected from the group consisting of: halogen, piperazinyl-2-one optionally substituted with $R_6$, imidazolidinyl-2-one optionally substituted with $R_6$, oxazolidinyl-2-one optionally substituted with $R_6$, or heterocyclyl optionally substituted with $R_6$;

$R_6$ is one substituent selected from: hydroxyl, alkoxy, —C(O)alkyl, —SO$_2$alkyl, —C(O)NH(alkyl), —C(O)N(alkyl)$_2$, —C(O)C$_{1-4}$alkyl-N(alkyl)$_2$, alkyl, —C$_{(1-4)}$alkyl-OH, —C$_{(1-4)}$alkyl-OCH$_3$, —C(O)C$_{(1-4)}$alkyl-OH, or —C(O)C$_{(1-4)}$alkyl-OCH$_3$;

$R_c$ is heterocyclyl optionally substituted with $R_7$;

$R_7$ is one substituent selected from —C(O)alkyl, —SO$_2$alkyl, or alkyl; and $R_{99}$ is hydrogen, or a protecting group (wherein said protecting group is preferably —CO$_2$-tert-butyl, —CO$_2$CH$_2$Ph, —CO$_2$CH$_2$-9H-fluoren-9-yl, —SO$_2$Ph, or —SO$_2$toluyl).

Stereochemical Isomers

One skilled in the art will recognize that the compounds of Formula C may have one or more asymmetric carbon atoms in their structure. It is intended that the present invention include within its scope single enantiomer forms of the compounds, racemic mixtures, and mixtures of enantiomers in which an enantiomeric excess is present.

The term "single enantiomer" as used herein defines all the possible homochiral forms which the compounds of Formula C and their N-oxides, addition salts, quaternary amines or physiologically functional derivatives may possess.

Stereochemically pure isomeric forms may be obtained by the application of art known principles. Diastereoisomers may be separated by physical separation methods such as fractional crystallization and chromatographic techniques, and enantiomers may be separated from each other by the selective crystallization of the diastereomeric salts with optically active acids or bases or by chiral chromatography. Pure stereoisomers may also be prepared synthetically from appropriate stereochemically pure starting materials, or by using stereoselective reactions.

The term "isomer" refers to compounds that have the same composition and molecular weight but differ in physical and/or chemical properties. Such substances have the same number and kind of atoms but differ in structure. The structural difference may be in constitution (geometric isomers) or in an ability to rotate the plane of polarized light (enantiomers).

The term "stereoisomer" refers to isomers of identical constitution that differ in the arrangement of their atoms in space. Enantiomers and diastereomers are examples of stereoisomers.

The term "chiral" refers to the structural characteristic of a molecule that makes it impossible to superimpose it on its mirror image.

The term "enantiomer" refers to one of a pair of molecular species that are mirror images of each other and are not superimposable.

The term "diastereomer" refers to stereoisomers that are not mirror images.

The symbols "R" and "S" represent the configuration of substituents around a chiral carbon atom(s).

The term "racemate" or "racemic mixture" refers to a composition composed of equimolar quantities of two enantiomeric species, wherein the composition is devoid of optical activity.

The term "homochiral" refers to a state of enantiomeric purity.

The term "optical activity" refers to the degree to which a homochiral molecule or nonracemic mixture of chiral molecules rotates a plane of polarized light.

The term "geometric isomer" refers to isomers that differ in the orientation of substituent atoms in relationship to a carbon-carbon double bond, to a cycloalkyl ring or to a bridged bicyclic system. Substituent atoms (other than H) on each side of a carbon-carbon double bond may be in an E or Z configuration. In the "E" (opposite sided) configuration, the substituents are on opposite sides in relationship to the carbon-carbon double bond; in the "Z" (same sided) configuration, the substituents are oriented on the same side in relationship to the carbon-carbon double bond. Substituent atoms (other than hydrogen) attached to a carbocyclic ring may be in a cis or trans configuration. In the "cis" configuration, the substituents are on the same side in relationship to the plane of the ring; in the "trans" configuration, the substituents are on opposite sides in relationship to the plane of the ring. Compounds having a mixture of "cis" and "trans" species are designated "cis/trans".

It is to be understood that the various substituent stereoisomers, geometric isomers and mixtures thereof used to prepare compounds of the present invention are either commercially available, can be prepared synthetically from commercially available starting materials or can be prepared as isomeric mixtures and then obtained as resolved isomers using techniques well-known to those of ordinary skill in the art.

The isomeric descriptors "R," "S," "E," "Z," "cis," and "trans" are used as described herein for indicating atom configuration(s) relative to a core molecule and are intended to be used as defined in the literature (IUPAC Recommendations for Fundamental Stereochemistry (Section E), *Pure Appl. Chem.*, 1976, 45:13-30).

The compounds of the present invention may be prepared as individual isomers by either isomer-specific synthesis or resolved from an isomeric mixture. Conventional resolution techniques include forming the free base of each isomer of an isomeric pair using an optically active salt (followed by fractional crystallization and regeneration of the free base), forming an ester or amide of each of the isomers of an isomeric pair (followed by chromatographic separation and removal of the chiral auxiliary) or resolving an isomeric mixture of either a starting material or a final product using preparative TLC (thin layer chromatography) or a chiral HPLC column.

Polymorphs and Solvates

Furthermore, compounds of the present invention may have one or more polymorph or amorphous crystalline forms and as such are intended to be included in the scope of the invention. In addition, some of the compounds may form solvates, for example with water (i.e., hydrates) or common organic solvents. As used herein, the term "solvate" means a physical association of a compound of the present invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. The term "solvate" is intended to encompass both solution-phase and isolatable solvates. Non-limiting examples of suitable solvates include ethanolates, methanolates, and the like. It is intended that the present invention include within its scope solvates of the compounds of the present invention.

N-Oxides

The compounds of Formula C may be converted to the corresponding N-oxide forms following art-known procedures for converting a trivalent nitrogen into its N-oxide form. Said N-oxidation reaction may generally be carried out by reacting the starting material of Formula C with an appropriate organic or inorganic peroxide. Appropriate inorganic peroxides comprise, for example, hydrogen peroxide, alkali metal or earth alkaline metal peroxides, e.g. sodium peroxide, potassium peroxide; appropriate organic peroxides may comprise peroxy acids such as, for example, benzenecarboperoxoic acid or halo substituted benzenecarboperoxoic acid, e.g. 3-chlorobenzenecarboperoxoic acid, peroxoalkanoic acids, e.g. peroxoacetic acid, alkylhydroperoxides, e.g. tbutyl hydro-peroxide. Suitable solvents are, for example, water, lower alcohols, e.g. ethanol and the like, hydrocarbons, e.g. toluene, ketones, e.g. 2-butanone, halogenated hydrocarbons, e.g. dichloromethane, and mixtures of such solvents.

Tautomeric Forms

Some of the compounds of Formula C may also exist in their tautomeric forms. Such forms although not explicitly indicated in the present application are intended to be included within the scope of the present invention.

Use of the Compounds of Formula C

The compounds of Formula C can be used in the synthesis of the quinoline and quinazoline compounds of Formula I (which are inhibitors of FLT3, c-kit and/or TrkB kinase):

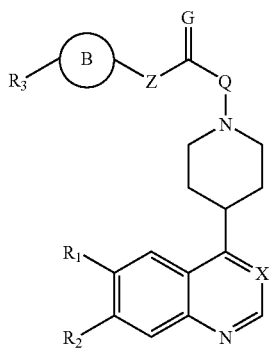

Formula I and N-oxides, pharmaceutically acceptable salts, solvates, and stereochemical isomers thereof, wherein:

$Q$ is $CH_2$ or a direct bond;

$G$ is O or S;

$X$ is N or CH;

$Z$ is NH, N(alkyl), or $CH_2$;

$B$ is phenyl, cycloalkyl (wherein said cycloalkyl is preferably cyclopentanyl, cyclohexanyl, cyclopentenyl or cyclohexenyl), heteroaryl (wherein said heteroaryl is preferably pyrrolyl, furanyl, thiophenyl, imidazolyl, thiazolyl, oxazolyl, pyranyl, thiopyranyl, pyridinyl, pyrimidinyl, pyrazinyl, pyridinyl-N-oxide, or pyrrolyl-N-oxide, and most preferably pyrrolyl, furanyl, thiophenyl, imidazolyl, thiazolyl, oxazolyl, pyridinyl, pyrimidinyl, or pyrazinyl), a nine to ten membered benzo-fused heteroaryl (wherein said nine to ten membered benzo-fused heteroaryl is preferably benzothiazolyl, benzooxazolyl, benzoimidazolyl, benzofuranyl, indolyl, quinolinyl, isoquinolinyl, or benzo[b]thiophenyl), or a nine to ten membered benzo-fused heterocyclyl (wherein said nine to ten membered benzo-fused heterocyclyl is preferably 2,3-dihydro-benzothiazolyl, 2,3-dihydro-benzooxazolyl, 2,3-dihydro-benzoimidazolyl, 1,2,3,4-tetrahydro-quinolinyl, 1,2,3,4-tetrahydroisoquinolinyl, isochromanyl, 2,3-dihydro-indolyl, 2,3-dihydro-benzofuranyl or 2,3-dihydro-benzo[b]thiophenyl, and most preferably 2,3-dihydro-indolyl, 2,3-dihydro-benzofuranyl or 2,3-dihydro-benzo[b]thiophenyl);

$R_1$ and $R_2$ are independently selected from:

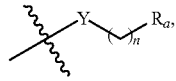  (a-1)

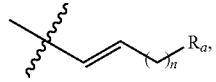  (a-2)

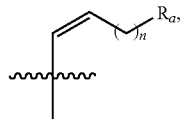  (a-3)

  (a-4)

  (a-5)

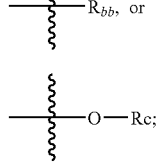  (a-6)

wherein $n$ is 1, 2, 3 or 4;

$Y$ is a direct bond, O, S, NH, or N(alkyl);

$R_a$ is alkoxy, phenoxy, heteroaryl optionally substituted with $R_5$ (wherein said heteroaryl is preferably pyrrolyl, furanyl, thiophenyl, imidazolyl, thiazolyl, oxazolyl, pyranyl, thiopyranyl, pyridinyl, pyrimidinyl, triazolyl, tetrazolyl, pyrazinyl, pyridinyl-N-oxide, or pyrrolyl-N-oxide, and most preferably pyrrolyl, furanyl, thiophenyl, imidazolyl, thiazolyl, oxazolyl, pyridinyl, pyrimidinyl, triazolyl, tetrazolyl, or pyrazinyl), hydroxyl, alkylamino, dialkylamino, oxazolidinonyl optionally substituted with $R_5$, pyrrolidinonyl optionally substituted with $R_5$, piperidinonyl optionally substituted with $R_5$, piperazinyl-2-one optionally substituted with $R_5$, cyclic heterodionyl optionally substituted with $R_5$, heterocyclyl optionally substituted with $R_5$ (wherein said heterocyclyl is preferably azepanyl, diazepanyl, azetidinyl, pyrrolidinyl, tetrahydrofuranyl, tetrahydrothiophenyl, imidazolidinyl, thiazolidinyl, oxazolidinyl, tetrahydropyranyl, tetrahydrothiopyranyl, piperidinyl, thiomorpholinyl, thiomorpholinyl 1,1-dioxide, morpholinyl, or piperazinyl), squaryl optionally substituted with $R_5$, —$COOR_y$, —$CONR_wR_x$, —$N(R_y)CON(R_w)(R_x)$, —$N(R_w)C(O)OR_y$, —$N(R_w)COR_y$, —$SR_y$, —$SOR_y$, —$SO_2R_y$, —$NR_wSO_2R_y$, —$NR_wSO_2R_x$, —$SO_3R_y$, —$OSO_2NR_wR_x$, or —$SO_2NR_wR_x$;

$R_w$ and $R_x$ are independently selected from: hydrogen, alkyl, alkenyl, aralkyl (wherein the aryl portion of said aralkyl is preferrably phenyl), or heteroaralkyl (wherein the heteroaryl portion of said heteroaralkyl is preferably pyrrolyl, furanyl, thiophenyl, imidazolyl, thiazolyl, oxazolyl, pyranyl, thiopyranyl, pyridinyl, pyrimidinyl, pyrazinyl, pyridinyl-N-oxide, or pyrrolyl-N-oxide, and most preferably pyrrolyl, furanyl, thiophenyl, imidazolyl, thiazolyl, oxazolyl, pyridinyl, pyrimidinyl, or pyrazinyl), or $R_w$ and $R_x$ may optionally be taken together to form a 5 to 7 membered ring, optionally containing a heteromoiety selected from O, NH, N(alkyl), SO, SO$_2$, or S, preferably selected from the group consisting of:

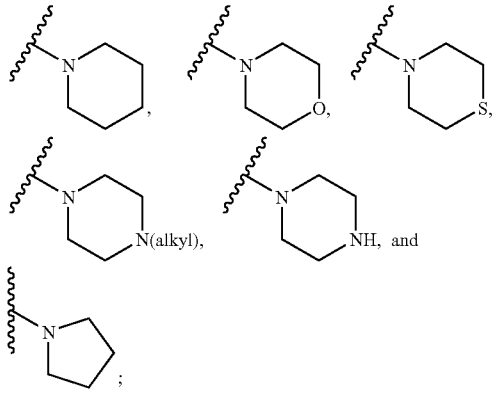

$R_y$ is selected from: hydrogen, alkyl, alkenyl, cycloalkyl (wherein said cycloalkyl is preferably cyclopentanyl or cyclohexanyl), phenyl, aralkyl (wherein the aryl portion of said aralkyl is preferably phenyl), heteroaralkyl (wherein the heteroaryl portion of said heteroaralkyl is preferably pyrrolyl, furanyl, thiophenyl, imidazolyl, thiazolyl, oxazolyl, pyranyl, thiopyranyl, pyridinyl, pyrimidinyl, pyrazinyl, pyridinyl-N-oxide, or pyrrolyl-N-oxide, and most preferably pyrrolyl, furanyl, thiophenyl, imidazolyl, thiazolyl, oxazolyl, pyridinyl, pyrimidinyl, or pyrazinyl), or heteroaryl (wherein said heteroaryl is preferably pyrrolyl, furanyl, thiophenyl, imidazolyl, thiazolyl, oxazolyl, pyranyl, thiopyranyl, pyridinyl, pyrimidinyl, pyrazinyl, pyridinyl-N-oxide, or pyrrolyl-N-oxide, and most preferably pyrrolyl, furanyl, thiophenyl, imidazolyl, thiazolyl, oxazolyl, pyridinyl, pyrimidinyl, or pyrazinyl);

$R_5$ is one, two, or three substituents independently selected from: halogen, cyano, trifluoromethyl, amino, hydroxyl, heteroaryl, alkoxy, —C(O)alkyl, —SO$_2$alkyl, —C(O)NH(alkyl), —C(O)N(alkyl)$_2$, —C(O)C$_{(1-4)}$alkyl-N(alkyl)$_2$, alkyl, —C$_{(1-4)}$alkyl-OH, —C$_{(1-4)}$alkyl-OCH$_3$, —C(O)C$_{(1-4)}$alkyl-OH, —C(O)C$_{(1-4)}$alkyl-OCH$_3$, dialkylamino, or alkylamino; provided that the same $R_5$ substituent is not present more than once, unless said $R_5$ substituent is halogen, hydroxyl, alkoxy, or alkyl;

$R_{bb}$ is hydrogen, halogen, alkoxy, dialkylamino, phenyl optionally substituted with $R_6$, heteroaryl optionally substituted with $R_6$ (wherein said heteroaryl is preferably pyrrolyl, furanyl, thiophenyl, imidazolyl, thiazolyl, oxazolyl, pyranyl, thiopyranyl, pyridinyl, pyrimidinyl, triazolyl, pyrazinyl, pyridinyl-N-oxide, or pyrrolyl-N-oxide, and most preferably pyrrolyl, furanyl, thiophenyl, imidazolyl, thiazolyl, oxazolyl, pyridinyl, pyrimidinyl, triazolyl, or pyrazinyl), piperazinyl-2-one optionally substituted with $R_6$, imidazolidinyl-2-one optionally substituted with $R_6$, oxazolidinyl-2-one optionally substituted with $R_6$, or heterocyclyl optionally substituted with $R_6$ (wherein said heterocyclyl is preferably azepanyl, diazepanyl, azetidinyl, pyrrolidinyl, tetrahydrofuranyl, tetrahydrothiophenyl, imidazolidinyl, thiazolidinyl, oxazolidinyl, tetrahydropyranyl, tetrahydrothiopyranyl, piperidinyl, thiomorpholinyl, thiomorpholinyl 1,1-dioxide, morpholinyl or piperazinyl);

$R_6$ is one, two, or three substituents independently selected from: halogen, cyano, trifluoromethyl, amino, hydroxyl, heteroaryl, alkoxy, —C(O)alkyl, —SO$_2$alkyl, —C(O)NH(alkyl), —C(O)N(alkyl)$_2$, —C(O)C$_{(1-4)}$alkyl-N(alkyl)$_2$, alkyl, —C$_{(1-4)}$alkyl-OH, —C$_{(1-4)}$alkyl-OCH$_3$, —C(O)C$_{(1-4)}$alkyl-OH, —C(O)C$_{(1-4)}$alkyl-OCH$_3$, dialkylamino, or alkylamino; provided that the same $R_6$ substituent is not present more than once, unless said $R_6$ substituent is halogen, hydroxyl, alkoxy, or alkyl;

$R_c$ is heterocyclyl optionally substituted with $R_7$ (wherein said heterocyclyl is preferably azepanyl, diazepanyl, azetidinyl, pyrrolidinyl, tetrahydrofuranyl, tetrahydrothiophenyl, imidazolidinyl, thiazolidinyl, oxazolidinyl, tetrahydropyranyl, tetrahydrothiopyranyl, piperidinyl, thiomorpholinyl, thiomorpholinyl 1,1-dioxide, morpholinyl, or piperazinyl), or heteroaryl (wherein said heteroaryl is preferably pyrrolyl, furanyl, thiophenyl, imidazolyl, thiazolyl, oxazolyl, pyridinyl, pyrimidinyl, or pyrazinyl); and $R_7$ is one, two, or three substituents independently selected from: halogen, cyano, trifluoromethyl, amino, hydroxyl, heteroaryl, alkoxy, —C(O)alkyl, —SO$_2$alkyl, —C(O)NH(alkyl), —C(O)N(alkyl)$_2$, —C(O)C$_{(1-4)}$alkyl-N(alkyl)$_2$, alkyl, —C$_{(1-4)}$alkyl-OH, —C$_{(1-4)}$alkyl-OCH$_3$, —C(O)C$_{(1-4)}$alkyl-OH, —C(O)C$_{(1-4)}$alkyl-OCH$_3$, dialkylamino, or alkylamino; provided that the same $R_7$ substituent is not present more than once, unless said $R_7$ substituent is halogen, hydroxyl, alkoxy, or alkyl;

$R_3$ is one or more substituents independently selected from: hydrogen provided that $R_{bb}$ is not hydrogen, alkyl, alkoxy, halogen, amino optionally substituted with $R_4$, C$_{1-2}$(alkyl)-OH, nitro, cycloalkyl optionally substituted with $R_4$ (wherein said cycloalkyl is preferably cyclopentanyl or cyclohexanyl), heteroaryl optionally substituted with $R_4$ (wherein said heteroaryl is preferably pyrrolyl, furanyl, thiophenyl, imidazolyl, thiazolyl, oxazolyl, pyranyl, thiopyranyl, pyridinyl, pyrimidinyl, triazolyl, pyrazinyl, pyridinyl-N-oxide, or pyrrolyl-N-oxide; and most preferably pyrrolyl, furanyl, thiophenyl, imidazolyl, thiazolyl, oxazolyl, pyridinyl, pyrimidinyl, triazolyl, or pyrazinyl), alkylamino, heterocyclyl optionally substituted with $R_4$ (wherein said heterocyclyl is preferably tetrahydropyridinyl, tetrahydropyrazinyl, dihydrofuranyl, dihydrooxazinyl, dihydropyrrolyl, dihydroimidazolyl azepenyl, pyrrolidinyl, tetrahydrofuranyl, tetrahydrothiophenyl, imidazolidinyl, thiazolidinyl, oxazolidinyl, tetrahydropyranyl, tetrahydrothiopyranyl, piperidinyl, thiomorpholinyl, morpholinyl or piperazinyl), alkoxyether, —O(cycloalkyl), pyrrolidinonyl optionally substituted with $R_4$, phenoxy optionally substituted with $R_4$, —CN, —OCHF$_2$, —OCF$_3$, —CF$_3$, halogenated alkyl, heteroaryloxy optionally substituted with $R_4$, dialkylamino, —NHSO$_2$alkyl, or —SO$_2$alkyl; wherein $R_4$ is independently selected from: halogen, cyano, trifluoromethyl, amino, hydroxyl, alkoxy, —C(O)alkyl, —CO$_2$alkyl, —SO$_2$alkyl, —C(O)N(alkyl)$_2$, alkyl, or alkylamino.

Illustrative methods of using the Compounds of Formula C to make compounds of Formula I are shown in Schemes 1-10 below.

The compounds of Formula I, wherein X, B, G, Q, Z, $R_1$, $R_2$, and $R_3$ are as defined in Formula I, may be synthesized as outlined by the general synthetic route illustrated in Scheme 1. Reaction of piperidine C with an appropriate acylating/alkylating reagent VI, wherein LG may be an appropriate leaving group such as Br, Cl, I, imidazolyl, or p-nitrophenoxy, provides the desired product I. These reactions are generally performed in the presence of a solvent, such as methylene chloride, and a base, such as diisopropylethylamine, at a temperature of 0° C. to 150° C., preferably from 0° C.-25° C. The acylating reagents VI are either commercially available or, wherein Q is a direct bond and Z is NH or N(alkyl), can be prepared as illustrated in Scheme 1. Treatment of an appropriate R$_3$BZH, wherein Z is NH or N(alkyl ), with an appropriate acylating reagent such as carbonyldiimidazole, thiophosgene, or p-nitrophenylchloroformate in the presence of a base such as triethylamine can provide VI. Many R$_3$BZH Scheme 1

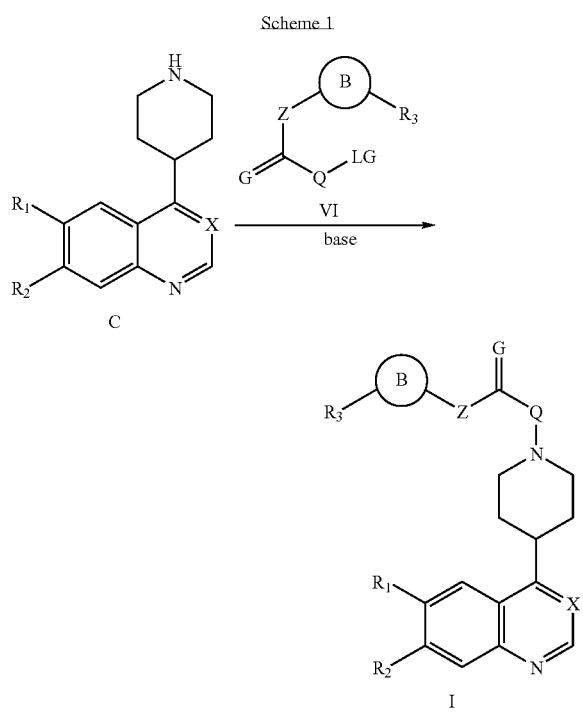

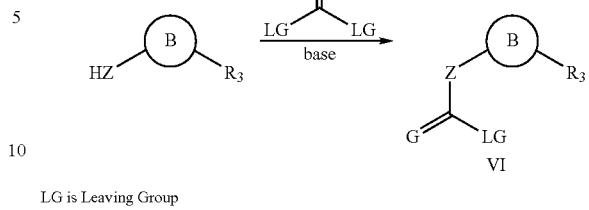

LG is Leaving Group

The compounds of Formula I, wherein Q is a direct bond, Z is NH or N(alkyl), and G, X, $R_1$, $R_2$, and $R_3$ are defined as in Formula I, can be prepared by the reaction sequence outlined in Scheme 2. Treatment of piperidine C, prepared by the method outlined in Scheme 11, with an acylating agent such as phosgene, thiophosgene, or carbonyldiimidazole, wherein LG is Cl or imidazole, and an organic base such as diisopropylethylamine can provide intermediate XI, which upon treatment with an appropriate $R_3BZH$ can provide the final compound I. Alternatively compound I, wherein Z is NH, can be obtained via direct treatment of piperidine C with an appropriate isocyanate or isothiocyanate ($R_3$—B—N=C=G). The isocyanates are either commercially available or can be prepared by a known method (*J. Org Chem*, 1985, 50, 5879-5881).

Scheme 2

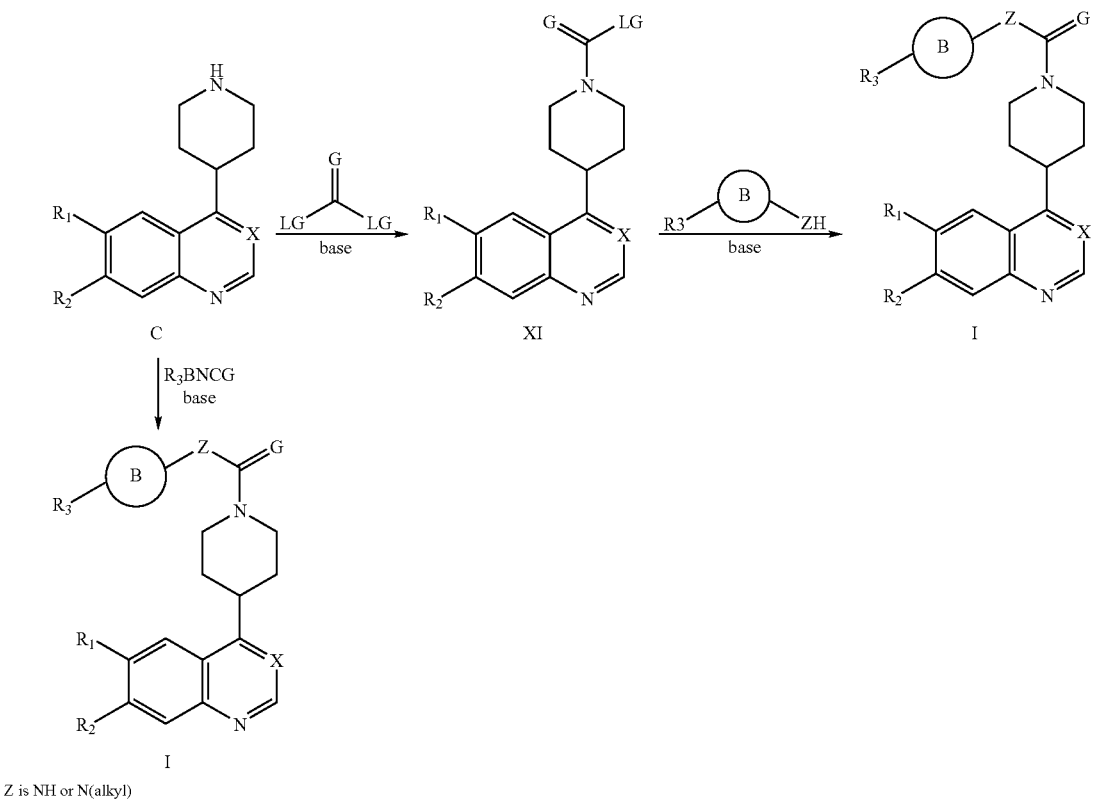

Z is NH or N(alkyl)
LG is Leaving Group

The compounds of Formula I, where Q is a direct bond, B is phenyl or heteroaryl, G is O, Z is NH or N(alkyl), $R_3$ is phenyl or heteroaryl, and X, $R_1$, and $R_2$ are defined as in Formula I, can be prepared by the reaction sequence outlined in Scheme 3. Treatment of a piperidine C, which can be prepared as described in Scheme 11, with an appropriate iodoarylamide acylating agent XII, wherein LG is an appropriate leaving group, for instance, bromide, chloride, or p-nitrophenoxide, can provide the iodoaryl XIII. Reaction of iodoaryl XIII with an appropriate aryl boronic acid or aryl boronic ester (R is H or alkyl) in the presence of a palladium catalyst such as bis(triphenylphosphine)palladium dichloride in a solvent such as toluene at a temperature of 50° C. to 200° C. can provide the final product I. The iodoaryl acylating agents are either commercially available or prepared as outlined in Scheme 1 while the boronic acids/boronic esters are either commercially available or prepared by known methods (*Synthesis* 2003, 4, 469-483; *Organic letters* 2001, 3, 1435-1437).

Compounds of Formula I, wherein $R_1$ is $-CC(CH_2)_nR_a$, G is O, and X, B, Q, Z, $R_a$, $R_2$, and $R_3$ are defined as in Formula I, can be prepared by the sequence outlined in Scheme 4. Treatment of the appropriate iodo substituted piperidine C, which can be prepared as described in Scheme 11, with an appropriate reagent VI can provide the iodoaryl intermediate XVI. Reaction of XVI with an appropriate alkynyl alcohol in the presence of a palladium catalyst such as bis(triphenylphosphine)palladium dichloride, a copper catalyst such as copper(I) iodide, a base such as diethyl amine and a solvent such as dimethylformamide at a temperature of 25° C. to 150° C. can provide the alkynyl alcohol XVII. Conversion of the alcohol XVII to an appropriate leaving group known by those skilled in the art such as a mesylate followed by an $SN_2$ displacement reaction of XVIII with an appropriate nucleophilic heterocycle, heteroaryl, amine, alcohol, sulfonamide, or thiol can provide the final compound I. If $R_a$ nucleophile is a thiol, further oxidation of the thiol can provide the corresponding sulfoxides and sulfones. If $R_a$ nucleophile is an amino, acylation of the nitrogen with an appropriate acylating or sulfonylating agent can provide the corresponding amides, carbamates, ureas, and sulfonamides. If the desired $R_a$ is $COOR_y$ or $CONR_wR_x$, these can be derived from the corresponding hydroxyl group. Oxidation of the hydroxyl group to the acid followed by ester or amide formation under conditions known in the art can provide examples wherein $R_a$ is $COOR_y$ or $CONR_wR_x$. One could prepare the compounds where $R_2$ is $-CC(CH_2)_nR_a$ utilizing the same reaction sequence with the appropriate 7-iodoaryl quinazoline or quinoline.

Scheme 3

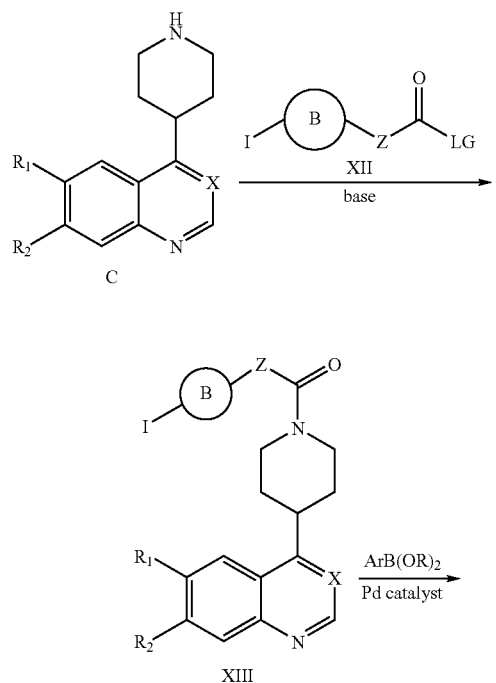

Z is NH or N(alkyl)
LG is Leaving Group
Ar is aryl or heteroaryl
R is H or alkyl Scheme 4

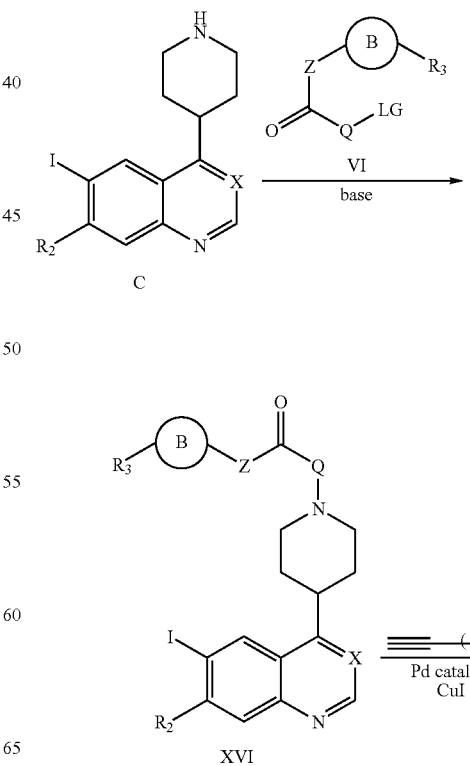

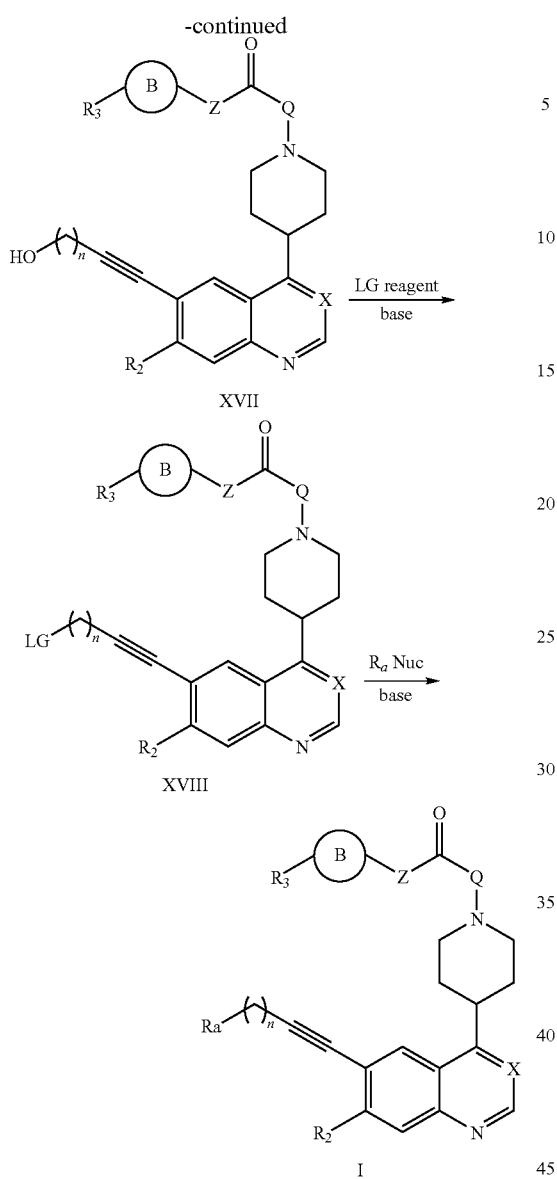

LG is Leaving Group
Nuc is a nucleophile

Compounds of Formula I, wherein $R_1$ is phenyl or heteroaryl, G is O, and X, B, Q, Z, $R_2$, and $R_3$ are defined as in Formula I, can also be prepared as outlined in Scheme 5. Treatment of compound XIX (an example of Formula C, wherein $R_1$ is iodine), which can be prepared by decarboxylation of previously described compound IV, with an appropriate aryl boronic acid or aryl boronic ester (R is H or alkyl) in the presence of a palladium catalyst such as bis(triphenylphosphine)palladium dichloride in a solvent such as toluene at a temperature of 50° C. to 200° C. can provide aryl intermediate XX. Deprotection of the amine protecting group known to those skilled in the art under standard conditions can provide the piperidine XXI, which can then be acylated or alkylated using reagent VI to provide the final compound I. The boronic acids/boronic esters are either commercially available or prepared by known methods (*Synthesis* 2003, 4, 469-483; *Organic letters* 2001, 3, 1435-1437). One could prepare the compounds where $R_2$ is phenyl or heteroaryl utilizing the same reaction sequence with the appropriate 7-iodo quinazoline or quinoline.

Scheme 5

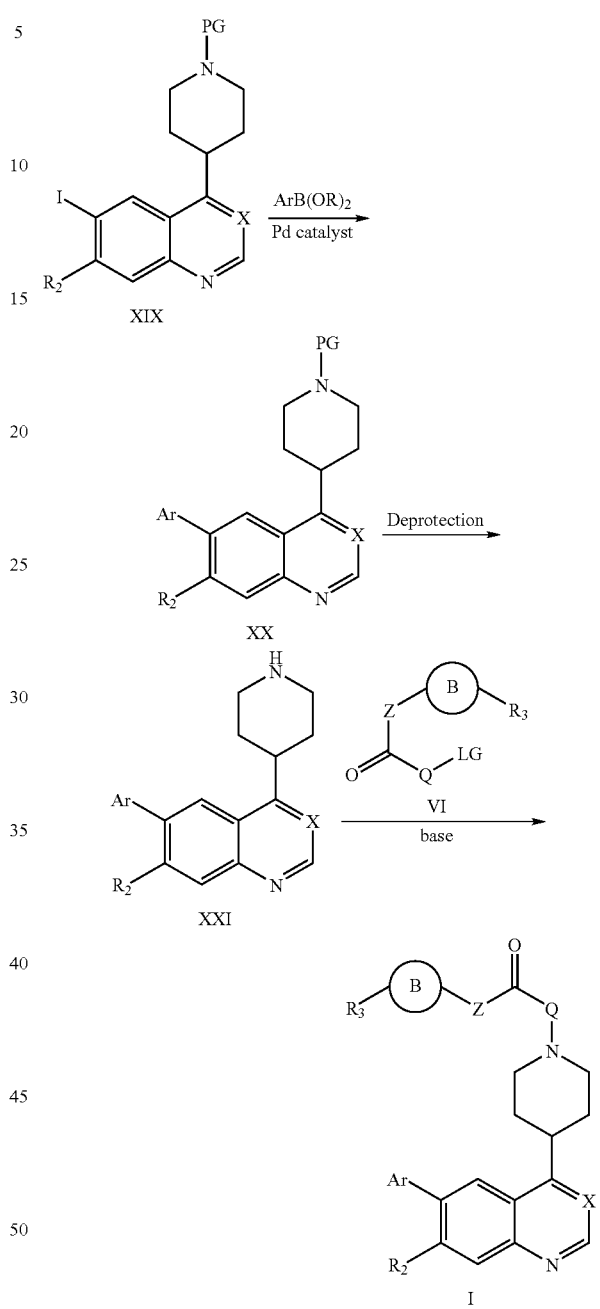

LG is Leaving Group
Ar is aryl or heteroaryl
R is H or alkyl

Compounds of formula I, wherein $R_1$ is —CHCH(CH$_2$)$_n$R$_a$, G is O, and X, B, Q, Z, $R_a$, $R_2$, and $R_3$ are defined as in Formula I, can be prepared by the sequence outlined in Scheme 6. Treatment of the appropriate iodo substituted piperidine C, which can be prepared as described in Scheme 11, with an appropriate reagent VI can provide the iodoaryl intermediate XVI. Reaction of XVI with an appropriate vinylstannane XXII in the presence of a palladium catalyst such as bis(triphenylphosphine)palladium dichloride and a solvent such as dimethylformamide at a temperature of 25° C. to 150° C. can provide the alkenyl alcohol XXIII. Conversion of the alcohol XXIII to an appropriate leaving group known by those skilled in the art such as a mesylate followed by an $SN_2$ displacement reaction of XXIV with an appropriate nucleophilic heterocycle, heteroaryl, amine, alcohol, sulfonamide, or thiol can provide the final compound I. If $R_a$ nucleophile is a thiol, further oxidation of the thiol can provide the corresponding sulfoxides and sulfones. If $R_a$ nucleophile is an amino, acylation of the nitrogen with an appropriate acylating or sulfonylating agent can provide the corresponding amides, carbamates, ureas, and sulfonamides. If the desired $R_a$ is $COOR_y$ or $CONR_wR_x$, these can be derived from the corresponding hydroxyl group. Oxidation of the hydroxyl group to the acid followed by ester or amide formation under conditions known in the art can provide examples wherein $R_a$ is $COOR_y$ or $CONR_wR_x$. The corresponding cis olefin isomers of Formula I can be prepared by the same method utilizing the appropriate cis vinyl stannane. Reduction of the olefin moiety under known conditions can provide the saturated compounds where $R_1$ is —$CH_2CH_2(CH_2)_nR_a$. One could prepare the compounds where $R_2$ is —CHCH $(CH_2)_nR_a$ utilizing the same reaction sequence with the appropriate 7-iodo quinazoline or quinoline.

Scheme 6

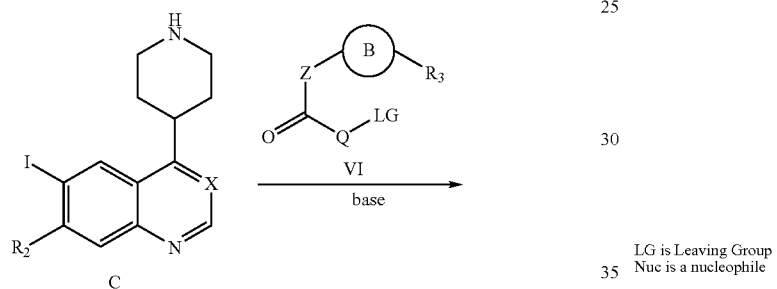

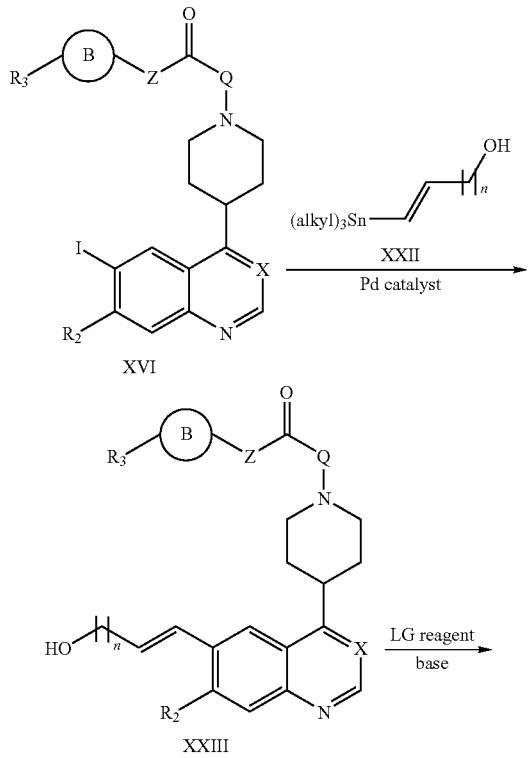

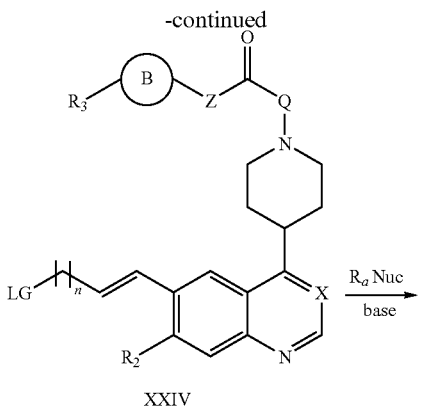

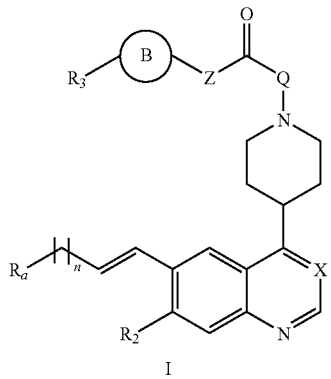

LG is Leaving Group
Nuc is a nucleophile

Compounds of formula I wherein $R_2$ is —$Y(CH_2)_nR_a$, Y is O, S, NH, or N(alkyl), G is O, and X, B, Q, Z, $R_a$, $R_1$, and $R_3$ are defined as in Formula I, can be prepared by the sequence outlined in Scheme 7. Treatment of compound XXV (a compound of Formula C, wherein $R_2$ is halogen), which can be prepared as described in Scheme 11, with a base such as hydroxide ion or potassium t-butoxide in the presence of a suitable $R_a(CH_2)_nYH$ at a temperature of 25° C. to 150° C. in a solvent such as THF can provide the substituted XXVI. Deprotection of the amine protecting group known to those skilled in the art under standard conditions can provide the piperidine XXVII, which can then be acylated or alkylated using reagent VI to provide the final compound I. One could prepare the compounds where $R_1$ is —$Y(CH_2)_nR_a$ utilizing the same reaction sequence with the appropriate 6-halogenated substituted quinazoline or quinoline. A related synthetic route to intermediate quinazoline/quinoline XXVI is also outlined in Scheme 7. Treatment of compound IV, which can be prepared as described in Scheme 11, with a base such as KOH in the presence of a suitable $R_a(CH_2)_nYH$ at a temperature of 25° C. to 150° C. in a solvent mixture such as dioxane/water, can provide the substituted intermediate XXVI. Compounds of formula I where $R_2$ is —$OR_c$ or $R_{bb}$ can be prepared by the same reaction sequence outlined in Scheme 7 using an appropriate —$OR_c$ or $R_{bb}$ in the SnAr step.

Scheme 7

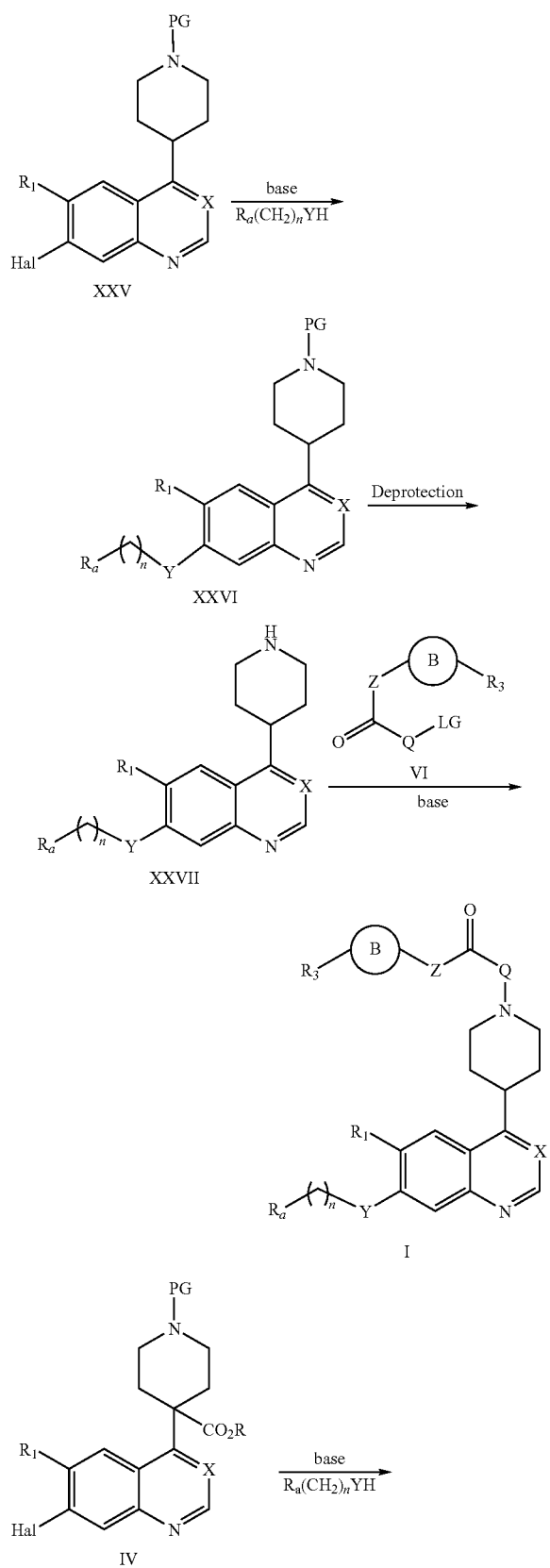

Hal is Cl or F
PG is Protecting Group
LG is Leaving Group

An alternative method to prepare compounds of Formula I, wherein $R_2$ is $-Y(CH_2)_n R_a$, Y is O, S, NH, or N(alkyl), G is O, and X, B, Q, Z, $R_a$, $R_1$, and $R_3$ are defined as in Formula I, can be prepared by the sequence outlined in Scheme 8. Treatment of compound XXV, which can be prepared as described in Scheme 11, with a base such as hydroxide ion or potassium t-butoxide in the presence of a suitable $PG_1O(CH_2)_n YH$, where $PG_1$ is an appropriate alcohol protecting group, at a temperature of 25° C. to 150° C. in a solvent such as THF can provide the substituted XXVIII. Deprotection of the $PG_1$ group known to those skilled in the art under standard conditions can provide intermediate XXIX. Conversion of the alcohol XXIX to an appropriate leaving group known by those skilled in the art such as a mesylate followed by an $SN_2$ displacement reaction of XXX with an appropriate nucleophilic heterocycle, heteroaryl, amine, alcohol, sulfonamide, or thiol can provide compound XXXI. If $R_a$ nucleophile is a thiol, further oxidation of the thiol can provide the corresponding sulfoxides and sulfones. If $R_a$ nucleophile is an amino, acylation of the nitrogen with an appropriate acylating or sulfonylating agent can provide the corresponding amides, carbamates, ureas, and sulfonamides. If the desired $R_a$ is $COOR_y$ or $CONR_w R_x$, these can be derived from the corresponding hydroxyl group. Oxidation of the hydroxyl group to the acid followed by ester or amide formation under conditions known in the art can provide examples wherein $R_a$ is $COOR_y$ or $CONR_w R_x$. Deprotection of the amine protecting group known to those skilled in the art under standard conditions can provide the piperidine XXXII, which can then be acylated or alkylated using reagent VI to provide the final compound I. One could prepare the compounds where $R_1$ is $-Y(CH_2)_n R_a$ utilizing the same reaction sequence with the appropriate 6-halogenated substituted quinazoline or quinoline.

Scheme 8

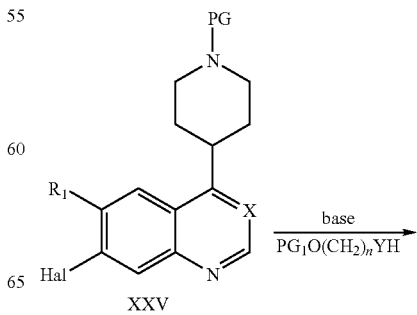

-continued

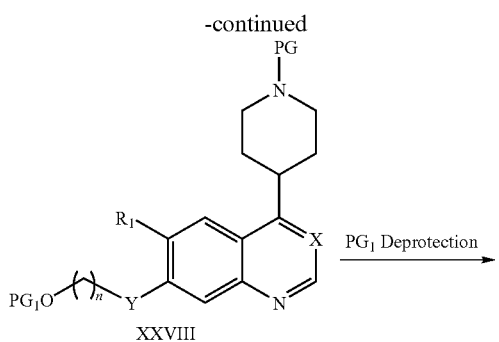

XXVIII

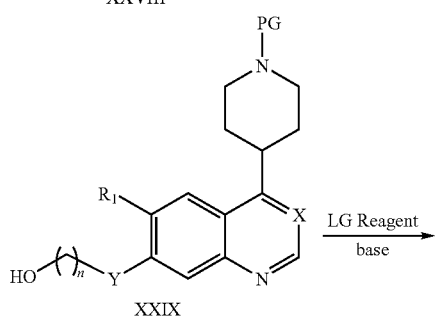

XXIX

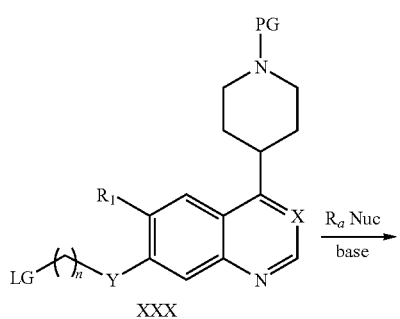

XXX

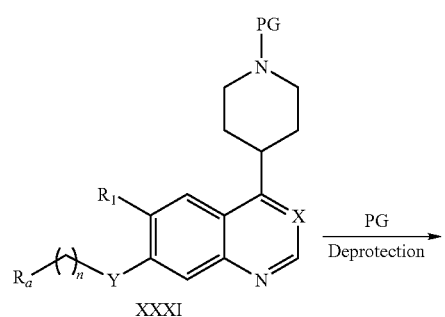

XXXI

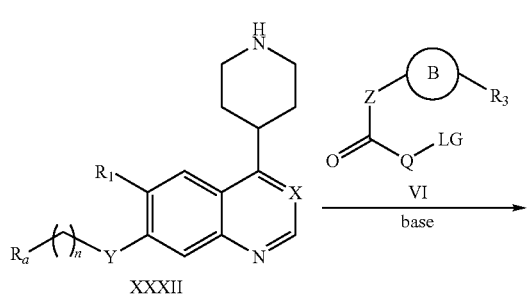

XXXII

-continued

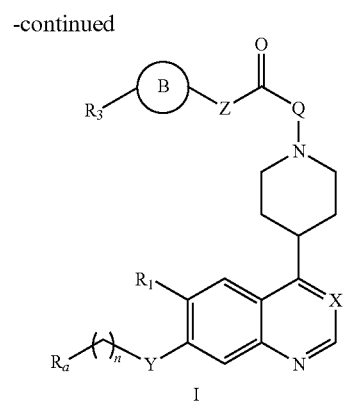

I

Hal is Cl or F
PG and PG₁ are Protecting Groups
LG is Leaving Group

An alternative method to prepare compounds of Formula I, wherein $R_2$ is —Y(CH$_2$)$_n$R$_a$, Y is O, S, NH, or N(alkyl), G is O, and X, B, Q, Z, $R_a$, $R_1$, and $R_3$ are defined as in Formula I, can be prepared by the sequence outlined in Scheme 9. Removal of the amine protecting group known to those skilled in the art under standard conditions of compound XXV, which can be prepared as described in Scheme 11, can provide the piperidine XXXIII, which can then be acylated or alkylated using reagent VI to provide compound XXXIV. Treatment of XXXIV with a base such as hydroxide ion or potassium t-butoxide in the presence of a suitable $R_a$(CH$_2$)$_n$YH at a temperature of 25° C. to 150° C. in a solvent such as THF can provide the final compound I. One could prepare the compounds where $R_1$ is —Y(CH$_2$)$_n$R$_a$ utilizing the same reaction sequence with the appropriate 6-halogenated substituted quinazoline or quinoline.

Scheme 9

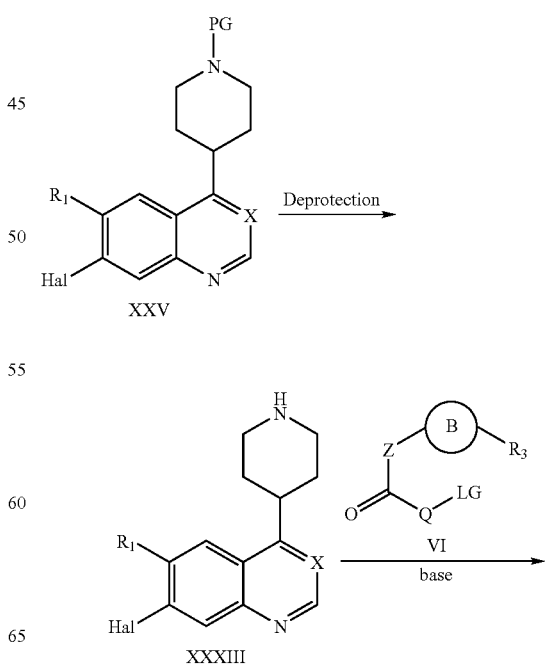

XXV

XXXIII

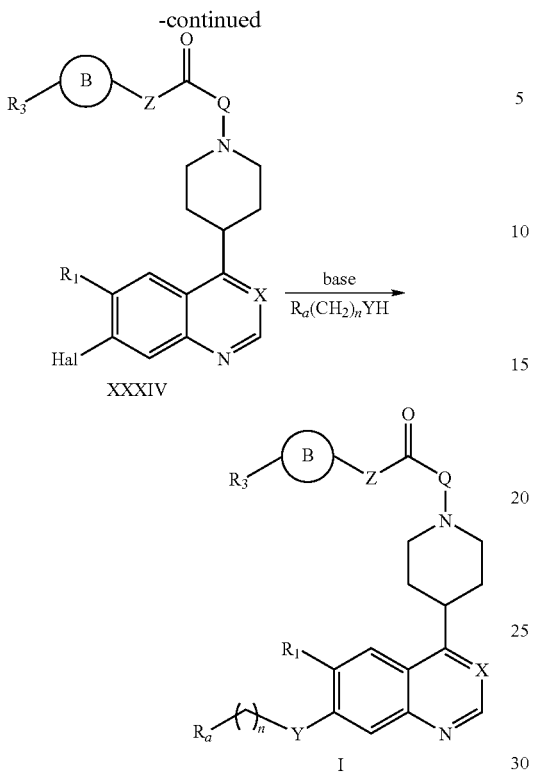

Hal is Cl or F
PG is Protecting Group
LG is Leaving Group

Compounds of formula I wherein $R_1$ and $R_2$ are —Y(CH$_2$)$_n$R$_a$, Y is O, S, NH, or N(alkyl), G is O, and X, B, Q, Z, R$_a$, and R$_3$ are defined as in Formula I, can be prepared by the sequence outlined in Scheme 10. Treatment of compound XXXV (a compound of Formula C, wherein both $R_1$ and $R_2$ are halogen), which can be prepared as described in Scheme 11, with a base such as hydroxide ion or potassium t-butoxide in the presence of a suitable R$_a$(CH$_2$)$_n$YH at a temperature of 25° C. to 150° C. in a solvent such as THF can provide the substituted XXXVI. A subsequent SnAr reaction of compound XXXVI with a base such as hydroxide ion or potassium t-butoxide in the presence of another R$_a$(CH$_2$)$_n$YH at a temperature of 25° C. to 150° C. in a solvent such as DMSO can provide the substituted XXXVII. Deprotection of the amine protecting group known to those skilled in the art under standard conditions can provide the piperidine XXXVIII, which can then be acylated or alkylated using reagent VI to provide the final compound I. One could also prepare compounds where $R_1$ is —OR$_c$ or with an appropriate R$_{bb}$ such as alkoxy using the same reaction sequence in Scheme 10.

Scheme 10

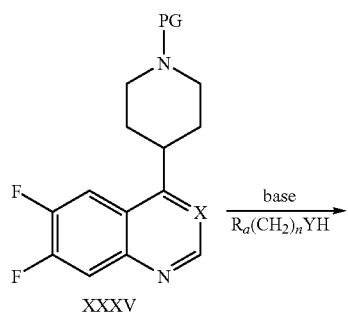

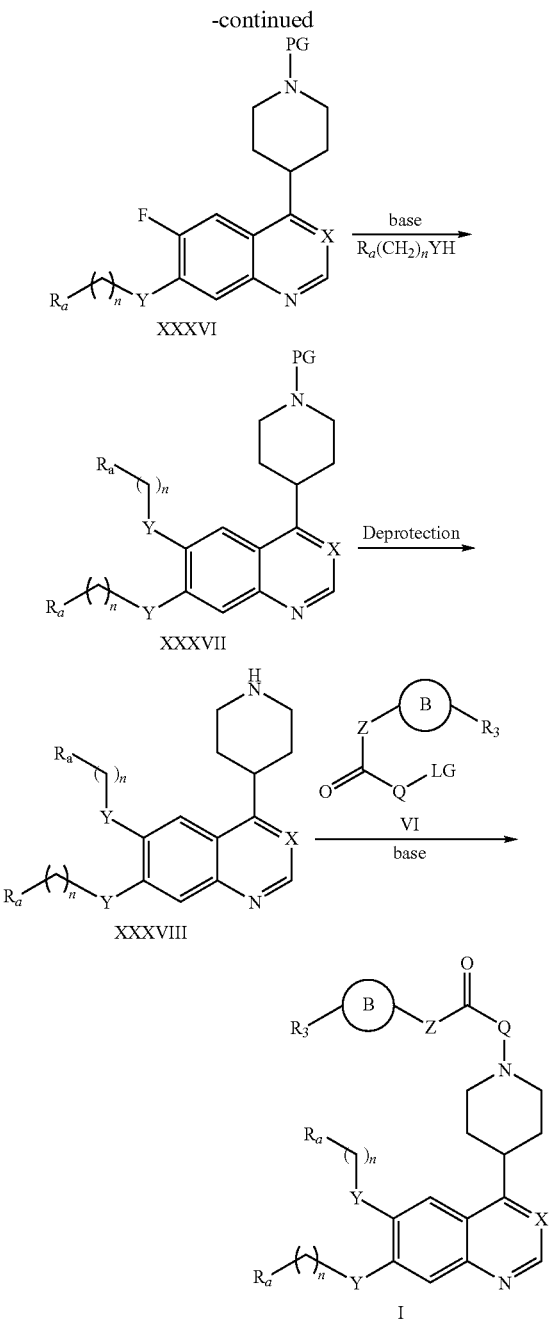

PG is Protecting Group

Preparation of the Compounds of the Present Invention

During any of the processes for preparation of the compounds of the present invention, it may be necessary and/or desirable to protect sensitive or reactive groups on any of the molecules concerned. This may be achieved by means of conventional protecting groups, such as those described in *Protecting Groups*, P. Kocienski, Thieme Medical Publishers, 2000; and T. W. Greene & P. G. M. Wuts, *Protective Groups in Organic Synthesis*, 3$^{rd}$ ed. Wiley Interscience, 1999. The protecting groups may be removed at a convenient subsequent stage using methods known in the art.

General Reaction Scheme

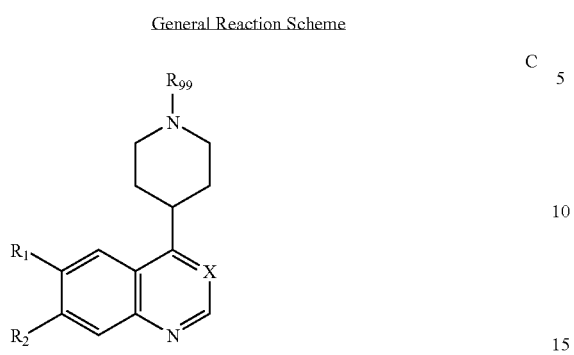

Compounds of Formula C can be prepared by methods known to those who are skilled in the art. The following reaction schemes are only meant to represent examples of the invention and are in no way meant to be a limit of the invention.

The compounds of Formula C, wherein X, $R_1$, $R_2$, and $R_{99}$ are as defined in Formula C, may be synthesized as outlined by the general synthetic route illustrated in Scheme 11. In the first step, treatment of a piperidinyl ester II with a strong base such as lithium hexamethyldisilazide in solvent such as tetrahydrofuran (THF) followed by addition of an appropriate chloroquinazoline/quinoline III at a temperature of −78° C. to 25° C. can provide the substituted piperidine IV. Treatment of IV to decarboxylation conditions, such as LiCl in DMSO/$H_2O$ at a temperature of 100° C. to 200° C. or KOH in MeOH at a temperature of 25° C. to 200° C., followed by deprotection of the amine protecting group (PG) under standard conditions known to those skilled in the art can provide piperidine C.

Scheme 11

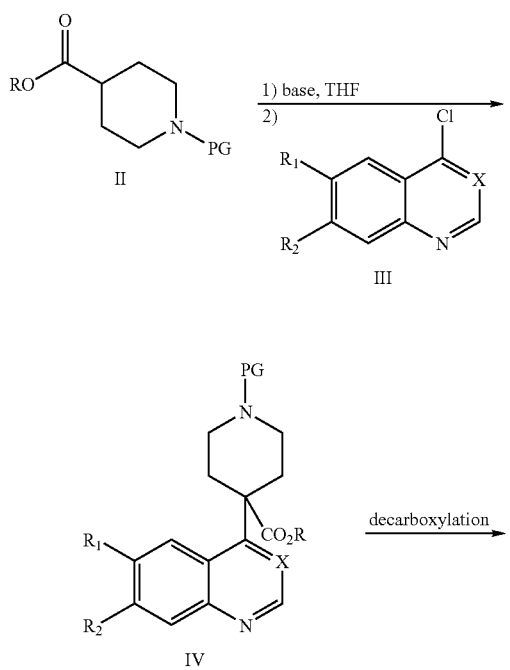

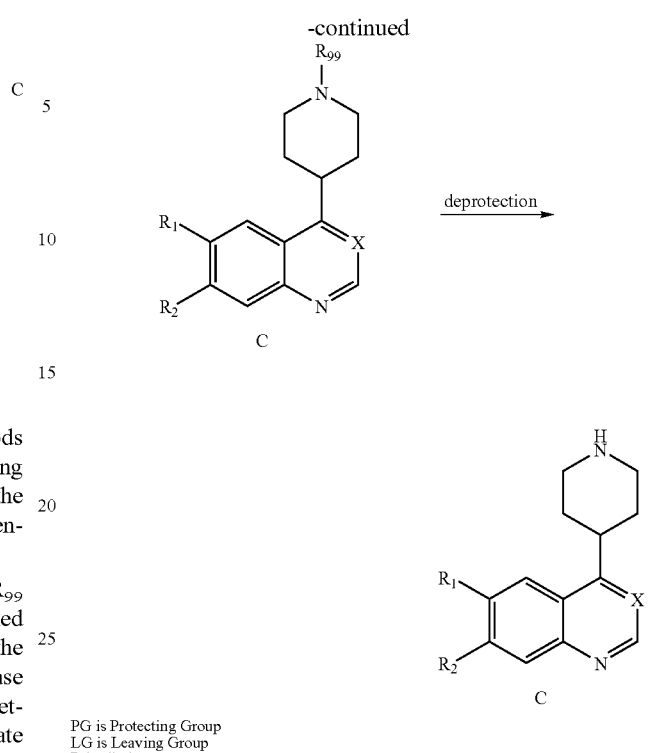

PG is Protecting Group
LG is Leaving Group
R is alkyl

An alternative method to prepare the piperidine intermediate V, wherein X is N and $R_1$ and $R_2$ are defined as in Formula C, is illustrated in Scheme 12. Treatment of isonipecotic acid with an appropriate amino protecting group can provide the N-protected piperidine VII. Transformation of the carboxylic acid to the primary amide and subsequent dehydration under standard conditions can provide the cyano piperidine VIII. Treatment of piperidine VIII with an appropriate aniline IX utilizing a Friedel Crafts reaction with a Lewis acid, such as $BF_3 \cdot Et_2O$, can provide the substituted aniline X. Formation of the quinazoline ring can be accomplished by treating aniline X with a reagent such as formamide at a temperature of 100° C. to 200° C. and subsequent deprotection of the amino protecting group under standard conditions can provide the desired piperidine C.

Scheme 12

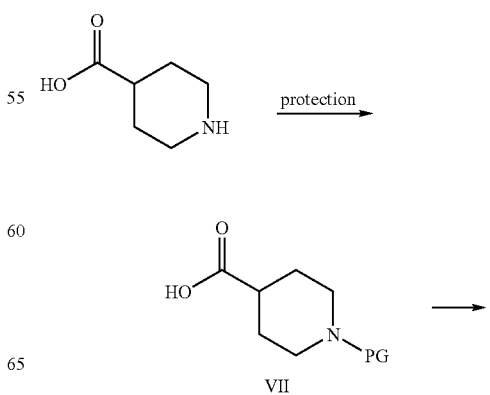

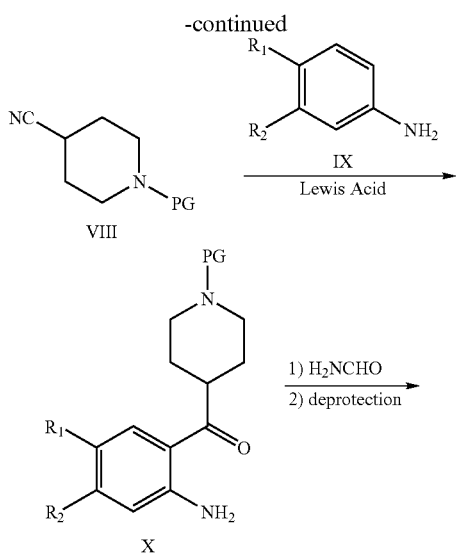

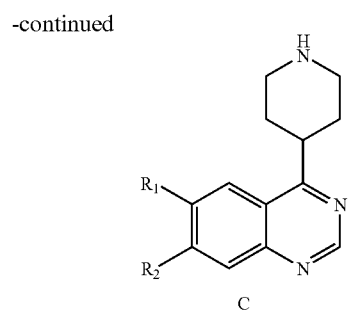

PG is Protecting Group

Representative Compounds

Representative compounds of the present invention synthesized by the aforementioned methods are presented below. Examples of the synthesis of specific compounds are presented thereafter. Preferred compounds are numbers 11, 14, 55, 58, 60, 69, 73, 92, and 93; particularly preferred are numbers 11, 14, 58, 69, and 92.

| Example No. | Name | Structure |
|---|---|---|
| 2 | 6-Iodo-4-piperidin-4-yl-quinazoline | 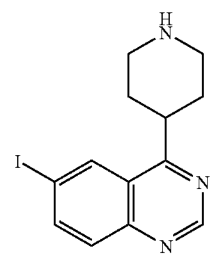 |
| 3 | 4-(7-chloro-quinazolin-4-yl)-piperidine | 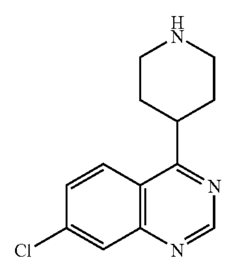 |
| 4 | 4-(7-methoxy-quinazolin-4-yl)-piperidine | 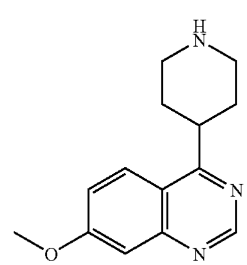 |

-continued
| Example No. | Name | Structure |
|---|---|---|
| 5 | 4-Piperidin-4-yl-7-(3-piperidin-1-yl-propoxy)-quinazoline | 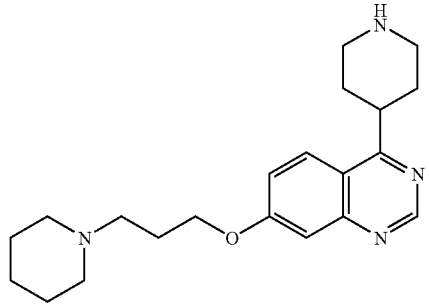 |
| 6 | 4-Piperidin-4-yl-7-(2-piperidin-1-yl-ethoxy)-quinazoline | 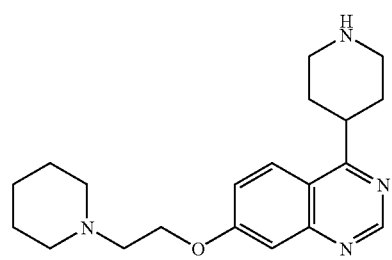 |
| 7 | Diethyl-[2-(4-piperidin-4-yl-quinazolin-7-yloxy)-ethyl]-amine | 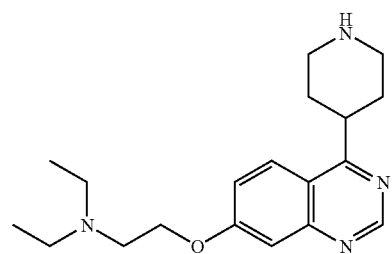 |
| 8 | Diethyl-[3-(4-piperidin-4-yl-quinazolin-7-yloxy)-propyl]-amine | 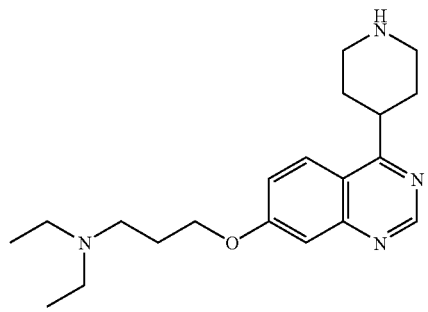 |
| 9 | 7-(2-Morpholin-4-yl-ethoxy)-4-piperidin-4-yl-quinazoline | 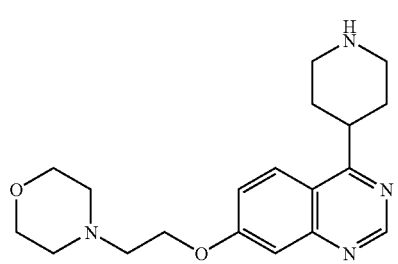 |

-continued
| Example No. | Name | Structure |
|---|---|---|
| 10 | 7-(3-Morpholin-4-yl-propoxy)-4-piperidin-4-yl-quinazoline | 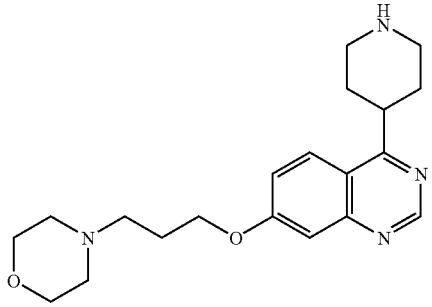 |
| 11 | 7-[3-(4-Methyl-piperazin-1-yl)-propoxy]-4-piperidin-4-yl-quinazoline | 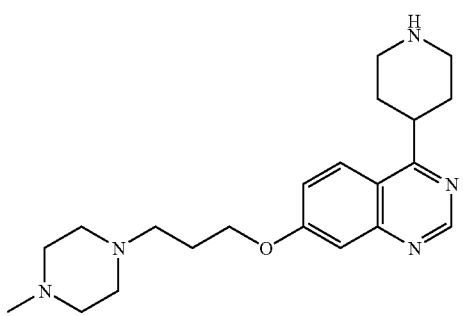 |
| 12 | 4-[7-(3-Methanesulfonylamino-propoxy)-quinazolin-4-yl]-piperidine-1-carboxylic acid tert-butyl ester | 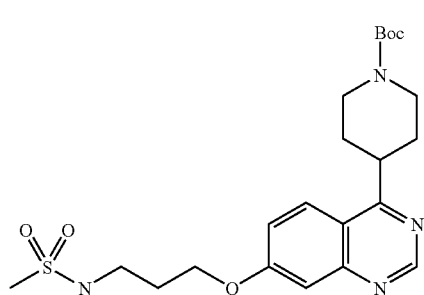 |
| 13 | 4-{7-[3-(2-Oxo-pyrrolidin-1-yl)-propoxy]-quinazolin-4-yl}-piperidine-1-carboxylic acid tert-butyl ester | 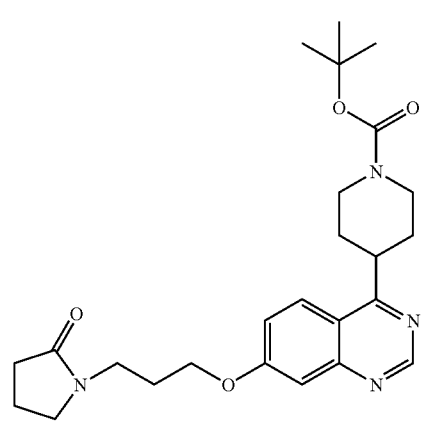 |

-continued

| Example No. | Name | Structure |
|---|---|---|
| 14 | 1-[2-(4-Piperidin-4-yl-quinazolin-7-yloxy)-ethyl]-pyrrolidin-2-one | 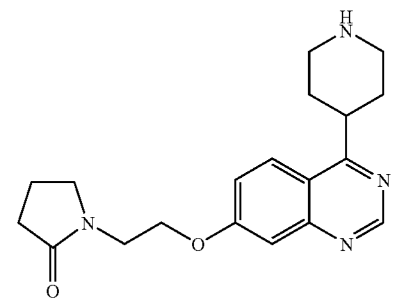 |
| 15 | 6-[3-(4-Methyl-piperazin-1-yl)-propoxy]-4-piperidin-4-yl-quinazoline | 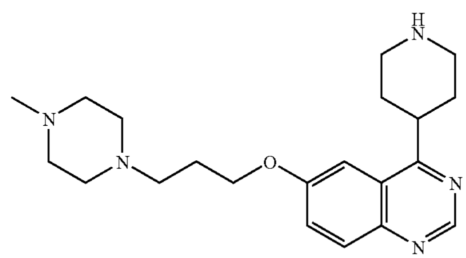 |
| 16 | 3-(4-Piperidin-4-yl-quinazolin-7-yloxy)-propan-1-ol | 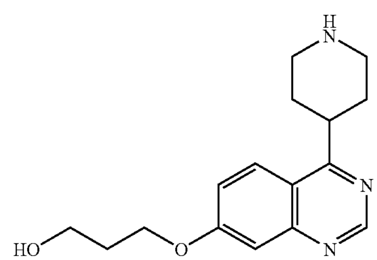 |
| 17 | 7-(3-Methoxy-propoxy)-4-piperidin-4-yl-quinazoline | 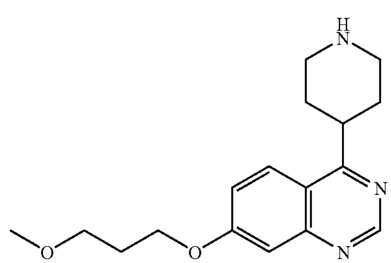 |
| 18 | 3-[2-(4-Piperidin-4-yl-quinazolin-7-yloxy)-ethyl]-oxazolidin-2-one | 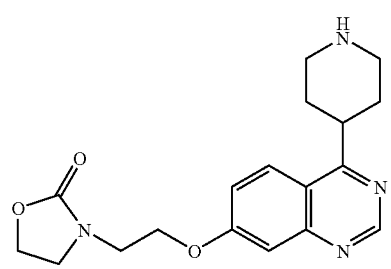 |

-continued

| Example No. | Name | Structure |
|---|---|---|
| 19 | 7-(1-Methyl-piperidin-4-ylmethoxy)-4-piperidin-4-yl-quinazoline | 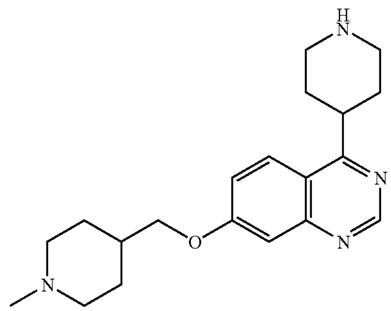 |
| 20 | 1-{4-[2-(4-Piperidin-4-yl-quinazolin-7-yloxy)-ethyl]-piperazin-1-yl}-ethanone | 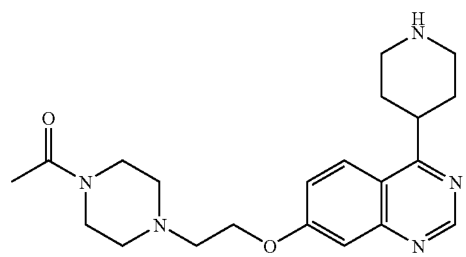 |
| 21 | 1-[3-(4-Piperidin-4-yl-quinazolin-6-yloxy)-propyl]-pyrrolidin-2-one | 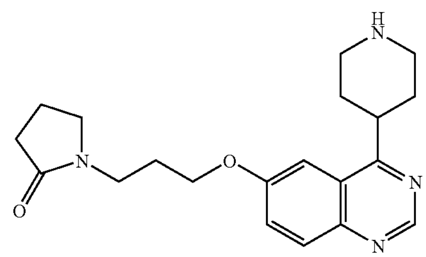 |
| 22 | [3-(4-Methyl-piperazin-1-yl)-propyl]-(4-piperidin-4-yl-quinazolin-7-yl)-amine | 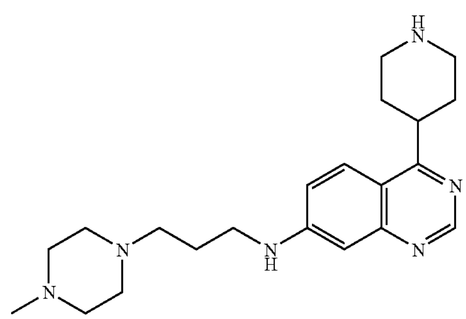 |
| 23 | 7-(4-Methyl-piperazin-1-yl)-4-piperidin-4-yl-quinazoline | 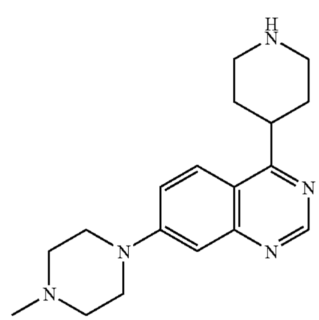 |

-continued

| Example No. | Name | Structure |
|---|---|---|
| 24 | 4-[7-(3-[1,2,4]Triazol-4-yl-propoxy)-quinazolin-4-yl]-piperidine-1-carboxylic acid tert-butyl ester | 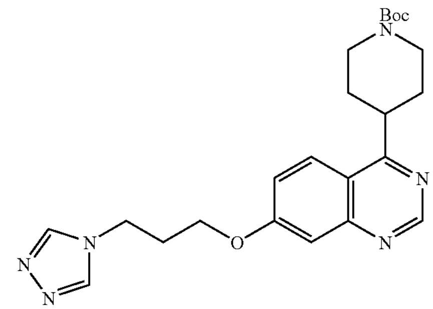 |
| 25 | 3-Dimethylamino-4-[3-(4-piperidin-4-yl-quinazolin-7-yloxy)-propylamino]-cyclobut-3-ene-1,2-dione | 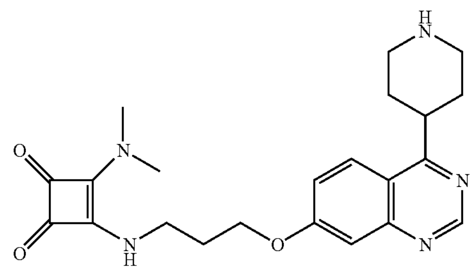 |
| 26 | Morpholine-4-carboxylic acid [3-(4-piperidin-4-yl-quinazolin-7-yloxy)-propyl]-amide | 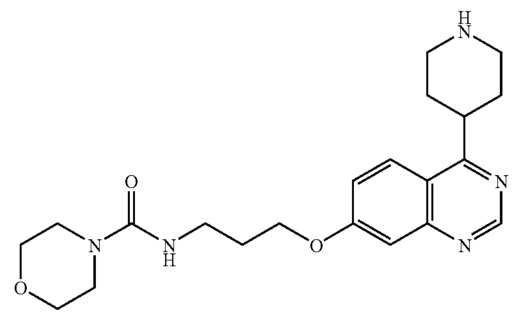 |
| 27 | 7-[3-(4-Ethyl-piperazin-1-yl)-propoxy]-4-piperidin-4-yl-quinazoline | 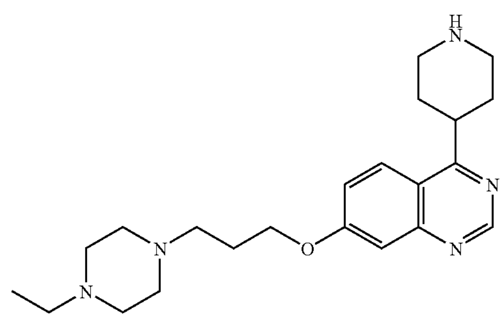 |
| 28 | 2-{4-[3-(4-Piperidin-4-yl-quinazolin-7-yloxy)-propyl]-piperazin-1-yl}-ethanol | 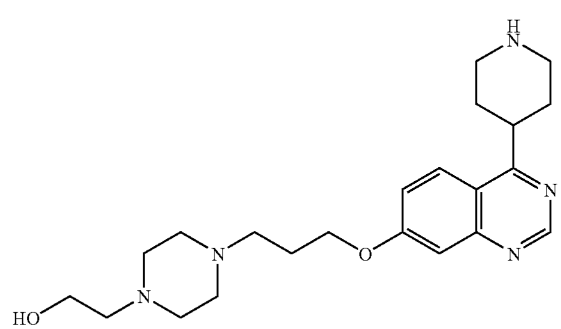 |

-continued

| Example No. | Name | Structure |
|---|---|---|
| 29 | 1-{4-[3-(4-Piperidin-4-yl-quinazolin-7-yloxy)-propyl]-piperazin-1-yl}-ethanone | 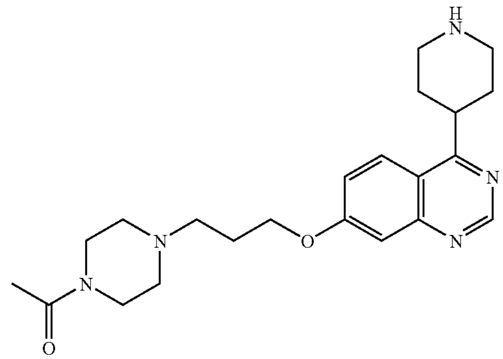 |
| 30 | 7-[3-(4-Methanesulfonyl-piperazin-1-yl)-propoxy]-4-piperidin-4-yl-quinazoline | 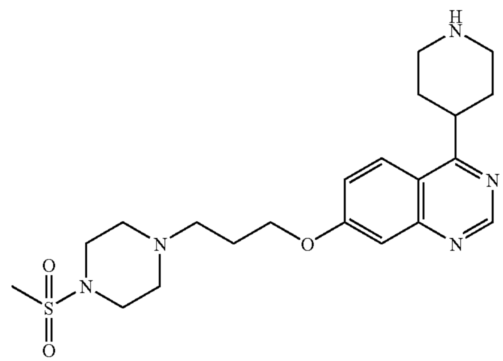 |
| 31 | (S)-{1-[3-(4-Piperidin-4-yl-quinazolin-7-yloxy)-propyl]-pyrrolidin-2-yl}-methanol | 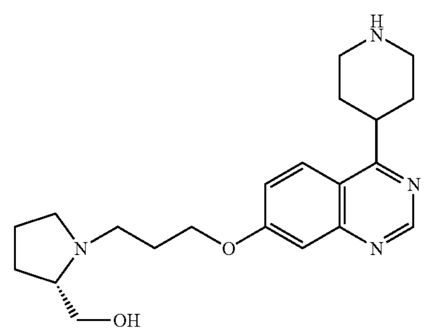 |
| 32 | 4-[3-(4-Piperidin-4-yl-quinazolin-7-yloxy)-propyl]-piperazine-1-carboxylic acid dimethylamide | 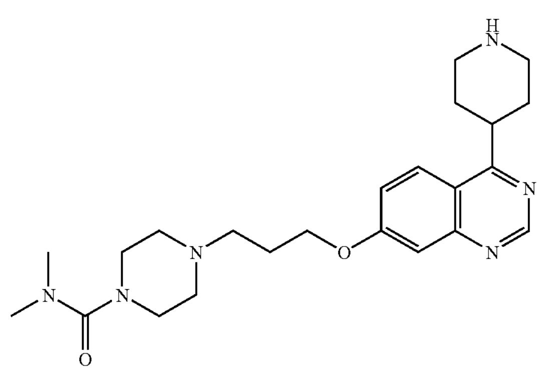 |

-continued

| Example No. | Name | Structure |
|---|---|---|
| 33 | 4-Piperidin-4-yl-7-(3-pyrrolidin-1-yl-propoxy)-quinazoline | 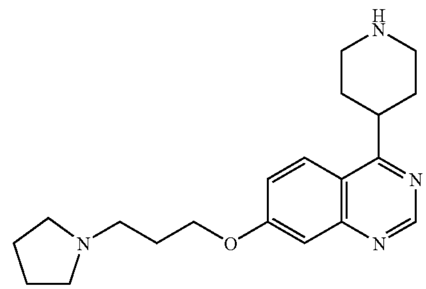 |
| 34 | 7-[3-(4-Methyl-[1,4]diazepan-1-yl)-propoxy]-4-piperidin-4-yl-quinazoline | 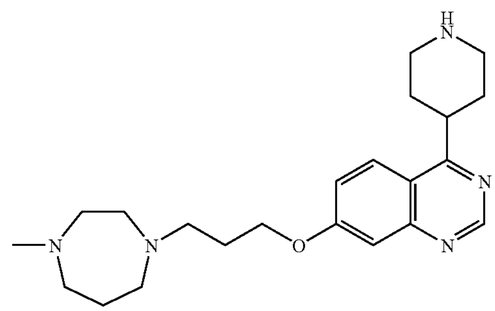 |
| 35 | 4-[7-(R)-3-Hydroxy-pyrrolidin-1-yl]-quinazolin-4-yl]-piperidine-1-carboxylic acid tert-butyl ester | 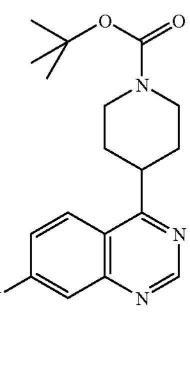 |
| 36 | 7-(1-Methyl-piperidin-4-yloxy)-4-piperidin-4-yl-quinazoline | 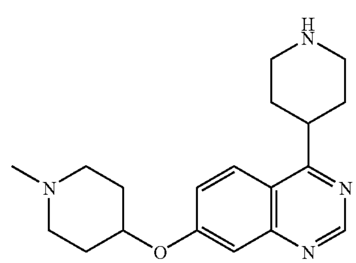 |

-continued
| Example No. | Name | Structure |
|---|---|---|
| 37 | (S)-1-(4-Piperidin-4-yl-quinazolin-7-yl)-pyrrolidin-3-ol | 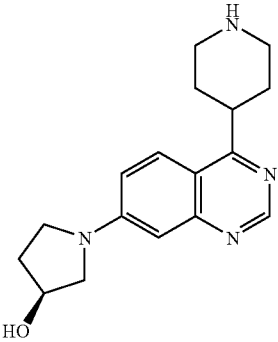 |
| 38 | (R)-7-(2-Methoxymethyl-pyrrolidin-1-yl)-4-piperidin-4-yl-quinazoline | 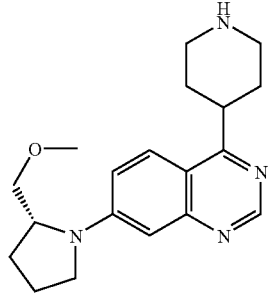 |
| 39 | 6-(4-Methyl-piperazin-1-yl)-4-piperidin-4-yl-quinazoline | 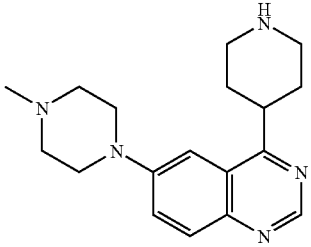 |
| 40 | (R)-[1-(4-Piperidin-4-yl-quinazolin-7-yl)-pyrrolidin-2-yl]-methanol | 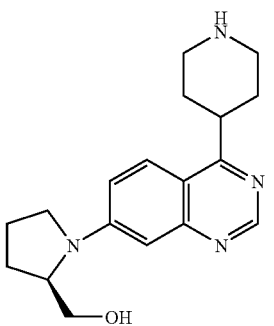 |
| 41 | 7-(4-Ethyl-piperazin-1-yl)-4-piperidin-4-yl-quinazoline | 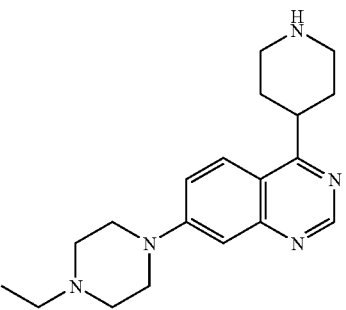 |

-continued
| Example No. | Name | Structure |
|---|---|---|
| 42 | 2-[4-(4-Piperidin-4-yl-quinazolin-7-yl)-piperazin-1-yl]-ethanol | 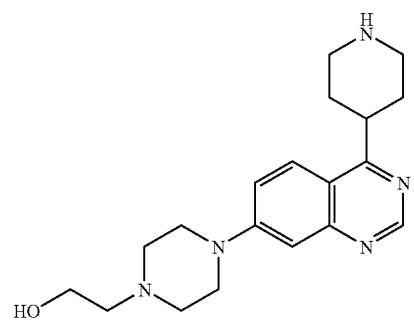 |
| 43 | 7-(4-Methyl-[1,4]diazepan-1-yl)-4-piperidin-4-yl-quinazoline | 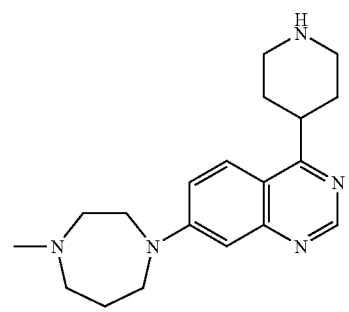 |
| 44 | (S)-[1-(4-Piperidin-4-yl-quinazolin-7-yl)-pyrrolidin-2-yl]-methanol | 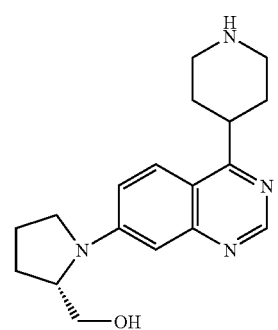 |
| 45 | 4-(7-piperazin-1-yl-quinazolin-4-yl)-piperidine-1-carboxylic acid tert-butyl ester | 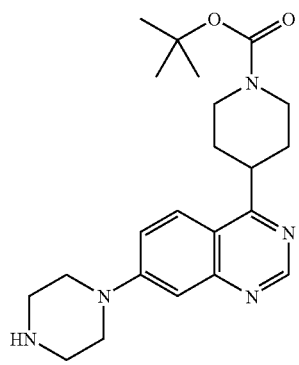 |

-continued
| Example No. | Name | Structure |
|---|---|---|
| 46 | 2-(9H-Fluoren-9-yl)-1-[4-(4-piperidin-4-yl-quinazolin-7-yl)-piperazin-1-yl]-ethanone | 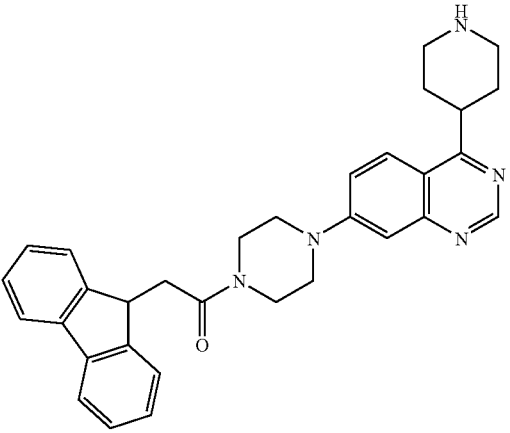 |
| 47 | 1-[4-(4-Piperidin-4-yl-quinazolin-7-yl)-piperazin-1-yl]-ethanone | 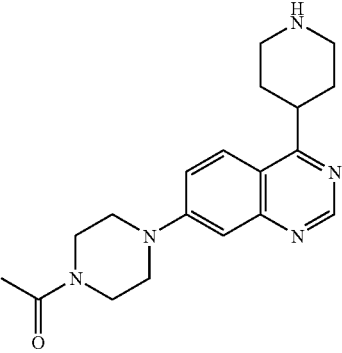 |
| 48 | 7-(4-Methanesulfonyl-piperazin-1-yl)-4-piperidin-4-yl-quinazoline | 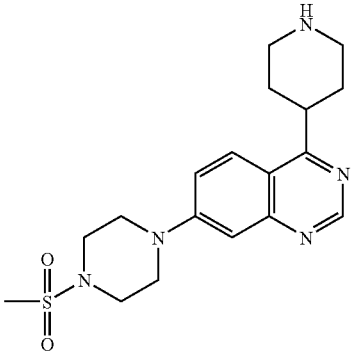 |
| 49 | 4-(4-Piperidin-4-yl-quinazolin-7-yl)-piperazine-1-carboxylic acid dimethylamide | 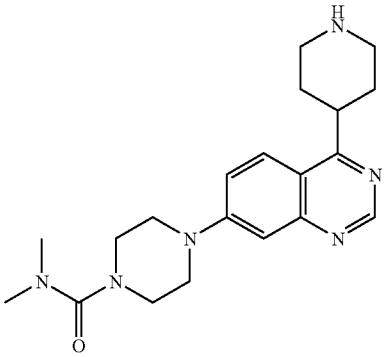 |

-continued
| Example No. | Name | Structure |
|---|---|---|
| 50 | 2-Dimethylamino-1-[4-(4-piperidin-4-yl-quinazolin-7-yl)-piperazin-1-yl]-ethanone | 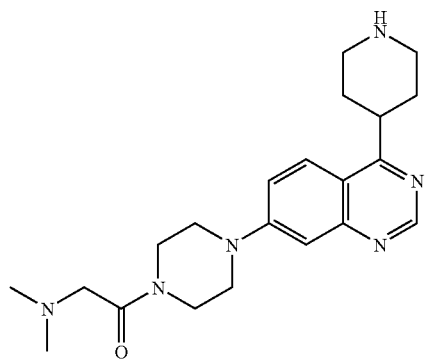 |
| 51 | 7-Morpholin-4-yl-4-piperidin-4-yl-quinazoline | 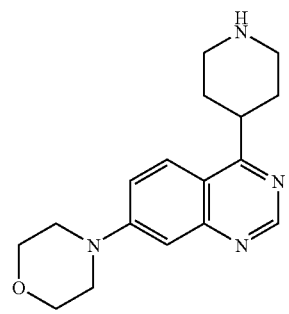 |
| 52 | (2-Methanesulfonyl-ethyl)-(4-piperidin-4-yl-quinazolin-7-yl)-amine | 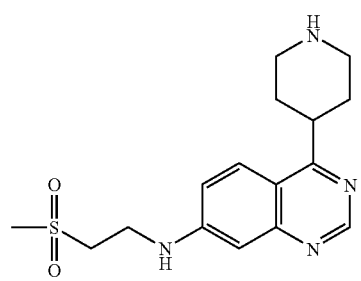 |
| 53 | (R)-Dimethyl-[1-(4-piperidin-4-yl-quinazolin-7-yl)-pyrrolidin-3-yl]-amine | 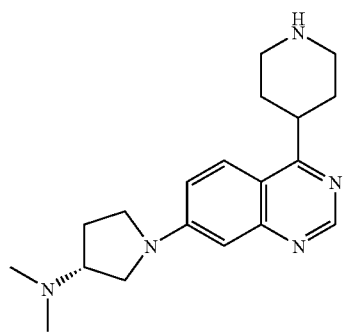 |

-continued
| Example No. | Name | Structure |
|---|---|---|
| 54 | (S)-7-(1-Methyl-pyrrolidin-2-ylmethoxy)-4-piperidin-4-yl-quinazoline | 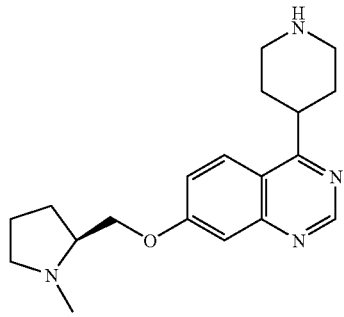 |
| 55 | (S)-{1-[2-(4-Piperidin-4-yl-quinazolin-7-yloxy)-ethyl]-pyrrolidin-2-yl}-methanol | 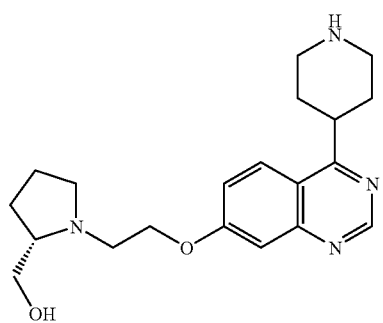 |
| 56 | (R)-4-[7-(1-Acetyl-pyrrolidin-3-yloxy)-quinazolin-4-yl]-piperidine-1-carboxylic acid tert-butyl ester | 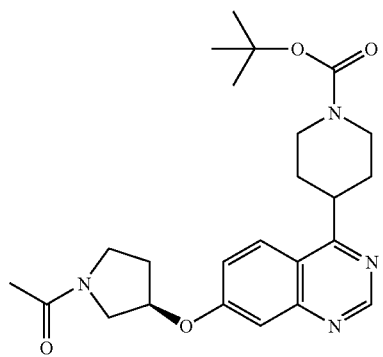 |
| 57 | 1-(4-Piperidin-4-yl-quinazolin-7-yl)-piperidine-4-carboxylic acid methylamide | 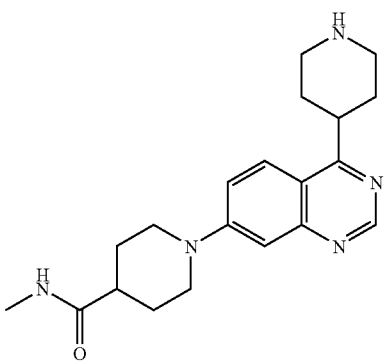 |

| Example No. | Name | Structure |
|---|---|---|
| 58 | 7-[2-(4-Methyl-piperazin-1-yl)-ethoxy]-4-piperidin-4-yl-quinazoline | 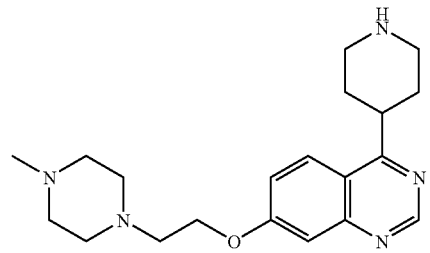 |
| 59 | (S)-1-[2-(4-Piperidin-4-yl-quinazolin-7-yloxymethyl)-pyrrolidin-1-yl]-ethanone | 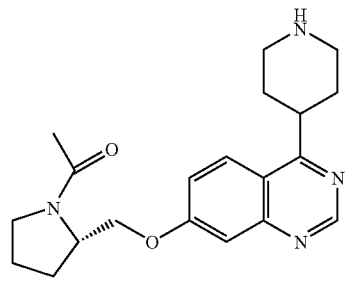 |
| 60 | 1-[4-(4-Piperidin-4-yl-quinazolin-7-yloxymethyl)-piperidin-1-yl]-ethanone | 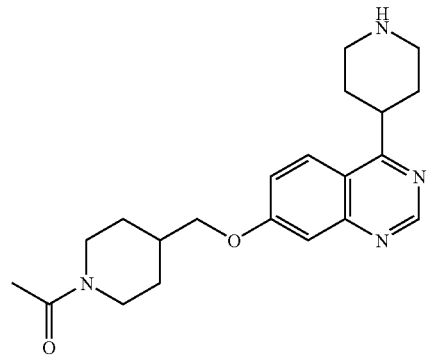 |
| 61 | 4-[7-(1-Acetyl-azetidin-3-yloxy)-quinazolin-4-yl]-piperidine-1-carboxylic acid tert-butyl ester | 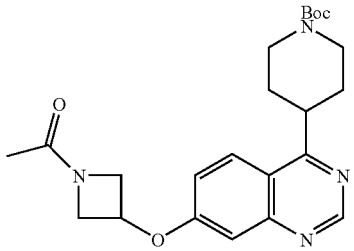 |
| 62 | 4-[7-(1-Methanesulfonyl-azetidin-3-yloxy)-quinazolin-4-yl]-piperidine-1-carboxylic acid tert-butyl ester | 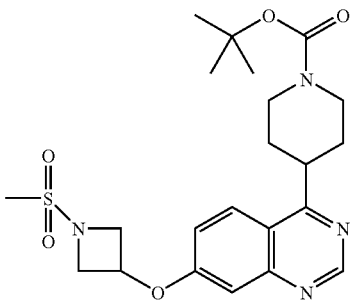 |

| Example No. | Name | Structure |
|---|---|---|
| 63 | 4-[7-(2-Morpholin-4-yl-2-oxo-ethoxy)-quinazolin-4-yl]-piperidine-1-carboxylic acid tert-butyl ester | 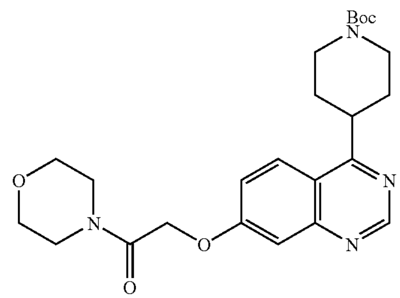 |
| 64 | 4-(7-Azetidin-1-yl-quinazolin-4-yl)-piperidine-1-carboxylic acid tert-butyl ester | 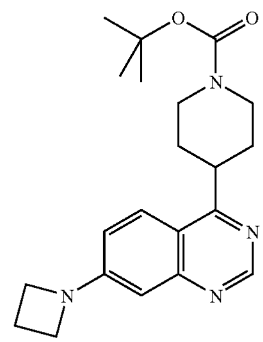 |
| 65 | 4-[7-(Pyridin-3-yloxy)-quinazolin-4-yl]-piperidine-1-carboxylic acid tert-butyl ester | 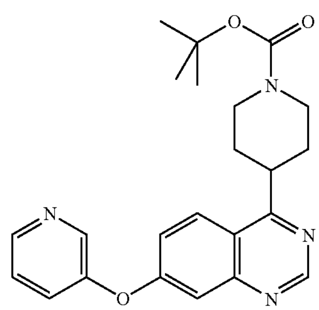 |
| 66 | 4-[7-(2-Hydroxy-ethylamino)-quinazolin-4-yl]-piperidine-1-carboxylic acid tert-butyl ester | 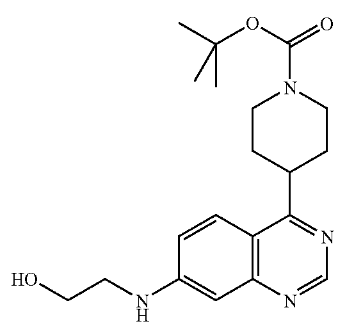 |

-continued

| Example No. | Name | Structure |
|---|---|---|
| 67 | 4-[7-(2-Oxo-oxazolidin-3-yl)-quinazolin-4-yl]-piperidine-1-carboxylic acid tert-butyl ester | 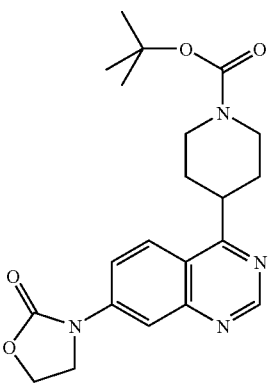 |
| 68 | (R)-4-[7-(1-Methanesulfonyl-pyrrolidin-3-yloxy)-quinazolin-4-yl]-piperidine-1-carboxylic acid tert-butyl ester | 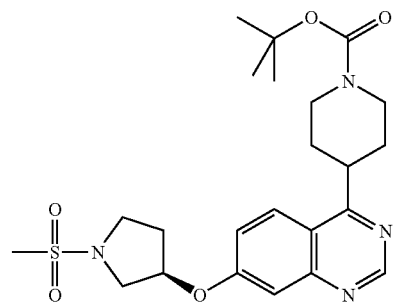 |
| 69 | 4-[7-(2-Oxo-imidazolidin-1-yl)-quinazolin-4-yl]-piperidine-1-carboxylic acid tert-butyl ester | 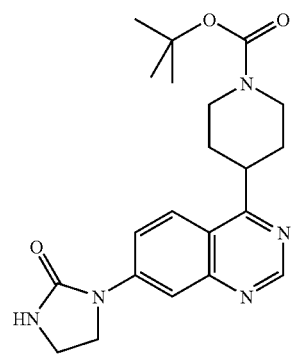 |
| 70 | 4-(7-Pyrrolidin-1-yl-quinazolin-4-yl)-piperidine-1-carboxylic acid tert-butyl ester | 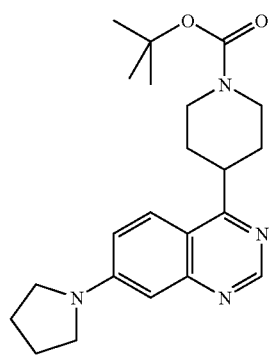 |

| Example No. | Name | Structure |
|---|---|---|
| 71 | 4-(7-Imidazol-1-yl-quinazolin-4-yl)-piperidine-1-carboxylic acid tert-butyl ester | 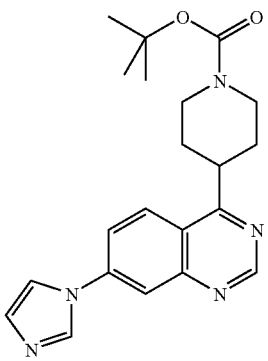 |
| 72 | 4-(7-Thiomorpholin-4-yl-quinazolin-4-yl)-piperidine-1-carboxylic acid tert-butyl ester | 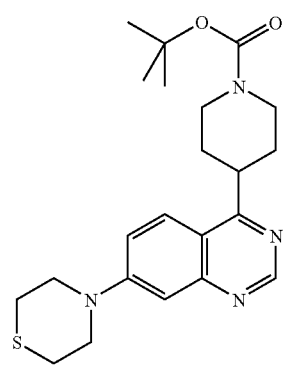 |
| 73 | 4-[7-(3-Oxo-piperazin-1-yl)-quinazolin-4-yl]-piperidine-1-carboxylic acid tert-butyl ester | 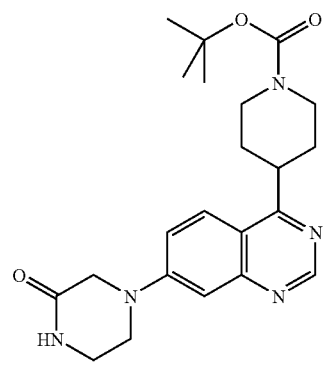 |
| 74 | 4-[7-(4-Methyl-3-oxo-piperazin-1-yl)-quinazolin-4-yl]-piperidine-1-carboxylic acid tert-butyl ester | 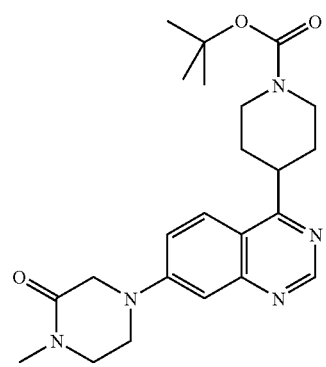 |

-continued

| Example No. | Name | Structure |
|---|---|---|
| 75 | 4-{7-[4-(2-Methoxy-ethyl)-piperazin-1-yl]-quinazolin-4-yl}-piperidine-1-carboxylic acid tert-butyl ester | 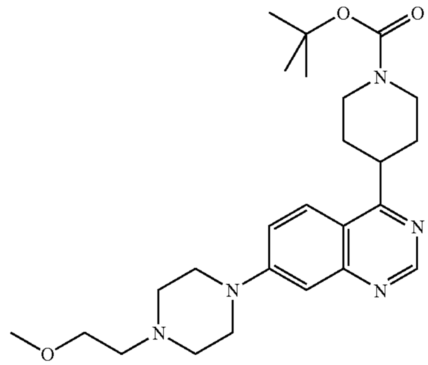 |
| 76 | 4-Piperidin-4-yl-7-(tetrahydro-pyran-4-ylmethoxy)-quinazoline | 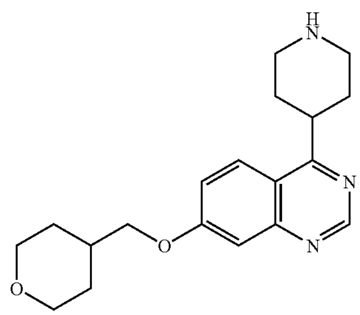 |
| 77 | 4-Piperidin-4-yl-7-(tetrahydro-pyran-4-yloxy)-quinazoline | 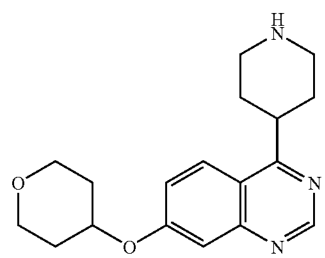 |
| 78 | (S)-4-Piperidin-4-yl-7-(tetrahydro-furan-3-yloxy)-quinazoline | 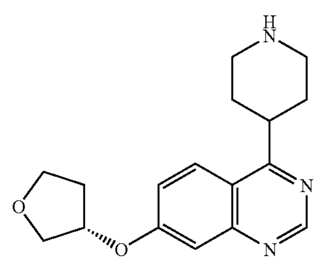 |
| 79 | (R)-4-Piperidin-4-yl-7-(tetrahydro-furan-3-yloxy)-quinazoline | 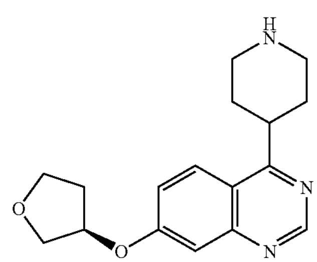 |

-continued

| Example No. | Name | Structure |
|---|---|---|
| 80 | 4-[7-(4-Pyridin-2-yl-piperazin-1-yl)-quinazolin-4-yl]-piperidine-1-carboxylic acid tert-butyl ester | 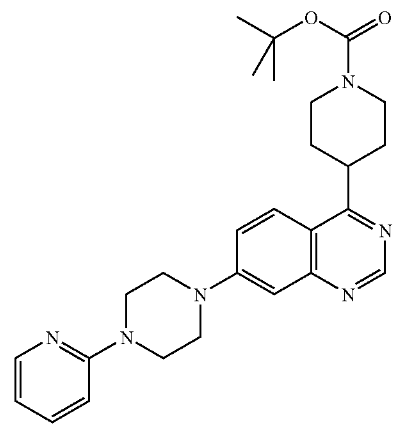 |
| 81 | 4-[7-(4-Pyrimidin-2-yl-piperazin-1-yl)-quinazolin-4-yl]-piperidine-1-carboxylic acid tert-butyl ester | 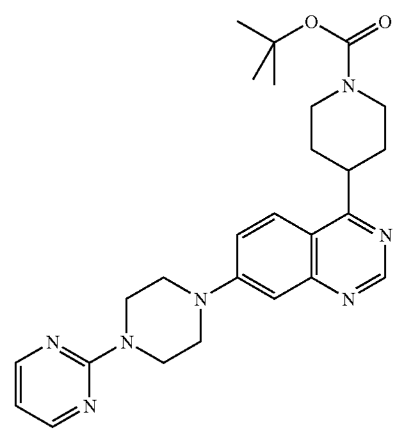 |
| 82 | 4-[7-(4-Pyridin-4-yl-piperazin-1-yl)-quinazolin-4-yl]-piperidine-1-carboxylic acid tert-butyl ester | 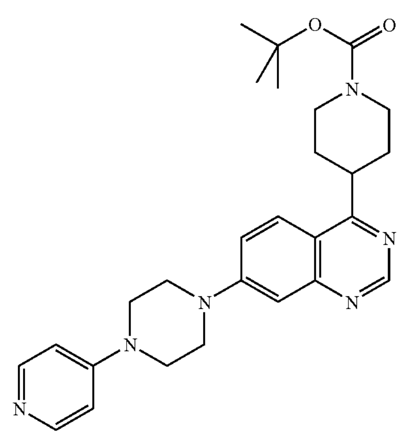 |

-continued

| Example No. | Name | Structure |
|---|---|---|
| 83 | 4-[7-(4-Fluoro-piperidin-1-yl)-quinazolin-4-yl]-piperidine-1-carboxylic acid tert-butyl ester | 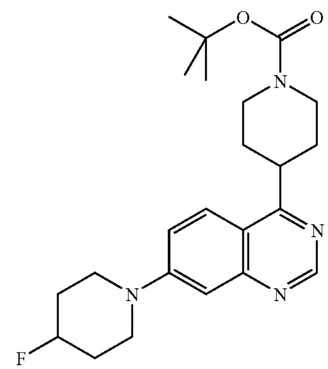 |
| 84 | 4-(4-Piperidin-4-yl-quinazolin-7-yl)-piperazine-1-carboxylic acid ethylamide | 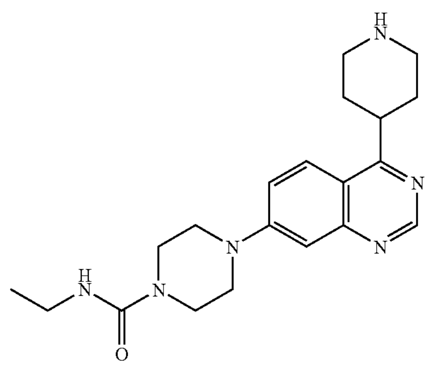 |
| 85 | 2-Methoxy-1-[4-(4-piperidin-4-yl-quinazolin-7-yl)-piperazin-1-yl]-ethanone | 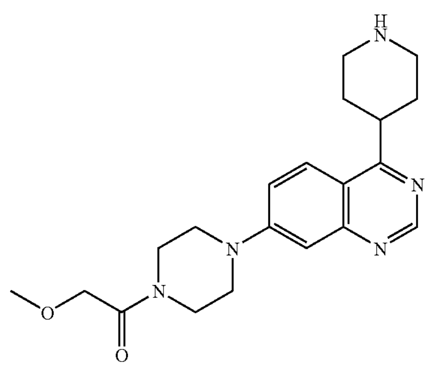 |
| 86 | 2-Hydroxy-1-[4-(4-piperidin-4-yl-quinazolin-7-yl)-piperazin-1-yl]-ethanone | 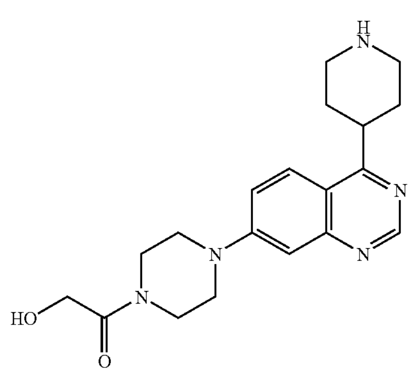 |

-continued

| Example No. | Name | Structure |
|---|---|---|
| 87 | 1-Methyl-4-[2-(4-piperidin-4-yl-quinazolin-7-yloxy)-ethyl]-piperazin-2-one | 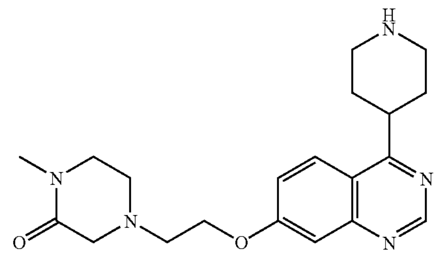 |
| 88 | 6-Methoxy-4-piperidin-4-yl-quinazoline | 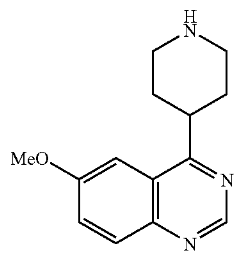 |
| 89 | 4-{7-[3-(1H-Tetrazol-5-yl)-propoxy]-quinazolin-4-yl}-piperidine-1-carboxylic acid tert-butyl ester | 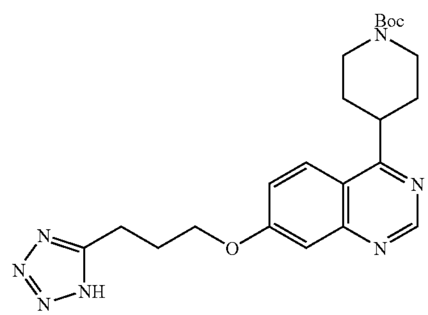 |
| 90 | 4-{6-Fluoro-7-[3-(4-methyl-piperazin-1-yl)-propoxy]-quinazolin-4-yl}-piperidine-1-carboxylic acid tert-butyl ester | 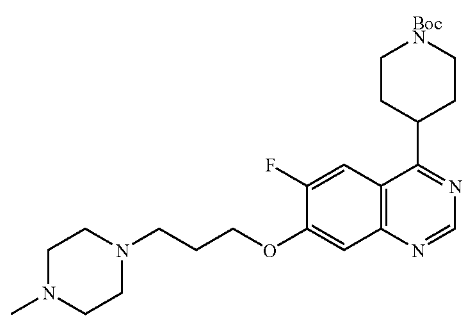 |
| 91 | 4-{6-Fluoro-7-[2-(2-oxo-pyrrolidin-1-yl)-ethoxy]-quinazolin-4-yl}-piperidine-1-carboxylic acid tert-butyl ester | 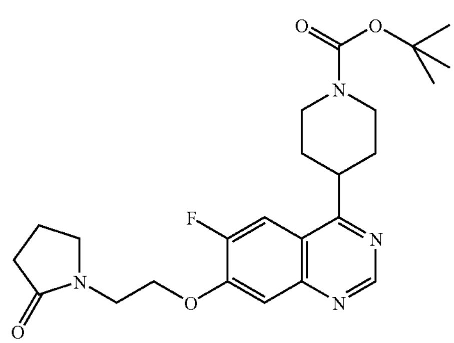 |

-continued

| Example No. | Name | Structure |
|---|---|---|
| 92 | 4-{6-Methoxy-7-[3-(4-methyl-piperazin-1-yl)-propoxy]-quinazolin-4-yl}-piperidine-1-carboxylic acid tert-butyl ester | 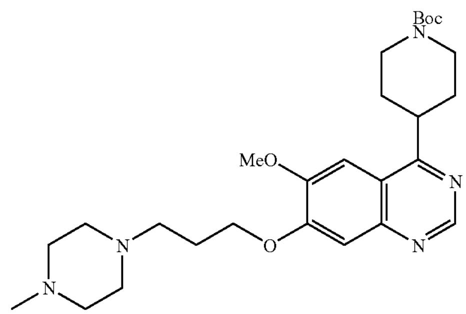 |
| 93 | 4-{6-Methoxy-7-[2-(2-oxo-pyrrolidin-1-yl)-ethoxy]-quinazolin-4-yl}-piperidine-1-carboxylic acid tert-butyl ester | 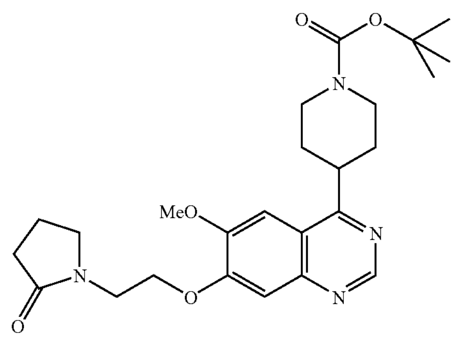 |
| 94 | 4-(6-Fluoro-7-morpholin-4-yl-quinazolin-4-yl)-piperidine-1-carboxylic acid tert-butyl ester | 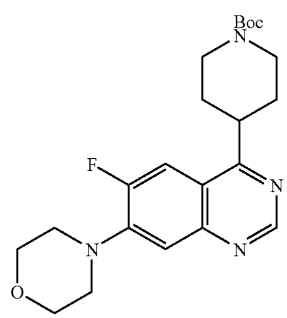 |
| 95 | 4-(6-Methoxy-7-morpholin-4-yl-quinazolin-4-yl)-piperidine-1-carboxylic acid tert-butyl ester | 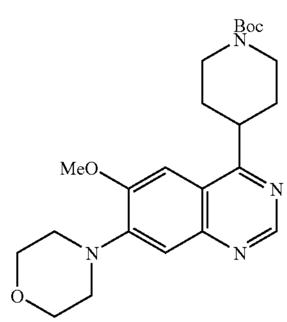 |

EXAMPLE 1

6,7-Dimethoxy-4-piperidin-4-yl-quinazoline

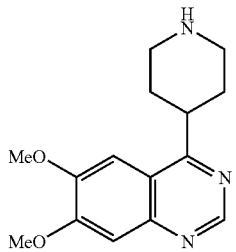

a. Piperidine-1,4-dicarboxylic acid 1-tert-butyl ester 4-methyl ester

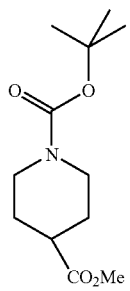

To a mixture of isonipecotic acid (39.0 g, 302 mmol) in MeOH (300 mL) was bubbled HCl gas. The flask was tightly capped and stirred at rt for 1.5 h, at which point the homogeneous solution was concentrated, taken up in DCM (2×125 mL), and repeatedly concentrated under reduced pressure to give a white solid largely free of MeOH. To this was added TEA (43.6 mL, 313 mmol) and DCM (80 mL), and this slurry was stirred on an ice bath while a solution of $(Boc)_2O$ (60.9 g, 279 mmol) in DCM (100 mL) was added dropwise with stirring over 10 min at 0° C. After 1 h stirring at 0° C., the ice bath was removed and the slurry was stirred at rt overnight. The slurry was then diluted with ether (700 mL), washed with 0.5M $NaH_2PO_4$ (1×400 mL), 4 M NaCl (1×450 mL), dried ($Na_2SO_4$), and concentrated under reduced pressure to provide the title compound as a clear light amber oil that crystallized upon standing (65.3 g, 96%). $^1$H-NMR (300 MHz, $CDCl_3$) δ 4.10-3.95 (br m, 2H), 3.69 (s, 3H), 2.92-2.75 (br m, 2H), 2.45 (m, 1H), 1.93-1.82 (m, 2H), 1.70-1.55 (m, 2H), 1.46 (s, 9H).

b. 4-(6,7-Dimethoxy-quinazolin-4-yl)-piperidine-1,4-dicarboxylic acid 1-tert-butyl ester 4-methyl ester

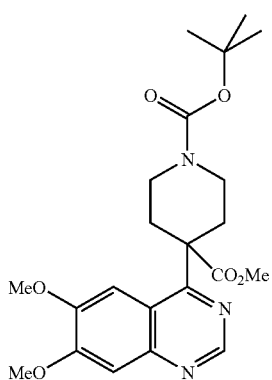

To a mixture of piperidine-1,4-dicarboxylic acid 1-tert-butyl ester 4-methyl ester (17.1 g, 70.5 mmol), as prepared in the previous step, and 4-chloro-6,7-dimethoxyquinazoline (15.0 g, 67.0 mmol) (Oakwood Products, Inc.) immersed in a −78° C. bath was added 1.08 M LiHMDS/THF (71 mL, 77 mmol) in ~20 mL portions under argon via syringe along the sides of the flask (to allow cooling of the hindered base before reaction with the ester). Following completion of LiHMDS/THF addition, the reaction was allowed to sit in the −78° C. bath for 2-3 min before removing the cold bath and allowing the mixture to stir with gradual warming to rt. After 18 h stirring at rt, and an additional 2 d sitting at rt, the mixture was quenched with 0.5 M $NaH_2PO_4$ (150 mL) and extracted with DCM (1×150 mL and 1×100 mL). The organic layers were combined, dried ($Na_2SO_4$), and concentrated under reduced pressure to provide the crude title compound as a translucent yellow oil that was used in the next step without further purification (33g). A small sample was purified by flash chromatography (1:1 hex/EtOAc) for characterization. $^1$H-NMR (400 MHz, $CDCl_3$) δ 9.11 (s, 1H), 7.34 (s, 1H), 7.29 (s, 1H), 4.05 (s, 3H), 3.96 (s, 3H), 3.76-3.67 (m, 2H), 3.62-3.49 (m, 2H), 3.61 (s, 3H), 2.50-2.36 (br s, 4H), 1.46 (s, 9H). LC/MS (ESI): calcd mass 431.2, found 432.2 $(MH)^+$.

c. 6,7-Dimethoxy-4-piperidin-4-yl-quinazoline

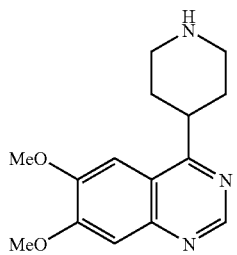

A mixture of crude 4-(6,7-dimethoxy-quinazolin-4-yl)-piperidine-1,4-dicarboxylic acid 1-tert-butyl ester 4-methyl ester (33 g), as prepared in the previous step, MeOH (100 mL), and KOH pellets (26 g, 400 mmol assuming 87% w/w water) was stirred at reflux (100° C. oil bath) for 1 h, at which point the translucent reddish-amber solution was allowed to cool to rt and diluted with water (100 mL) and 6 M HCl (100 mL). The solution was stirred at 100° C. for 10 min (Caution: Initial vigorous bubbling), allowed to cool to rt, diluted with 2.5 M NaOH (90 mL) and extracted with DCM (1×150 mL; 1×50 mL). The organic layers were combined, dried ($Na_2SO_4$), and concentrated under reduced pressure to afford the title compound as a beige powder (13.95g, 76% from 4-chloro-6,7-dimethoxyquinazoline). $^1$H-NMR (300 MHz, DMSO-$d_6$) δ 8.98 (s, 1H), 7.48 (s, 1H), 7.32 (s, 1H), 3.98 (s, 3H), 3.96 (s, 3H)m 3.69 (m, 1H), 3.05 (m, 2H), 2.84-2.71 (m, 2H), 1.88-1.65 (m, 4H). LC/MS (ESI): calcd mass 273.2, found 274.2 $(MH)^+$.

EXAMPLE 2

6-Iodo-4-piperidin-4-yl-quinazoline

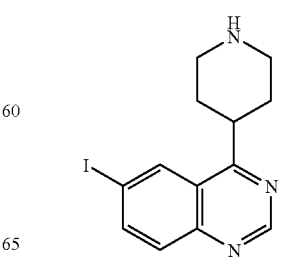

a. 4-Chloro-6-iodo-quinazoline

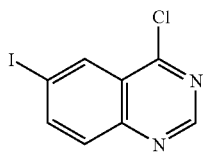

A mixture of 5-iodoanthranilic acid (9.96 g, 37.9 mmol) and formamidine acetate (4.20 g, 40.3 mmol) (adapted from *J. Org. Chem.* 51:616, 1986) in absolute EtOH (80 mL) was refluxed under air for 2 h. The smoky amber solution with heavy white precipitate was then concentrated under reduced pressure at 90° C., and residual protic solvent was removed with toluene rotary evaporation (2×100 mL) at 90° C. The resulting sticky tan solid was treated with a thick white slurry of Vilsmeier-Haack reagent in one portion under air at rt. [The Vilsmeier-Haack reagent was prepared by the addition of a solution of oxalyl chloride (10.9 mL, 125 mmol) in DCE (44 mL) to a solution of DMF (6.7 mL, 87 mmol) in DCE (21 mL) dropwise over 10 min at 0° C. with vigorous stirring. The ice bath was removed immediately following completion of oxalyl chloride addition, and the white slurry was stirred at "rt" for 5 min before transfer to the crude 4-hydroxy-6-iodo-quinazoline intermediate.] The reaction was then refluxed under air (oil bath 110° C.) for 1 h 15 min, and the resulting homogeneous brown solution was allowed to cool to rt, at which point a heavy precipitate formed. The reaction was poured into ice water (300 mL) and extracted with DCM (3×250 mL). The opaque organic layers were combined, dried ($Na_2SO_4$), and filtered to provide a clear red amber filtrate. Concentration under reduced pressure, followed by toluene rotary evaporation at 90° C. to remove potentially reactive volatiles, afforded the title compound as a tan powder (8.41 g, 94% from iodoanthranilic acid) suitable for treatment with LiHMDS in the next step. $^1$H-NMR (300 MHz, $CDCl_3$) δ 9.07 (s, 1H), 8.67 (dd, 1H), 8.22 (dd, 1H), 7.81 (d, 1H).

b. 4-(6-Iodo-quinazolin-4-yl)-piperidine-1,4-dicarboxylic acid 1-tert-butyl ester 4-methyl ester

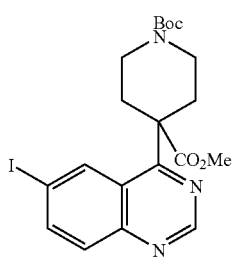

Prepared essentially as described in Example 1c using 4-chloro-6-iodo-quinazoline, as prepared in the preceding step, 1.1 eq LiHMDS/THF and 1.1 eq piperidine-1,4-dicarboxylic acid 1-tert-butyl ester 4-methyl ester, as prepared in Example 1b, and stirring at rt for 14 h following enolate formation at −78° C. The homogeneous brown solution was worked up as described in Example 1c to provide the impure crude title compound as a very dark brown thick oil (14.97 g). $^1$H-NMR (300 MHz, $CDCl_3$) δ 9.28 (s, 1H), 8.41 (d, 1H), 8.10 (dd, 1H), 7.80 (d, 1H), 3.8-3.5 (m, 4H), 3.66 (s, 3H), 2.45-2.35 (m, 4H), 1.46 (s, 9H). LC/MS (ESI): calcd mass 497.1, found 398.0 (MH-Boc)+.

c. 6-Iodo-4-piperidin-4-yl-quinazoline

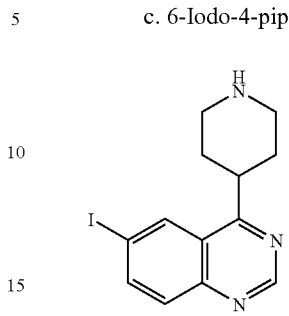

A mixture of 4-(6-iodo-quinazolin-4-yl)-piperidine-1,4-dicarboxylic acid 1-tert-butyl ester 4-methyl ester (14.21 g, 28.6 mmol), prepared as described in the preceding step, LiCl (2.38 g, 56.1 mmol), water (1.54 mL, 85.8 mmol), and DMSO (14 mL) was stirred at 150° C. under air for 3 h in a 500 mL flask fitted with a lightly capped Liebig condenser to minimize loss of reagent water while allowing gas escape. The reaction was then allowed to cool to rt, 2 M HCl (aq) (100 mL) was added, and the mixture was stirred at 100° C. for 10 min (Caution: Gas evolution). The reaction was cooled on an ice bath, 2.5 M NaOH (100 mL) was added, and the reaction was extracted with DCM (1×250 mL and 1×50 mL). The organic layers were combined, dried ($Na_2SO_4$), and concentrated to provide a 60:40 mixture of the title compound and its methyl ester, contaminated with DMSO, as a dark green oil (10.5 g). This material was resubjected to Krapchow decarboxylation conditions using LiCl (2.41 g, 63 mmol), water (1.54 mL, 85.8 mmol), and DMSO (4 mL) (~7 mL total DMSO) for an additional 5 h at 150° C. After a total of 8 h at 150° C., the reaction was allowed to cool to rt, and 3 M HCl (100 mL) was added (gas evolution) and the reaction stirred at 100° C. for 15 min. The reaction was then stirred at 0° C. while 2.5 M NaOH (120 mL) was added slowly over ~30 s to pH >12 (paper), and the cream-colored opaque slurry was extracted with 9:1 DCM/MeOH (4×100 mL). The combined organic layers were dried ($Na_2SO_4$) and concentrated under reduced pressure to provide the title compound as a clear dark green oil contaminated with DMSO and an aromatic impurity (5.97 g). $^1$H-NMR (300 MHz, $CDCl_3$) δ 9.27 (s, 1H), 8.52 (d, 1H), 8.12 (dd, 1H), 7.78 (d, 1H), 3.68-3.55 (m, 1H), 3.36-3.27 (m, 2H), 2.92 (td, 2H), 2.1-1.8 (m, 5H). LC/MS (ESI): calcd mass 339.0, found 340.1 (MH)+.

EXAMPLE 3

4-(7-chloro-quinazolin-4-yl)-piperidine

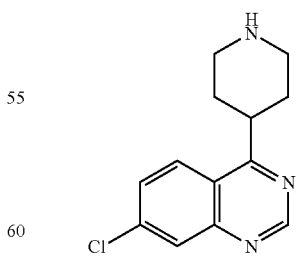

To a stirred mixture of 4,7-Dichloroquinazoline (800 mg, 4 mmol) and piperidine-1,4-dicarboxylic acid 1-tert-butyl ester 4-methyl ester (1.2 g, 5.2 mmol), as prepared in Example 1a, in a sealed vial at rt was added drop-wise a 1 M solution of LiHMDS in THF (6 mL, 6 mmol). The mixture was stirred at rt overnight. It was then quenched with aqueous $NaH_2PO_4$ and the mixture was extracted with DCM. The DCM layer was drawn off, washed with water, brine, dried over anhydrous MgSO$_4$, filtered and concentrated in vacuo to obtain 2.2 g (>100%) of crude 4-(7-chloro-quinazolin-4-yl)-piperidine-1,4-dicarboxylic acid 1-tert-butyl ester 4-methyl ester (3a) as a yellow semi-solid which was used as such for the next step. Solid KOH (224 mg, 4 mmol) was added to a suspension of 4-(7-chloro-quinazolin-4-yl)-piperidine-1,4-dicarboxylic acid 1-tert-butyl ester 4-methyl ester (3a; 41 mg, 0. 1 mmol) in a 1:1 mixture of dioxane and water (1 mL). The mixture was stirred at 100° C. for 3 h. It was then cooled to rt and concentrated in vacuo. The residue was dissolved in DCM and washed with water, brine, dried over anhydrous MgSO$_4$, filtered and concentrated in vacuo to obtain crude 4-(7-chloro-quinazolin-4-yl)-piperidine-1-carboxylic acid tert-butyl ester (3b). This was dissolved in 2 mL of 3M HCl/MeOH was stirred at rt for 1 h and then concentrated in vacuo to obtain crude 4-(7-chloro-quinazolin-4-yl)-piperidine (3c) as a di-HCl salt.

EXAMPLE 4

4-(7-methoxy-quinazolin-4-yl)-piperidine

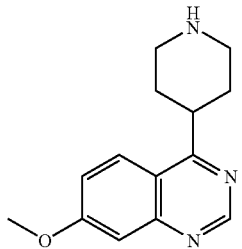

Solid KOH (224 mg, 4 mmol) was added to a solution of 4-(7-chloro-quinazolin-4-yl)-piperidine-1,4-dicarboxylic acid 1-tert-butyl ester 4-methyl ester (3a; 41 mg, 0.1 mmol), prepared as described in Example 3, in anhydrous MeOH (1 mL). The mixture was stirred at 100° C. for 3 h. It was then cooled to rt and concentrated in vacuo. The residue was dissolved in DCM and washed with water, brine, dried over anhydrous MgSO$_4$, filtered and concentrated in vacuo to obtain crude 4-(7-methoxy-quinazolin-4-yl)-piperidine-1-carboxylic acid tert-butyl ester (4a). This was dissolved in 2 mL of 3M HCl/MeOH was stirred at rt for 1 h and then concentrated in vacuo to obtain crude 4-(7-methoxy-quinazolin-4-yl)-piperidine (4b) as a di-HCl salt.

EXAMPLE 5

4-Piperidin-4-yl-7-(3-piperidin-1-yl-propoxy)-quinazoline

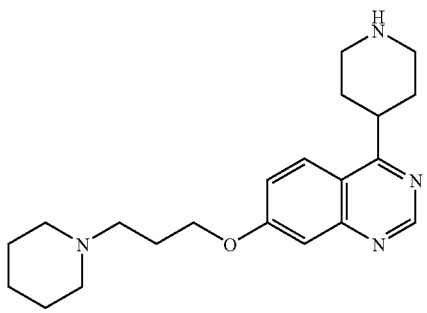

Solid KOH (112 mg, 2 mmol) was added to a mixture of 4-(7-chloro-quinazolin-4-yl)-piperidine-1,4-dicarboxylic acid 1-tert-butyl ester 4-methyl ester (3a; 82 mg, 0.2 mmol), prepared as described in Example 3, and 3-hydroxypropylpiperidine (0.25 mL). The mixture was stirred at 100° C. for 3 h. It was then cooled to rt and diluted with water. The mixture was extracted with DCM and the organic layer was drawn off and washed with water thrice, with brine once, then dried over anhydrous MgSO$_4$, filtered and concentrated in vacuo. To this was added 3 ML of 3M HCl/MeOH and the mixture was stirred at rt for 2 h and then concentrated in vacuo to afford crude 4-piperidin-4-yl-7-(3-piperidin-1-yl-propoxy)-quinazoline.

EXAMPLE 6

4-Piperidin-4-yl-7-(2-piperidin-1-yl-ethoxy)-quinazoline

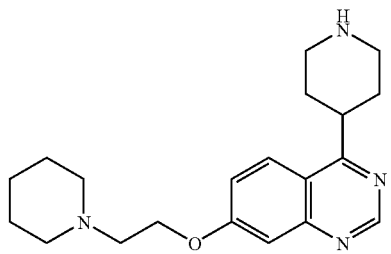

This was prepared as described in Example 5 except that 2-hydroxyethylpiperidine (0.5 mL) was used in place of 3-hydroxypropylpiperidine (0.25 mL).

EXAMPLE 7

Diethyl-[2-(4-piperidin-4-yl-quinazolin-7-yloxy)-ethyl]-amine

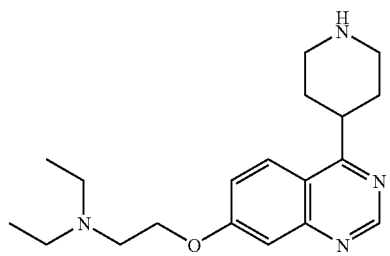

This was prepared as described in Example 5 except that 2-diethylaminoethanol (0.5 mL) was used in place of 3-hydroxypropylpiperidine (0.25 mL).

EXAMPLE 8

Diethyl-[3-(4-piperidin-4-yl-quinazolin-7-yloxy)-propyl]-amine

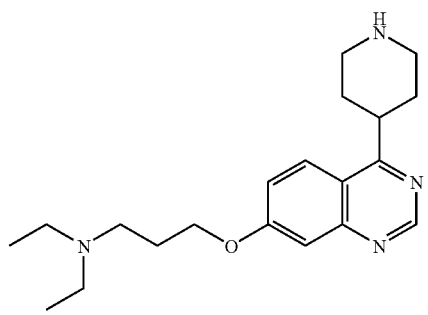

This was prepared as described in Example 5 except that 3-diethylaminopropanol (0.5 mL) was used in place of 3-hydroxypropylpiperidine (0.25 mL).

EXAMPLE 9

7-(2-Morpholin-4-yl-ethoxy)-4-piperidin-4-yl-quinazoline

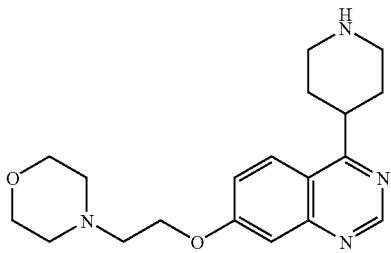

This was prepared as described in Example 5 except that 2-hydroxyethylmorpholine (0.5 mL) was used in place of 3-hydroxypropylpiperidine (0.25 mL).

EXAMPLE 10

7-(3-Morpholin-4-yl-propoxy)-4-piperidin-4-yl-quinazoline

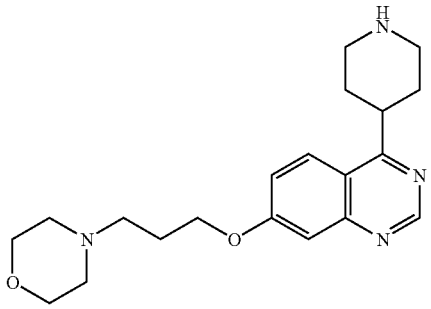

This was prepared as described in Example 5 except that 3-hydroxypropylmorpholine (0.5 mL) was used in place of 3-hydroxypropylpiperidine (0.25 mL).

EXAMPLE 11

7-[3-(4-Methyl-piperazin-1-yl)-propoxy]-4-piperidin-4-yl-quinazoline

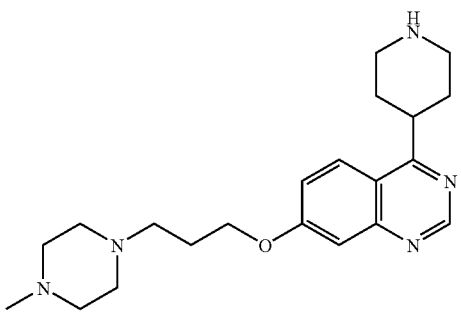

a. 4-(7-Fluoro-quinazolin-4-yl)-piperidine-1-carboxylic acid tert-butyl ester

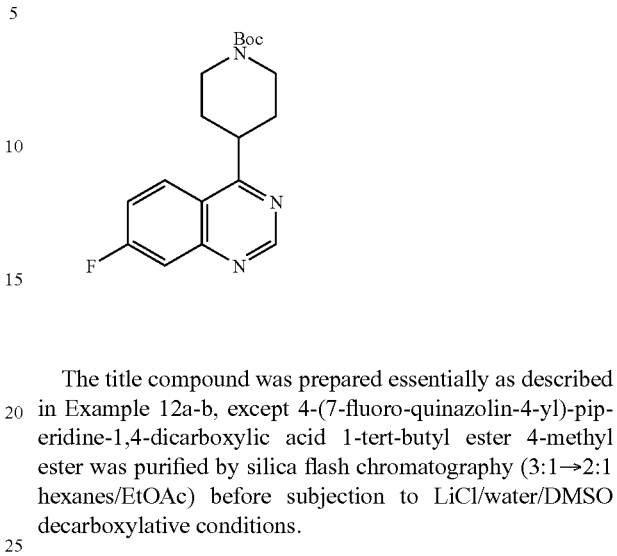

The title compound was prepared essentially as described in Example 12a-b, except 4-(7-fluoro-quinazolin-4-yl)-piperidine-1,4-dicarboxylic acid 1-tert-butyl ester 4-methyl ester was purified by silica flash chromatography (3:1→2:1 hexanes/EtOAc) before subjection to LiCl/water/DMSO decarboxylative conditions.

b. 7-[3-(4-Methyl-piperazin-1-yl)-propoxy]-4-piperidin-4-yl-quinazoline

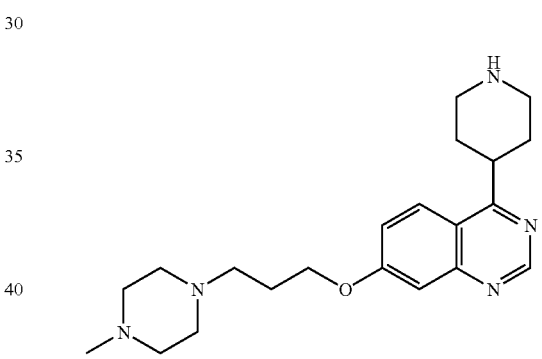

Solid KOtBu (1.36 g, 12.1 mmol) was added in one portion under air to a homogeneous solution of 4-(7-Fluoro-quinazolin-4-yl)-piperidine-1-carboxylic acid tert-butyl ester (3.33 g, 10.1 mmol), as prepared in the preceding step, and commercial 3-(4-methyl-piperazin-1-yl)-propan-1-ol (1.50 g, 9.50 mmol) in dry THF (10 mL), while stirring on an ice bath. Following KOtBu addition, the ice bath was immediately removed, and the resulting homogeneous amber solution was stirred for 6 hr. 6 M aqueous HCl (10 mL, 60 mmol) was then added in one portion, and the reaction was stirred overnight (mild bubbles were seen following HCl addition, but these subsided after 15 min). The reaction was then partitioned with 9:1 DCM/MeOH (50 mL) and 2.5 M NaOH (28 mL, 70 mmol), and the aqueous layer was extracted with 9:1 DCM/MeOH (1×50 mL). The combined organic layers were dried ($Na_2SO_4$) and concentrated by rotary evaporation at 90° C. to provide the crude title compound as a clear yellow oil (3.79 g). LC/MS (ESI): calcd mass 369.3, found 370.2 $(MH)^+$.

EXAMPLE 12

4-[7-(3-Methanesulfonylamino-propoxy)-quinazolin-4-yl]-piperidine-1-carboxylic acid tert-butyl ester

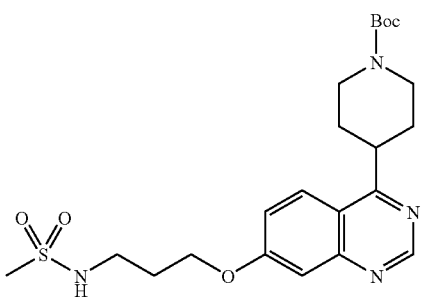

a. 4-(7-Fluoro-quinazolin-4-yl)-piperidine-1,4-dicarboxylic acid 1-tert-butyl ester 4-methyl ester

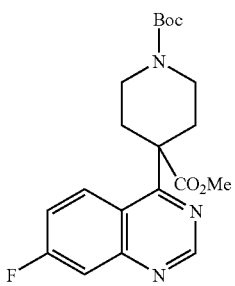

A mixture of 4-chloro-7-fluoro-quinazoline (2.87 g, 15.4 mmol) (WO 9609294 A1) and piperidine-1,4-dicarboxylic acid 1-tert-butyl ester 4-methyl ester (4.15 g, 17.1 mmol), as prepared in Example 1b, was placed in a −78° C. bath for 5 min under argon before adding a 1.08 M LiHMDS/THF solution (17.8 mL, 19.2 mmol) rapidly by syringe along the sides of the flask (to allow cooling and dispersion of the hindered base before reaction with the ester). Following completion of LiHMDS/THF addition, the reaction was manually swirled in the −78° C. bath for 2-3 min before removing the cold bath and allowing the mixture to stir with gradual warming to rt. After 2.5 h stirring at rt, the dark brown homogeneous solution was quenched with 1.0 M NaH$_2$PO$_4$ (38 mL) and extracted with DCM (1×150 mL and 1×25 mL). The organic layers were combined, dried (Na$_2$SO$_4$), and concentrated under reduced pressure, and subject to high vacuum at 90° C. with toluene chasers (3×10 mL) to provide the crude title compound as an opaque thick yellow oil that was used in the next step without further purification (6.83 g). $^1$H—NMR (300 MHz, CDCl$_3$) δ 9.26 (s, 1H), 8.11 (dd, 1H), 7.70 (dd, 1H), 7.36 (ddd, 1H), 3.74-3.64 (m, 2H), 3.62-3.51 (m, 2H), 3.61 (s, 3H), 2.47-2.38 (br m, 4H), 1.46 (s, 9H). LC/MS (ESI): calcd mass 389.2, found 390.1 (MH)$^+$.

b. 4-(7-Fluoro-quinazolin-4-yl)-piperidine-1-carboxylic acid tert-butyl ester

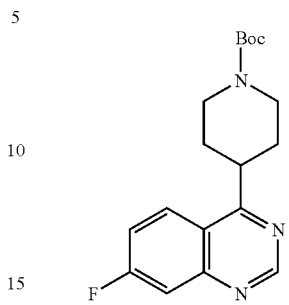

A mixture of 4-(7-fluoro-quinazolin-4-yl)-piperidine-1,4-dicarboxylic acid 1-tert-butyl ester 4-methyl ester ("6.83 g"), as prepared without further purification in the previous step, LiCl (1.32 g, 31.1 mmol), water (832 μL, 46.2 mmol), and DMSO (6.0 mL) was stirred under air at 150° C. (oil bath) with an efficient condenser (to retain reagent water) for 9.5 h. The dark solution was then allowed to cool to rt, shaken with 1.0 M NaHCO$_3$, and extracted with EtOAc (1×60 mL) and 9:1 DCM/MeOH (2×30 mL). The organic layers were combined, dried (Na$_2$SO$_4$), and concentrated to afford a thick clear amber oil. Flash chromatography of this residue (3:2 hexanes/EtOAc) afforded the title compound as a thick clear yellow syrup that was rubbed to a beige solid (2.37 g, 46% from 4-chloro-7-fluoroquinazoline). $^1$H-NMR (300 MHz, CDCl$_3$) δ 9.23 (s, 1H), 8.20 (dd, 1H), 7.67 (dd, 1H), 7.42 (ddd, 1H), 4.42-4.25 (br m, 2H), 3.65 (m, 1H), 2.96 (m, 2H), 2.14-1.83 (m, 4H), 1.49 (s, 1H). LC/MS (ESI): calcd mass 331.2, found 332.1 (MH)$^+$(weak).

c. 4-[7-(3-Methanesulfonylamino-propoxy)-quinazolin-4-yl]-piperidine-1-carboxylic acid tert-butyl ester

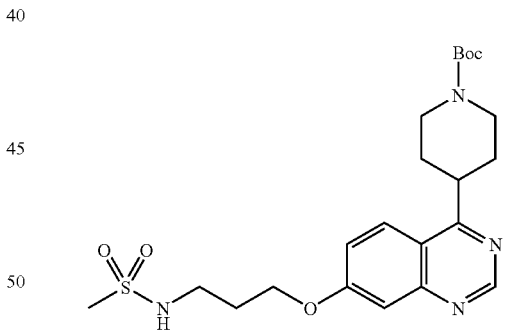

A mixture of 3-amino-propan-1-ol (37.9 mg, 505 μmol), t-BuOK (63.1 mg, 563 μmol), and DME (505 μL) was stirred for 5 min at rt until a homogeneous yellow solution resulted. Solid 4-(7-fluoro-quinazolin-4-yl)-piperidine-1-carboxylic acid tert-butyl ester (170.7 mg, 516 μmol), as prepared in the previous step, was added in one portion under air at "rt" (vial spontaneously warmed), and the resulting homogeneous amber solution was stirred at rt 1 h. The reaction was then diluted with DCM (1.0 mL) and stirred at 0° C. for 5 min before adding MsCl (48 μL, 620 μmol) dropwise with stirring at 0° C. over 1 min. After 1 min additional stirring at 0° C., the ice bath was removed and the hazy yellow solution was stirred at "rt" for 5 min. DIEA (94 μL, 568 μmol) was then added dropwise, and the reaction was stirred rt 2 days. The crude reaction was then loaded directly onto a flash silica column (4:3 DCM/acetone eluent) to provide the title compound as an off-white foam (186 mg, 79%). $^1$H—NMR (400 MHz, CDCl$_3$) δ 9.14 (s, 1H), 8.06 (d, 1H), 7.32 (d, 1H), 7.24 (m, 1H), 4.47 (br t, 1H), 4.32 (br s, 2H), 4.26 (t, 2H), 3.61 (m, 1H), 3.43 (q, 2H), 2.99-2.89 (m, 2H), 2.98 (s, 3H), 2.17 (pentet, 1H), 2.10-1.94 (m, 2H), 1.92-1.83 (m, 2H), 1.49 (s, 9H). LC/MS (ESI): calcd mass 464.2, found 465.2 (MH)$^+$.

EXAMPLE 13

4-{7-[3-(2-Oxo-pyrrolidin-1-yl)-propoxy]-quinazolin-4-yl}-piperidine-1-carboxylic acid tert-butyl ester

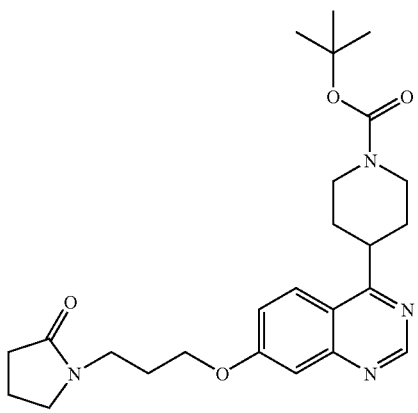

To a mixture of 4-(7-fluoro-quinazolin-4-yl)-piperidine-1-carboxylic acid tert-butyl ester 66.9 mg, 0.20 mmol), as prepared in Example 12b, and tert-BuOK (33.4 mg, 0.30 mmol) was added 1-(3-hydroxypropyl)-2-pyrrolidone (34.7 mg, 0.24 mmol) in anhydrous THF (3 mL). The mixture was stirred at 85° C. for 15 min and the solvent was evaporated under reduced pressure to give a light brown residue, which is used for the next step reaction without purification. $^1$H NMR (300 MHz, CDCl$_3$) δ 9. 10 (s, 1H), 8.03 (d, J=9.13 Hz, 1H), 7.26 (m, 1H), 7.23 (dd, J=9.05 and 2.43 Hz, 1H), 4.14 (t, J=6.08 Hz, 2H), 3.58 (m, 1H), 3.50 (t, J=6.60 Hz, 4H), 3.42 (t, J=6.98 Hz, 4H), 2.37 (t, J=8.45 Hz, 2H), 1.80-2.15 (m, 8H), 1.46 (s, 9H). LC-MS (ESI) calcd for C$_{25}$H$_{35}$N$_4$O$_4$ (MH$^+$) 455.3, found 455.2.

EXAMPLE 14

1-[2-(4-Piperidin-4-yl-quinazolin-7-yloxy)-ethyl]-pyrrolidin-2-one

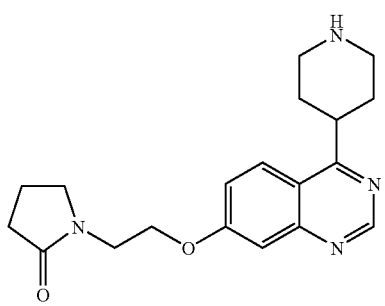

Prepared essentially as described in Example 11 using 1-(2-hydroxyethyl)-2-pyrrolidone. LC-MS (ESI) calcd for C$_{19}$H$_{25}$N$_4$N$_2$ (MH$^+$) 341.2, found 341.1.

EXAMPLE 15

6-[3-(4-Methyl-piperazin-1-yl)-propoxy]-4-piperidin-4-yl-quinazoline

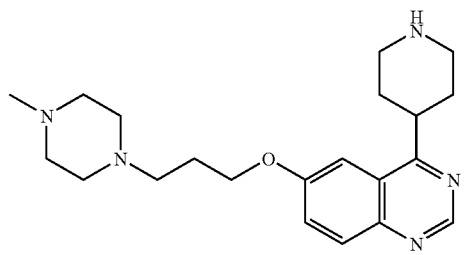

The title compound was prepared from 4-chloro-6-fluoro-quinazoline (WO 2005021500 A1, WO 2004071460 A2, WO 9609294 A1) essentially as described in Example 12, except 3-(4-Methyl-piperazin-1-yl)-propan-1-ol at 100° C. for 1 hr was used in place of 3-amino-propan-1-ol, and the use of methanesulfonyl chloride was omitted.

EXAMPLE 16

3-(4-Piperidin-4-yl-quinazolin-7-yloxy)-propan-1-ol

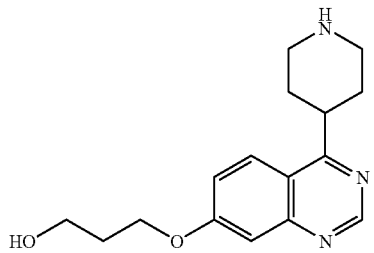

Prepared essentially as described in Example 5 using propane-1,3-diol in place of 3-hydroxypropylpiperidine.

EXAMPLE 17

7-(3-Methoxy-propoxy)-4-piperidin-4-yl-quinazoline

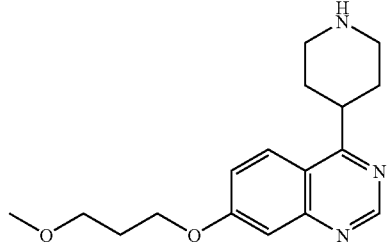

Prepared essentially as described in Example 5 using 3-methoxypropanol in place of 3-hydroxypropylpiperidine.

EXAMPLE 18

3-[2-(4-Piperidin-4-yl-quinazolin-7-yloxy)-ethyl]-oxazolidin-2-one

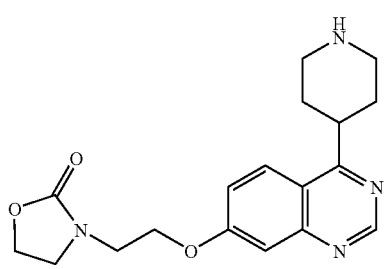

Prepared essentially as described in Example 13 using 3-(2-hydroxyethyl)-oxazolidin-2-one.

EXAMPLE 19

7-(1-Methyl-piperidin-4-ylmethoxy)-4-piperidin-4-yl-quinazoline

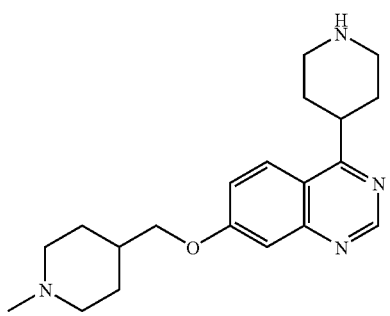

Prepared essentially as described in Example 13 using (1-methyl-piperidin-4-yl)-methanol.

EXAMPLE 20

1-{4-[2-(4-Piperidin-4-yl-quinazolin-7-yloxy)-ethyl]-piperazin-1-yl}-ethanone

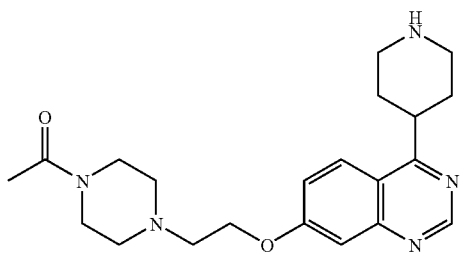

Prepared essentially as described in Example 13 using 1-[4-(2-hydroxy-ethyl)-piperazin-1-yl]-ethanone.

EXAMPLE 21

1-[3-(4-Piperidin-4-yl-quinazolin-6-yloxy)-propyl]-pyrrolidin-2-one

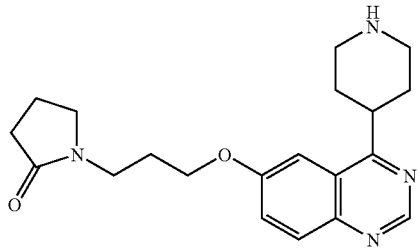

Prepared essentially as described in Example 15, using 1-(3-hydroxy-propyl)-pyrrolidin-2-one.

EXAMPLE 22

[3-(4-Methyl-piperazin-1-yl)-propyl]-(4-piperidin-4-yl-quinazolin-7-yl)-amine

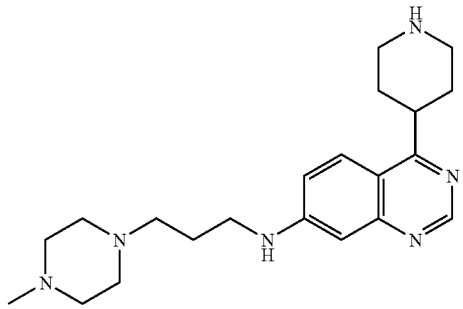

A mixture of 4-(3-aminopropyl)-1-methylpiperazine (0.1 mmol), Et$_3$N (0.1 mmol) and 4-(7-fluoro-quinazolin-4-yl)-piperidine-1-carboxylic acid tert-butyl ester (0.1 mmol), prepared as described in Example 12b, in DMF (1 mL) was stirred at 130° C. for 3 h. It was then diluted with water and extracted with EtOAc. The combined extracts were washed with water, brine, dried (anhydrous MgSO$_4$), filtered and concentrated in vacuo. The crude product was then treated with 3M HCl/MeOH (2 mL) and stirred at rt for 2 h, then concentrated in vacuo.

EXAMPLE 23

7-(4-Methyl-piperazin-1-yl)-4-piperidin-4-yl-quinazoline

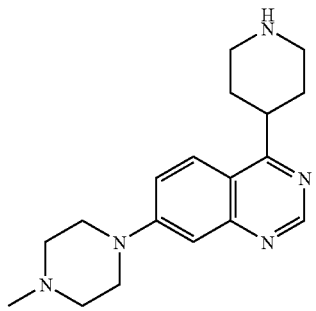

Prepared essentially as described in Example 22 using 1-methyl-piperazine in place of 4-(3-aminopropyl)-1-methylpiperazine.

EXAMPLE 24

4-[7-(3-[1,2,4]Triazol-4-yl-propoxy)-quinazolin-4-yl]-piperidine-1-carboxylic acid tert-butyl ester

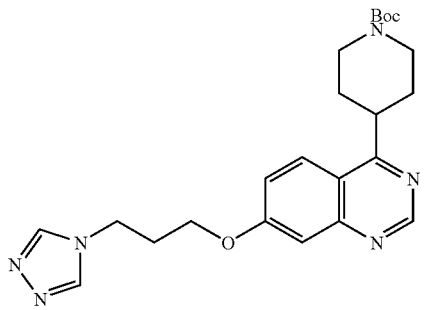

A mixture of 4-(7-fluoro-quinazolin-4-yl)-piperidin-1-carboxylic acid tert-butyl ester (31.6 mg, 95.5 μmol), as prepared in Example 12b, 3-[1,2,4]-triazol-4-yl-propan-1-ol (ChemPacific) (12.0 mg, 94.5 μmol), and KOtBu (11.7 mg, 104 μmol) in DME (100 μL) and DMSO (50 μL) was stirred at rt for 1 hr. The resulting homogeneous amber solution was partitioned with DCM (2 mL) and 0.5M sodium phosphate/pH 7 (2 mL). The organic layer was concentrated to provide the crude title compound. LC/MS (ESI): calcd mass 438.2, found 439.1 (MH)+.

EXAMPLE 25

3-Dimethylamino-4-[3-(4-piperidin-4-yl-quinazolin-7-yloxy)-propylamino]-cyclobut-3-ene-1,2-dione

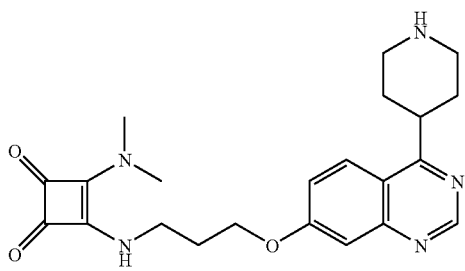

The title compound was prepared essentially as described for Example 12, except 3-Dimethylamino-4-methoxy-cyclobut-3-ene-1,2-dione [*Inorganic Chemistry* (1997), 36(14), 3096-3101] at 80° C. for 1 hr replaced methanesulfonyl chloride at rt.

EXAMPLE 26

Morpholine-4-carboxylic acid [3-(4-piperidin-4-yl-quinazolin-7-yloxy)-propyl]-amide

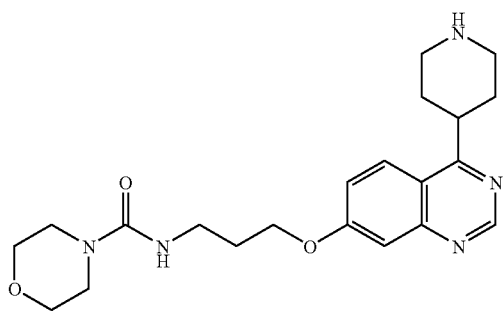

The title compound was prepared essentially as described in Example 25, except commercial 4-morpholinecarbonyl chloride replaced 3-Dimethylamino-4-methoxy-cyclobut-3-ene-1,2-dione.

EXAMPLE 27

7-[3-(4-Ethyl-piperazin-1-yl)-propoxy]-4-piperidin-4-yl-quinazoline

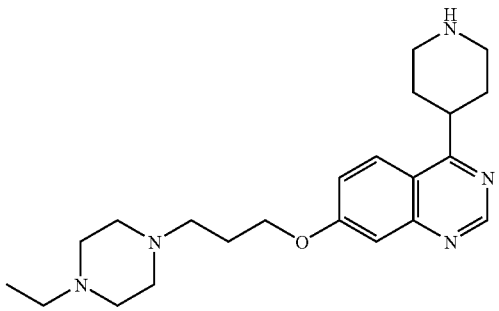

4-[7-(-Hydroxy-propoxy)-quinazolin-4-yl]-piperidine-1-carboxylic acid tert-butyl ester was prepared as described in Example 5 using propane-1,3-diol in place of 3-hydroxypropylpiperidine. To a solution of 4-[7-(-hydroxy-propoxy)-quinazolin-4-yl]-piperidine-1-carboxylic acid tert-butyl ester (0.3 mmol) in anhydrous DCM, was added Et₃N (0.6 mmol) and methanesulfonyl chloride (0.6 mmol) and the mixture was stirred at rt for 2 h. It was then washed with water (3×), dried over anhydrous MgSO₄, filtered and concentrated in vacuo to obtain 4-[7-(3-methanesulfonyloxy-propoxy)-quinazolin-4-yl]-piperidine-1-carboxylic acid tert-butyl ester. This (0.05 mmol) was dissolved in anhydrous dioxane together with 1-ethyl-piperazine (0.1 mmol) and the mixture was stirred at 100° C. overnight and then concentrated in vacuo, then diluted with water and extracted with DCM. The DCM extract was washed with water (3×), dried over anhydrous MgSO₄, filtered and concentrated in vacuo. To this was added 3M HCl/MeOH (1 mL) and the mixture was stirred at rt for 2 h and then concentrated in vacuo.

EXAMPLE 28

2-{4-[3-(4-Piperidin-4-yl-quinazolin-7-yloxy)-propyl]-piperazin-1-yl}-ethanol

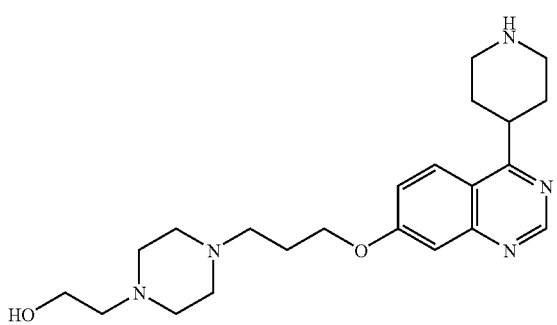

Prepared essentially as described in Example 27 using 2-piperazin-1-yl-ethanol in place of 1-ethyl-piperazine.

EXAMPLE 29

1-{4-[3-(4-Piperidin-4-yl-quinazolin-7-yloxy)-propyl]-piperazin-1-yl}-ethanone

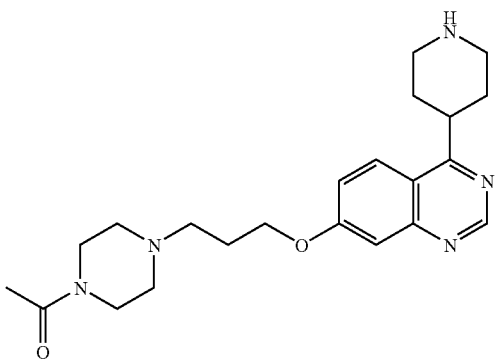

Prepared essentially as described in Example 27 using 1-acetyl-piperazine in place of 1-ethyl-piperazine.

EXAMPLE 30

7-[3-(4-Methanesulfonyl-piperazin-1-yl)-propoxy]-4-piperidin-4-yl-quinazoline

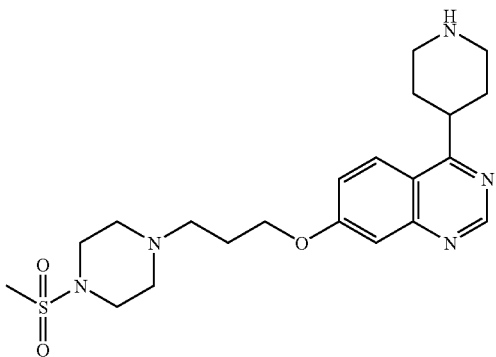

4-[7-(3-Methanesulfonyloxy-propoxy)-quinazolin-4-yl]-piperidine-1-carboxylic acid tert-butyl ester (0.1 mmol), prepared as described in Example 27, was dissolved in anhydrous dioxane together with piperazine (0.5 mmol) and the mixture was stirred at 100° C. overnight and then concentrated in vacuo, then diluted with water and extracted with DCM. The DCM extract was washed with water thrice, dried over anhydrous MgSO$_4$, filtered and concentrated in vacuo to obtain 4-[7-(3-piperazin-1-yl-propoxy)-quinazolin-4-yl]-piperidine-1-carboxylic acid tert-butyl ester. This (0.05 mmol) was dissolved in anhydrous DCM (1 mL) and treated with Et$_3$N (0.1 mmol) followed by methanesulfonyl chloride (0.1 mmol) and the mixture was stirred at rt overnight and then washed with water thrice, then dried over anhydrous MgSO$_4$, filtered and concentrated in vacuo. To this was added 3M HCl/MeOH (1 mL) and the mixture was stirred at rt for 2 h and then concentrated in vacuo.

EXAMPLE 31

(S)-{1-[3-(4-Piperidin-4-yl-quinazolin-7-yloxy)-propyl]-pyrrolidin-2-yl}-methanol

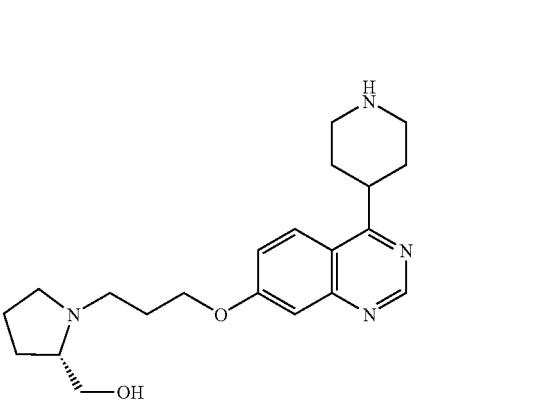

Prepared essentially as described in Example 27 using (S)-prolinol in place of 1-ethyl-piperazine.

EXAMPLE 32

4-[3-(4-Piperidin-4-yl-quinazolin-7-yloxy)-propyl]-piperazine-1-carboxylic acid dimethylamide

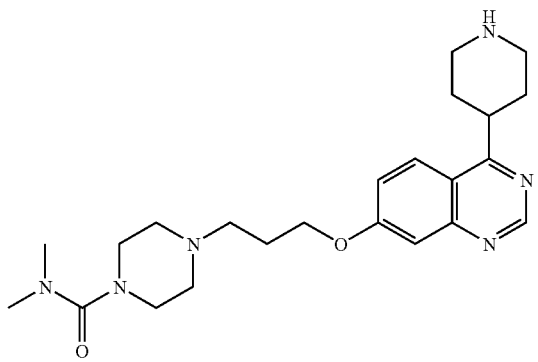

Prepared essentially as described in Example 30 using N,N-dimethylcarbamyl chloride in place of methanesulfonyl chloride.

EXAMPLE 33

4-Piperidin-4-yl-7-(3-pyrrolidin-1-yl-propoxy)-quinazoline

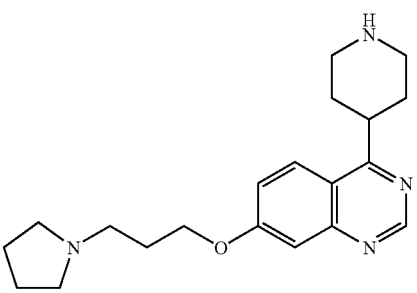

Prepared essentially as described in Example 27 using pyrrolidine in place of 1-ethyl-piperazine.

EXAMPLE 34

7-[3-(4-Methyl-[1,4]diazepan-1-yl)-propoxy]-4-piperidin-4-yl-quinazoline

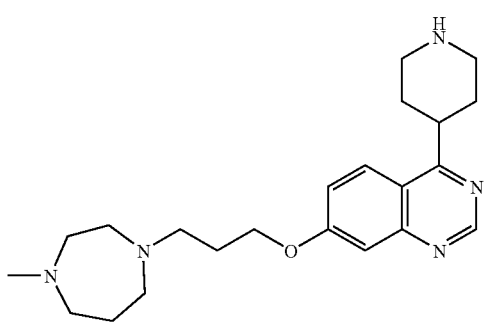

Prepared essentially as described in Example 27 using 1-methyl-[1,4]diazepane in place of 1-ethyl-piperazine.

EXAMPLE 35

4-[7-(R)-3-Hydroxy-pyrrolidin-1-yl)-quinazolin-4-yl]-piperidine-1-carboxylic acid tert-butyl ester

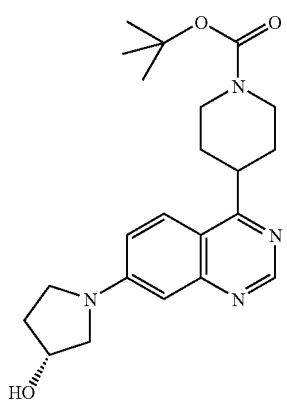

A mixture of 4-(7-fluoro-quinazolin-4-yl)-piperidine-1-carboxylic acid tert-butyl ester (34.9 mg, 0.105 mmol), which was prepared as described in Example 12b, and (R)-(+)-3-pyrrolidinol (32 mg, 0.368 mmol) in DMSO (0.4 mL) was heated at 120° C. with stirring for 40 min. It was partitioned between ethyl acetate and water, the combined organic extracts were washed with brine, dried over $Na_2SO_4$ and evaporated to afford almost pure product (40 mg, 95.7%). $^1$H NMR (CDCl$_3$) δ 8.97 (s, 1H), 7.96 (d, J=9.39 Hz, 1H), 7.01 (dd, J=9.33 and 2.45 Hz, 1H), 6.88 (d, J=2.19 Hz, 1H), 4.71 (m, 1H), 4.32 (m, 2H), 3.67 (m, 2H), 3.58 (m, 1H), 3.51 (m, 2H), 2.93 (m, 2H), 1.80-2.28 (6H), 1.49 (s, 9H). Calcd for $C_{22}H_{31}N_4O_3$ (MH+) 399.2, found 399.0.

EXAMPLE 36

7-(1-Methyl-piperidin-4-yloxy)-4-piperidin-4-yl-quinazoline

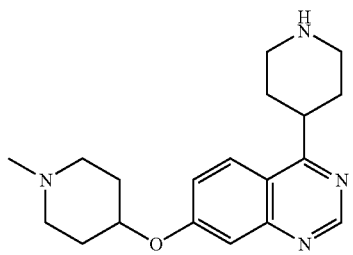

Prepared essentially as described in Example 13 using 1-methyl-piperidin-4-ol.

EXAMPLE 37

(S)-1-(4-Piperidin-4-yl-quinazolin-7-yl)-pyrrolidin-3-ol

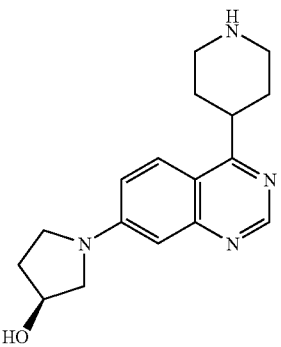

Prepared essentially as described in Example 35, using (S)-(+)-3-pyrrolidinol.

EXAMPLE 38

(R)-7-(2-Methoxymethyl-pyrrolidin-1-yl)-4-piperidin-4-yl-quinazoline

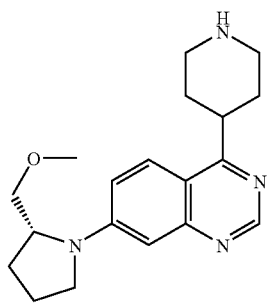

Prepared essentially as described in Example 35 using (R)-2-(methoxymethyl)pyrrolidine.

EXAMPLE 39

6-(4-Methyl-piperazin-1-yl)-4-piperidin-4-yl-quinazoline

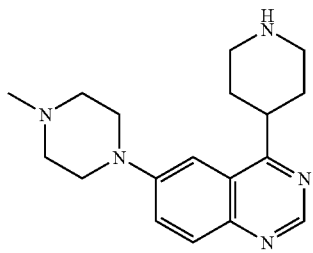

Prepared essentially as described in Example 15, using 1-methyl-piperazine.

EXAMPLE 40

(R)-[1-(4-Piperidin-4-yl-quinazolin-7-yl)-pyrrolidin-2-yl]-methanol

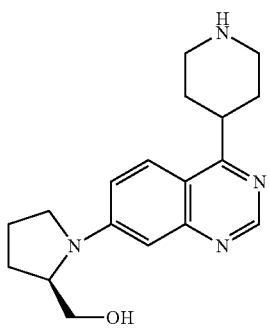

Prepared essentially as described in Example 35 using (R)-2-pyrrolidinemethanol.

EXAMPLE 41

7-(4-Ethyl-piperazin-1-yl)-4-piperidin-4-yl-quinazoline

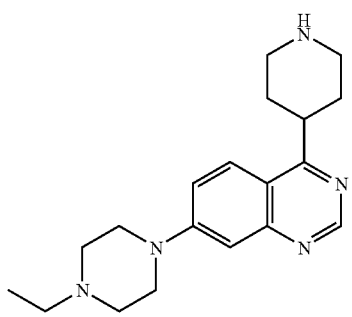

Prepared essentially as described in Example 12 using 1-ethyl-piperazine.

EXAMPLE 42

2-[4-(4-Piperidin-4-yl-quinazolin-7-yl)-piperazin-1-yl]-ethanol

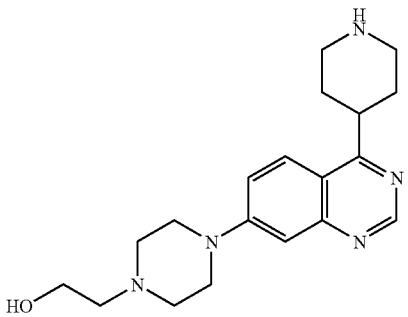

Prepared essentially as described in Example 12 using 1-(2-hydroxyethyl)-piperazine.

EXAMPLE 43

7-(4-Methyl-[1,4]diazepan-1-yl)-4-piperidin-4-yl-quinazoline

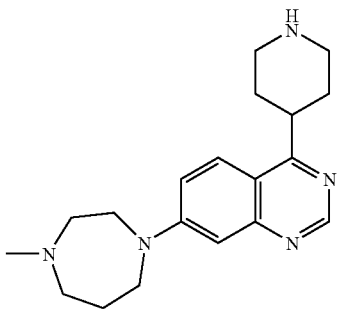

Prepared essentially as described in Example 12 using 1-methyl-[1,4]diazepane in place of 1-methyl-piperazine.

EXAMPLE 44

(S)-[1-(4-Piperidin-4-yl-quinazolin-7-yl)-pyrrolidin-2-yl]-methanol

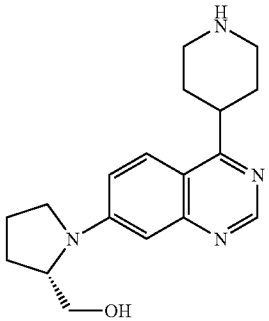

Prepared essentially as described in Example 35 using (S)-2-pyrrolidinemethanol.

EXAMPLE 45

4-(7-piperazin-1-yl-quinazolin-4-yl)-piperidine-1-carboxylic acid tert-butyl ester

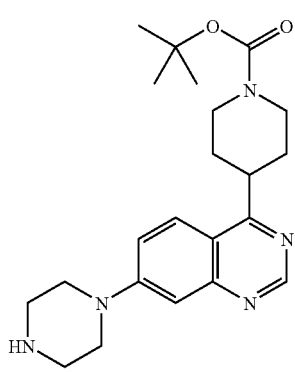

A mixture of piperazine (5 mmol) and 4-(7-fluoro-quinazolin-4-yl)-piperidine-1-carboxylic acid tert-butyl ester (1 mmol) in DMSO (1 mL) was stirred at 120° C. for 1 h. It was then diluted with water and extracted with DCM. The combined extracts were washed with water, brine, dried (anhydrous MgSO4), filtered and concentrated in vacuo to obtain 4-(7-piperazin-1-yl-quinazolin-4-yl)-piperidine-1-carboxylic acid tert-butyl ester.

EXAMPLE 46

2-(9H-Fluoren-9-yl)-1-[4-(4-piperidin-4-yl-quinazolin-7-yl)-piperazin-1-yl]-ethanone

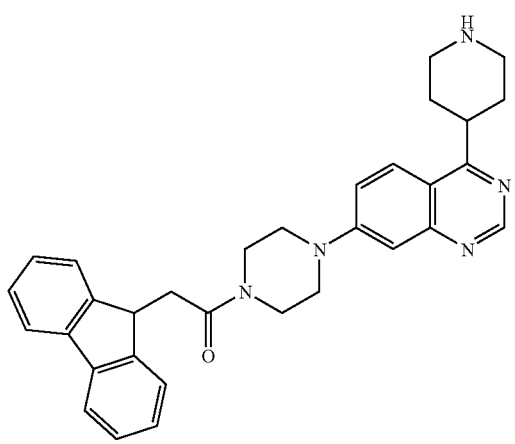

4-(7-Piperazin-1-yl-quinazolin-4-yl)-piperidine-1-carboxylic acid tert-butyl ester (Example 45, 0.1 mmol) was dissolved in anhydrous DCM (1 mL) and treated with Et₃N (0.2 mmol) followed by 9-fluorenylmethyl chloroformate (FMOC-Cl, 0.2 mmol) and the mixture was stirred at rt overnight and then washed with water thrice, then dried over anhydrous MgSO₄, filtered and concentrated in vacuo. To this was then added 3M HCl/MeOH (2 mL) and stirred at rt for 2 h and then concentrated in vacuo.

EXAMPLE 47

1-[4-(4-Piperidin-4-yl-quinazolin-7-yl)-piperazin-1-yl]-ethanone

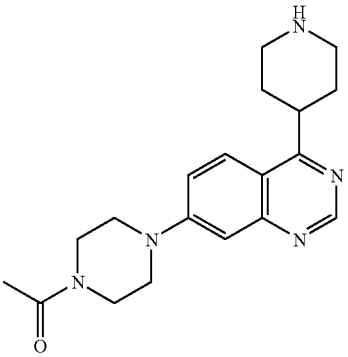

Prepared essentially as described in Example 46 using acetyl chloride in place of FMOC-Cl.

EXAMPLE 48

7-(4-Methanesulfonyl-piperazin-1-yl)-4-piperidin-4-yl-quinazoline

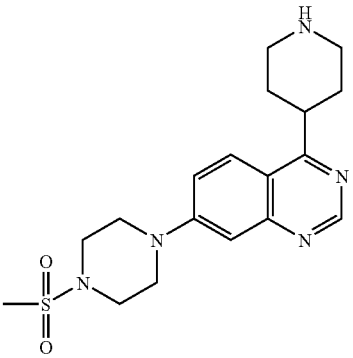

Prepared essentially as described in Example 46 using methanesulfonyl chloride in place of FMOC-Cl.

EXAMPLE 49

4-(4-Piperidin-4-yl-quinazolin-7-yl)-piperazine-1-carboxylic acid dimethylamide

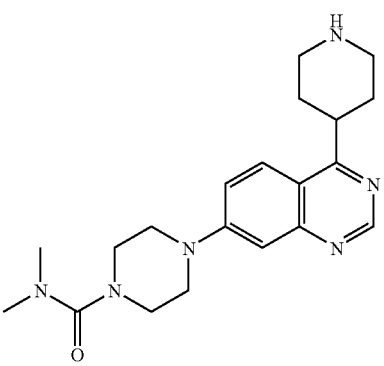

Prepared essentially as described in Example 46 using N,N-dimethylcarbamoyl chloride in place of FMOC-Cl.

EXAMPLE 50

2-Dimethylamino-1-[4-(4-piperidin-4-yl-quinazolin-7-yl)-piperazin-1-yl]-ethanone

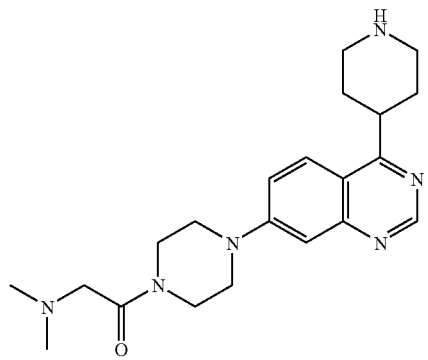

Prepared essentially as described in Example 46 using N,N-dimethylaminoacetyl chloride in place of FMOC-Cl.

EXAMPLE 51

7-Morpholin-4-yl-4-piperidin-4-yl-quinazoline

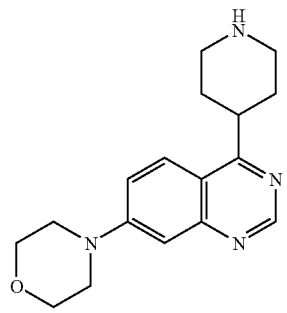

Prepared essentially as described in Example 12 using morpholine in place of 1-methyl-piperazine.

EXAMPLE 52

(2-Methanesulfonyl-ethyl)-(4-piperidin-4-yl-quinazolin-7-yl)-amine

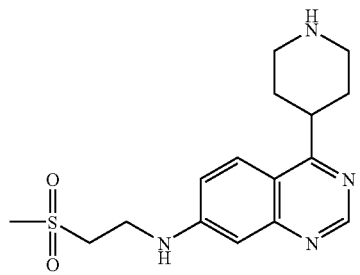

Prepared essentially as described in Example 35 using 2-methanesulfonyl-ethylamine.

EXAMPLE 53

(R)-Dimethyl-[1-(4-piperidin-4-yl-quinazolin-7-yl)-pyrrolidin-3-yl]-amine

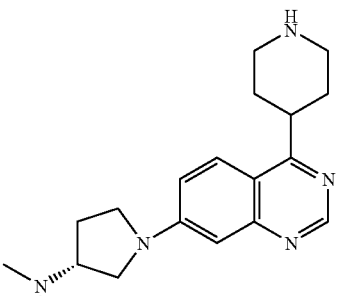

Prepared essentially as described in Example 35 using (3R)-(+)-3-(dimethylaminopyrrolidine).

EXAMPLE 54

(S)-7-(1-Methyl-pyrrolidin-2-ylmethoxy)-4-piperidin-4-yl-quinazoline

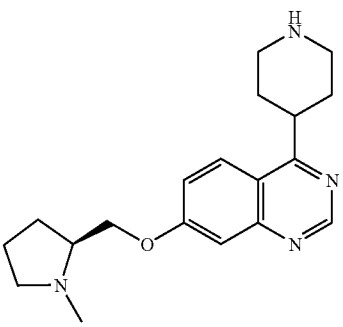

Prepared essentially as described in Example 12 using (S)-(-)-1-methyl-2-pyrrolidinemethanol.

EXAMPLE 55

(S)-{1-[2-(4-Piperidin-4-yl-quinazolin-7-yloxy)-ethyl]-pyrrolidin-2-yl}-methanol

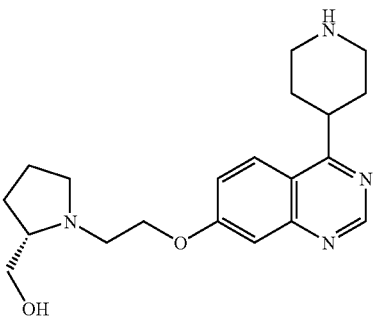

a. 4-[7-(2-Hydroxy-ethoxy)-quinazolin-4-yl]-piperidine-1-carboxylic acid tert-butyl ester

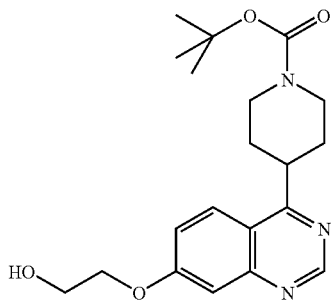

4-(7-Fluoro-quinazolin-4-yl)-piperidine-1-carboxylic acid tert-butyl ester (97.4 mg, 0.294 mmol), which was prepared as described in Example 12b, was added to ethane-1,2-diol (2.98 g, 48.01 mmol) and the suspension was heated to 90° C. to allow the starting material totally dissolved in ethane-1,2-diol. KOH (130.7 mg) was added and the mixture was stirred at 120° C. for 2 h. It was partitioned between ethyl acetate and water and the combined organic extracts were washed with brine, dried over $Na_2SO_4$ and evaporated to afford the product as a white solid (90 mg, 82%). $^1$H NMR ($CDCl_3$) δ 9.12 (s, 1H), 8.05 (d, J=9.27 Hz, 1H), 7.32 (d, J=2.46 Hz, 1H), 7.28 (dd, J=9.21 and 2.54 Hz, 1H), 4.31 (br, 1H), 4.26 (t, J=4.01 Hz, 2H), 4.20 (m, 1H), 4.06 (t, J=4.67 Hz, 2H), 3.83 (m, 1H), 3.60 (m, 1H), 2.93 (m, 2H), 1.80-2.11 (4H), 1.47 (s, 9H). Calcd for $C_{20}H_{28}N_3O_4$ (MH+) 374.2, found 374.2.

b. 4-[7-(2-Methanesulfonyloxy-ethoxy)-quinazolin-4-yl]-piperidine-1-carboxylic acid tert-butyl ester

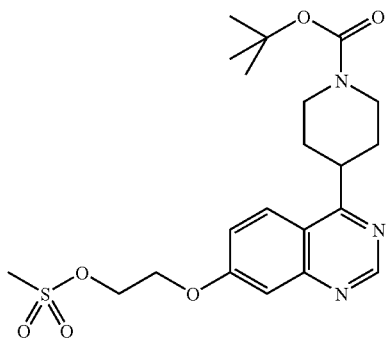

To a mixture of 4-[7-(2-hydroxy-ethoxy)-quinazolin-4-yl]-piperidine-1-carboxylic acid tert-butyl ester (90 mg, 0.24 mmol) and DIPEA (167.2 μL) in $CH_2Cl_2$ (5 mL) was added MsCl (37.2 μL). The reaction mixture was stirred for 4 h and the solvents were evaporated. The residue was purified by flash column chromatography on silica gel (EtOAc as eluent) to afford almost pure product. $^1$H NMR ($CDCl_3$) δ 9.15 (s, 1H), 8.09 (d, J=9.33 Hz, 1H), 7.33 (d, J=2.44 Hz, 1H), 7.29 (dd, J=9.18 and 2.59 Hz, 1H), 4.66 (t, J=4.29 Hz, 2H), 4.42 (t, J=4.39 Hz, 2H), 4.33 (m, 2H), 3.61 (m, 1H), 3.11 (s, 3H), 2.94 (m, 2H), 1.83-2.10 (4H), 1.48 (s, 9H). Calcd for $C_{21}H_{30}N_3O_6S$ (MH+) 452.2, found 452.2.

c. (S)-{1-[2-(4-Piperidin-4-yl-quinazolin-7-yloxy)-ethyl]-pyrrolidin-2-yl}-methanol

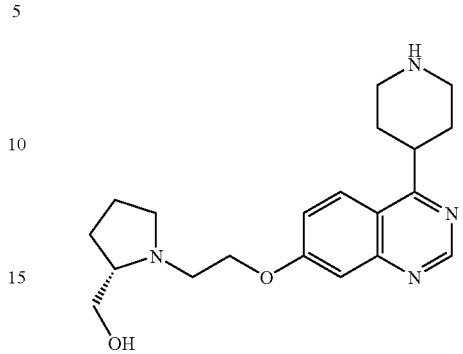

To a solution of 4-[7-(2-methanesulfonyloxy-ethoxy)-quinazolin-4-yl]-piperidine-1-carboxylic acid tert-butyl ester (40.6 mg, 0.09 mmol) in DMSO (0.4 mL) was added (S)-(+)-2-pyrrolidinemethanol (90.9 mg, 0.9 mmol). The mixture was stirred at 120° C. overnight and subsequently partitioned between EtOAc and water. The combined organic extracts were washed with brine, dried over $Na_2SO_4$ and evaporated. The residue was treated with 50% $TFA/CH_2Cl_2$ (8 mL) for 2 h, the solvents ($TFA/CH_2Cl_2$) were removed under reduced pressure to provide the desired product. LC-MS (ESI) calcd for $C_{20}H_{29}N_4O_2$ (MH+) 357.2, found 357.2.

EXAMPLE 56

(R)-4-[7-(1-Acetyl-pyrrolidin-3-yloxy)-quinazolin-4-yl]-piperidine-1-carboxylic acid tert-butyl ester

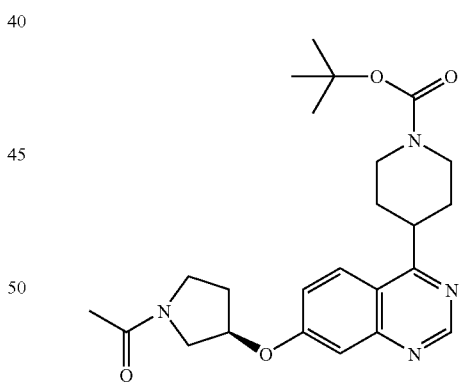

To a solution of KOt-Bu (55.1 mg, 0.47 mmol) in THF (1 mL) was added (R)-hydroxypyrrolidine (37.7 mg, 0.43 mmol), followed by 4-(7-fluoro-quinazolin-4-yl)-piperidine-1-carboxylic acid tert-butyl ester (110.3 mg, 0.33 mmol), which was prepared as described in Example 12b, in THF (1 mL). The mixture was stirred for 1 h at room temperature, quenched with $(CH_3CO)_2O$. The mixture was then partitioned between EtOAc and water. The organic extracts were washed with brine and evaporated and the residue was used for the next step reaction without further purification. LC/MS for $C_{24}H_{33}N_4O_4$ (MH+) 440.2, found 440.5.

EXAMPLE 57

1-(4-Piperidin-4-yl-quinazolin-7-yl)-piperidine-4-carboxylic acid methylamide

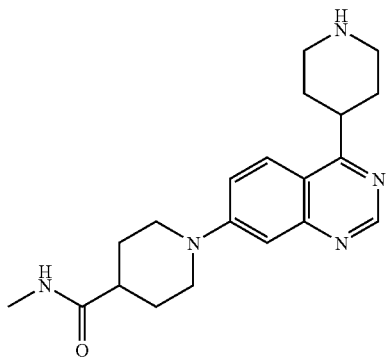

Prepared essentially as described in Example 35 using piperidine-4-carboxylic acid methylamide.

EXAMPLE 58

7-[2-(4-Methyl-piperazin-1-yl)-ethoxy]-4-piperidin-4-yl-quinazoline

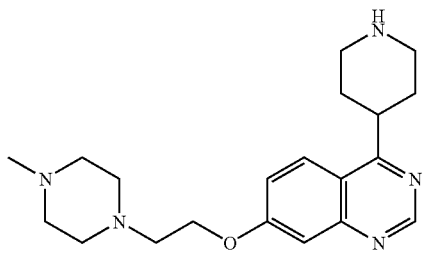

Prepared essentially as described in Example 55 using 1-methyl-piperazine. LC-MS (ESI) calcd for $C_{20}H_{30}N_5O$ (MH$^+$) 356.2, found 356.1.

EXAMPLE 59

(S)-1-[2-(4-Piperidin-4-yl-quinazolin-7-yloxymethyl)-pyrrolidin-1-yl]-ethanone

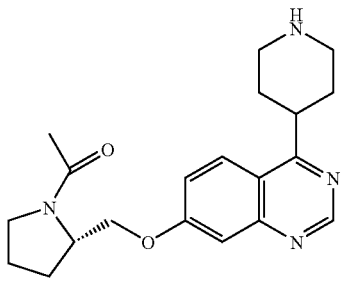

Prepared essentially as described in Example 56, using (S)-(+)-2-pyrrolidinemethanol.

EXAMPLE 60

1-[4-(4-Piperidin-4-yl-quinazolin-7-yloxymethyl)-piperidin-1-yl]-ethanone

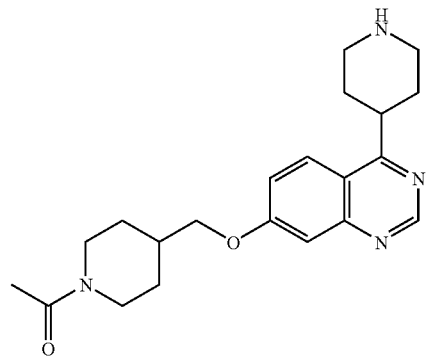

Prepared essentially as described in Example 56, using piperidin-4-yl-methanol. LC-MS (ESI) calcd for $C_{21}H_{29}N_4O_2$ (MH$^+$) 369.2, found 369.2.

EXAMPLE 61

4-[7-(1-Acetyl-azetidin-3-yloxy)-quinazolin-4-yl]-piperidine-1-carboxylic acid tert-butyl ester

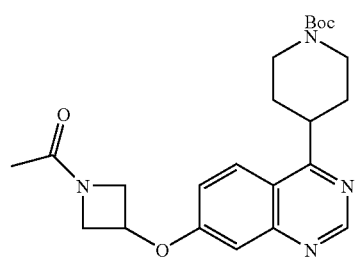

a. 4-[7-(Azetidin-3-yloxy)-quinazolin-4-yl]-piperidine-1-carboxylic acid tert-butyl ester

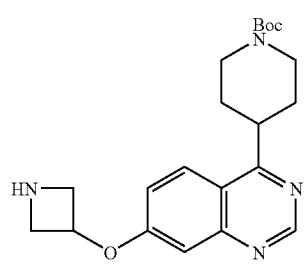

A mixture of Azetidin-3-ol hydrochloride (Oakwood) (461 mg, 4.21 mmol), KOtBu (1.02 g, 9.11 mmol), and dry DMSO (4.2 mL) was stirred at rt for 30 min until a translucent solution resulted. Then 4-(7-fluoro-quinazolin-4-yl)-piperidine-1-carboxylic acid tert-butyl ester (1.46 g, 4.41 mmol), as prepared in Example 12b, was added, and the resulting opaque orange mixture (no visible precipitate) was stirred at rt for 3.5 hr. The reaction was then shaken with water (40 mL) and extracted with DCM (1×20 mL) and 9:1 DCM/MeOH (1×20 mL). The combined organic layers were washed with 0.2 M K$_2$CO$_3$ (3×20 mL), dried (Na$_2$SO$_4$), and concentrated to give 1.715 g of the title compound as an off-white solid ("106%" crude yield). LC/MS (ESI): calcd mass 384.2, found 385.3 (MH)$^+$.

b. 4-[7-(1-Acetyl-azetidin-3-yloxy)-quinazolin-4-yl]-piperidine-1-carboxylic acid tert-butyl ester

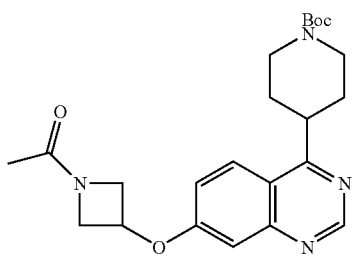

Acetic anhydride (66 µL, 703 µmol) was added dropwise with stirring at rt to a mixture of 4-[7-(Azetidin-3-yloxy)-quinazolin-4-yl]-piperidine-1-carboxylic acid tert-butyl ester (180 mg, 469 µmol), as prepared in the previous step, in DCM (1.0 mL). The resulting homogeneous yellow solution was stirred overnight, and was then partitioned with DCM (3 mL) and IM NaHCO$_3$ (1×4 mL). The organic layer was dried (Na$_2$SO$_4$), concentrated, and purified by silica flash chromatography (8:2 DCM/acetone/3% DMEA eluent) to afford the title compound as a white crystalline film (88.3 mg, 44% over two steps). LC/MS (ESI): calcd mass 426.2, found 426.9 (MH)$^+$.

EXAMPLE 62

4-[7-(1-Methanesulfonyl-azetidin-3-yloxy)-quinazolin-4-yl]-piperidine-1-carboxylic acid tert-butyl ester

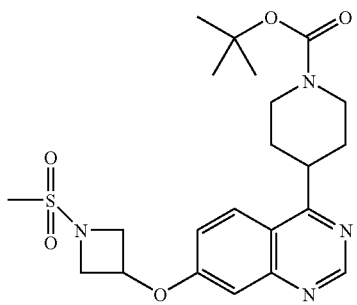

The title compound was prepared essentially as described for Example 61b, using methanesulfonyl chloride and 1.5 equivalents of TEA in place of acetic anhydride.

EXAMPLE 63

4-[7-(2-Morpholin-4-yl-2-oxo-ethoxy)-quinazolin-4-yl]-piperidine-1-carboxylic acid tert-butyl ester

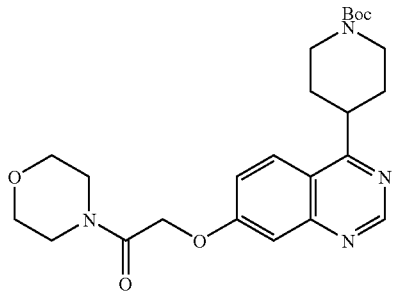

A mixture of morpholine (107.4 mg, 1.23 mmol) and methyl glycolate (77.5 mg, 860 µmol) was stirred at 150° C. for 3 hr. The resulting homogeneous clear amber oil was taken up in toluene (2×2 mL) with repeated rotary evaporation to remove methanol. The residue was taken up in dry THF (860 µL) and KOtBu was added (113 mg, 1.01 mmol). The mixture was stirred at 100° C. for 5-10 min until a brown slurry formed with no visible chunks. The mixture was then allowed to cool to rt, 4-(7-fluoro-quinazolin-4-yl)-piperidine-1-carboxylic acid tert-butyl ester (302 mg, 912 µmol), as prepared in Example 12b, was added, and the resulting nearly homogeneous reddish-brown solution was stirred at rt for 1 hr, at which point the reaction solidified into a paste. The reaction was taken up in DCM (4 mL) and washed with 1M NaHCO$_3$ (1×2 mL) and IM NaH$_2$PO$_4$ (1×2 mL), and the organic layer was dried (Na$_2$SO$_4$) and concentrated. The residue was purified by silica flash chromatography (9:1 DCM/acetone→8:2→8:2 DCM/acetone/3% DMEA eluent) to provide the title compound as a pale yellow oil (94.8 mg, 24% over two steps). LC/MS (ESI): calcd mass 456.2, found 457.3 (MH)$^+$.

EXAMPLE 64

4-(7-Azetidin-1-yl-quinazolin-4-yl)-piperidine-1-carboxylic acid tert-butyl ester

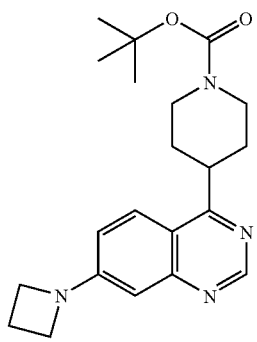

Prepared essentially as Example 35 using azetidine.

EXAMPLE 65

4-[7-(Pyridin-3-yloxy)-quinazolin-4-yl]-piperidine-1-carboxylic acid tert-butyl ester

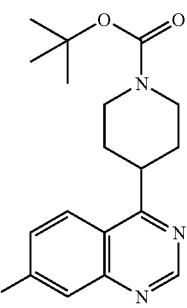

Prepared essentially as Example 13 using pyridin-3-ol.

EXAMPLE 66

4-[7-(2-Hydroxy-ethylamino)-quinazolin-4-yl]-piperidine-1-carboxylic acid tert-butyl ester

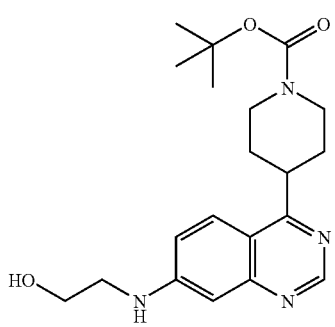

Prepared essentially as Example 35 using 2-amino-ethanol.

EXAMPLE 67

4-[7-(2-Oxo-oxazolidin-3-yl)-quinazolin-4-yl]-piperidine-1-carboxylic acid tert-butyl ester

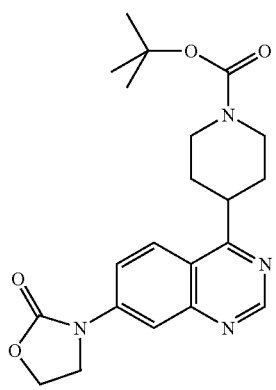

To a solution of 4-(7-fluoro-quinazolin-4-yl)-piperidine-1-carboxylic acid tert-butyl ester (139.6 mg, 0.42 mmol), which was prepared as described in Example 12b, in DMSO (0.8 mL) was added ethanolamine (256.2 mg, 4.2 mmol). The mixture was stirred at 120° C. overnight and subsequently partitioned between EtOAc and water. The combined organic extracts were washed with brine, dried over $Na_2SO_4$ and evaporated. The residue was re-dissolved in $CH_2Cl_2$ (4 mL), treated with $COCl_2$ (1 mL of 1M solution in toluene) and TEA (200 mg). The mixture was partitioned between $CH_2Cl_2$ and water. The $CH_2Cl_2$ extracts were evaporated and the residue was purified by flash column chromatography on silica gel (hexanes/EtOAc 1:1, v/v) to afford the desired product. LC/MS for $C_{21}H_{27}N_4O_4$ (MH+) 399.2, found 399.2.

EXAMPLE 68

(R)-4-[7-(1-Methanesulfonyl-pyrrolidin-3-yloxy)-quinazolin-4-yl]-piperidine-1-carboxylic acid tert-butyl ester

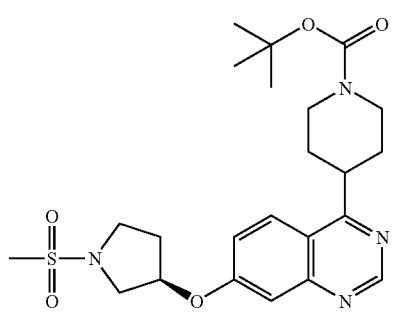

Prepared essentially as Example 56 with the sole exception that the intermediate generated was quenched with MsCl.

EXAMPLE 69

4-[7-(2-Oxo-imidazolidin-1-yl)-quinazolin-4-yl]-piperidine-1-carboxylic acid tert-butyl ester

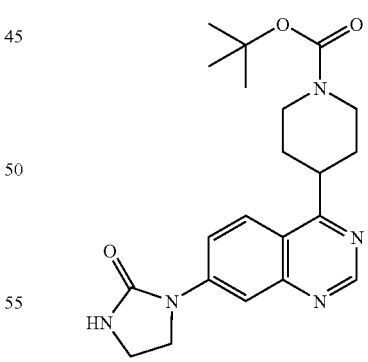

To a mixture of 4-(7-fluoro-quinazolin-4-yl)-piperidine-1-carboxylic acid tert-butyl ester (458 mg, 1.38 mmol), which was prepared as described in Example 12b, and (2-aminoethyl)-carbamic acid benzyl ester hydrochloride (446 mg, 1.93 mmol) in DMSO (1.0 mL) was added $K_2CO_3$ (1.52 g, 11.04 mmol). The mixture was stirred at 115° C. overnight and subsequently partitioned between EtOAc and water. The combined organic extracts were washed with brine, dried over Na$_2$SO$_4$ and evaporated. The residue was purified by flash column chromatography on silica gel (EtOAc as eluent) to afford the desired product as a white solid (400 mg, 73%). $^1$H NMR (CDCl$_3$) δ 9.13 (s, 1H), 8.69 (dd, J=9.40 and 2.35 Hz, 1H), 8.08 (d, J=9.53 Hz, 1H), 7.42 (d, J=2.33 Hz, 1H), 5.25 (br, 1H), 4.31 (m, 2H), 4.09 (t, J=8.21 Hz, 2H), 3.69 (t, J=8.14 Hz, 2H), 3.63 (m, 1H), 2.95 (m, 2H), 1.77-2.04 (4H), 1.48 (s, 9H). Calcd for C$_{21}$H$_{28}$N$_5$O$_3$ (MH+) 398.3, found 398.3.

EXAMPLE 70

4-(7-Pyrrolidin-1-yl-quinazolin-4-yl)-piperidine-1-carboxylic acid tert-butyl ester

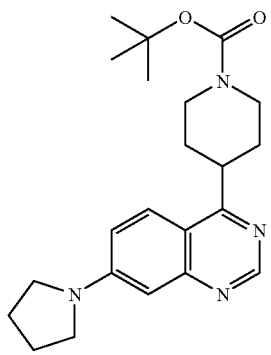

Prepared essentially as described in Example 12 using pyrrolidine in place of 1-methyl-piperazine.

EXAMPLE 71

4-(7-Imidazol-1-yl-quinazolin-4-yl)-piperidine-1-carboxylic acid tert-butyl ester

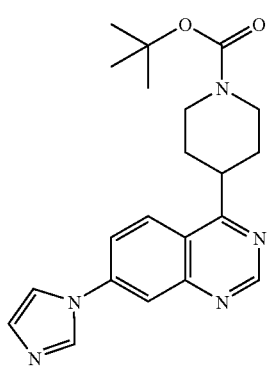

Prepared essentially as described in Example 12 using imidazole in place of 1-methyl-piperazine.

EXAMPLE 72

4-(7-Thiomorpholin-4-yl-quinazolin-4-yl)-piperidine-1-carboxylic acid tert-butyl ester

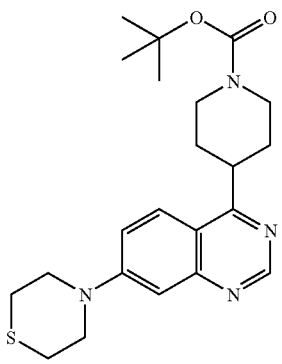

Prepared essentially as described in Example 12 using thiomorpholine in place of 1-methyl-piperazine.

EXAMPLE 73

4-[7-(3-Oxo-piperazin-1-yl)-quinazolin-4-yl]-piperidine-1-carboxylic acid tert-butyl ester

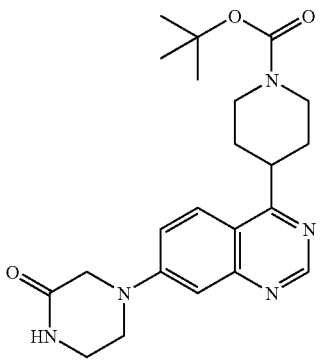

Prepared essentially as described in Example 12 using piperazin-2-one in place of 1-methyl-piperazine. LC-MS (ESI) calcd for C$_{22}$H$_{29}$N$_5$O$_3$ (MH$^+$) 412.2, found 412.3.

EXAMPLE 74

4-[7-(4-Methyl-3-oxo-piperazin-1-yl)-quinazolin-4-yl]-piperidine-1-carboxylic acid tert-butyl ester

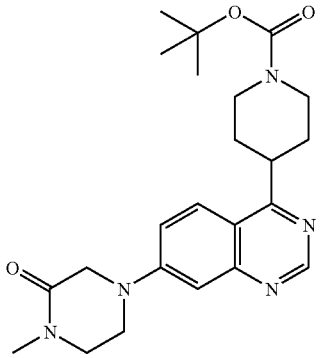

Prepared essentially as described in Example 12 using 1-methyl-piperazin-2-one in place of 1-methyl-piperazine.

EXAMPLE 75

4-{7-[4-(2-Methoxy-ethyl)-piperazin-1-yl]-quinazolin-4-yl}-piperidine-1-carboxylic acid tert-butyl ester

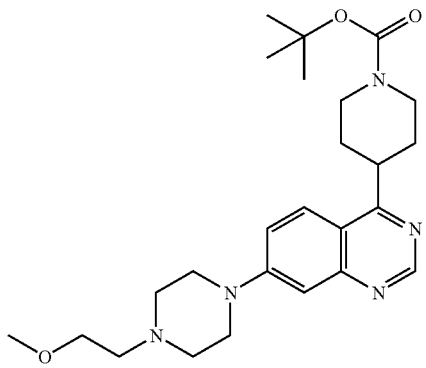

Prepared essentially as described in Example 12 using 1-(2-methoxyethyl)-piperazine in place of 1-methyl-piperazine

EXAMPLE 76

4-Piperidin-4-yl-7-(tetrahydro-pyran-4-ylmethoxy)-quinazoline

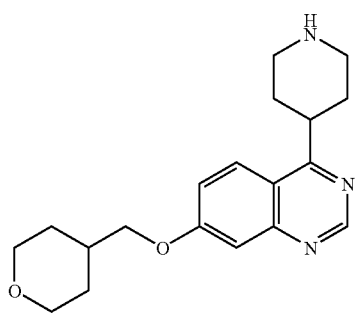

A mixture of (tetrahydro-pyran-4-yl)-methanol (0.2 mmol), KOtBu (0.2 mmol) and 4-(7-fluoro-quinazolin-4-yl)-piperidine-1-carboxylic acid tert-butyl ester (0.1 mmol), prepared as described in Example 12b, in DMSO (1 mL), was stirred at 80° C. for 1 h. It was then diluted with water and extracted with DCM. The combined extracts were washed with water, brine, dried with MgSO$_4$, filtered, and concentrated in vacuo. The crude product was then treated with 3M HCl/MeOH (2 mL) and stirred at rt for 2 h and then concentrated in vacuo.

EXAMPLE 77

4-Piperidin-4-yl-7-(tetrahydro-pyran-4-yloxy)-quinazoline

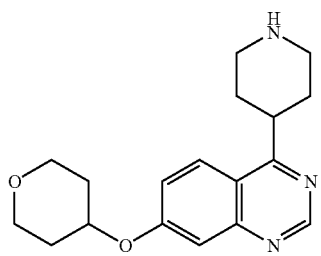

Prepared essentially as described in Example 76 using tetrahydro-pyran-4-ol in place of (tetrahydro-pyran-4-yl)-methanol.

EXAMPLE 78

(S)-4-Piperidin-4-yl-7-(tetrahydro-furan-3-yloxy)-quinazoline

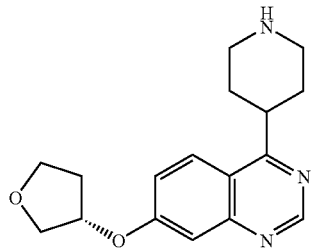

Prepared essentially as described in Example 76 using (S)-tetrahydro-furan-3-ol in place of (tetrahydro-pyran-4-yl)-methanol.

EXAMPLE 79

(R)-4-Piperidin-4-yl-7-(tetrahydro-furan-3-yloxy)-quinazoline

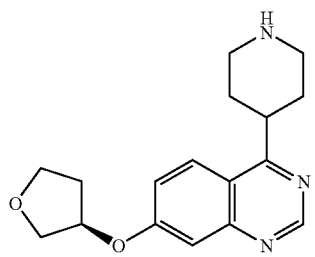

Prepared essentially as described in Example 76 using (R)-tetrahydro-furan-3-ol in place of (tetrahydro-pyran-4-yl)-methanol.

EXAMPLE 80

4-[7-(4-Pyridin-2-yl-piperazin-1-yl)-quinazolin-4-yl]-piperidine-1-carboxylic acid tert-butyl ester

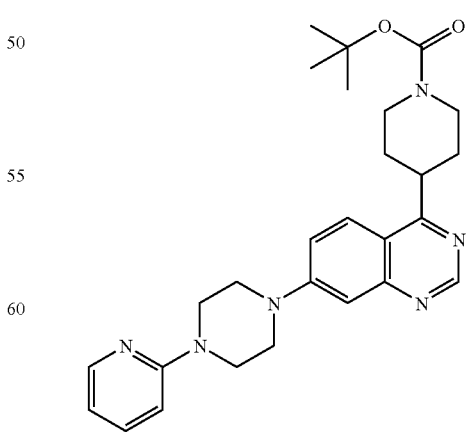

Prepared essentially as described in Example 23 using 1-pyridin-2-yl-piperazine in place of 1-methyl-piperazine.

EXAMPLE 81

4-[7-(4-Pyrimidin-2-yl-piperazin-1-yl)-quinazolin-4-yl]-piperidine-1-carboxylic acid tert-butyl ester

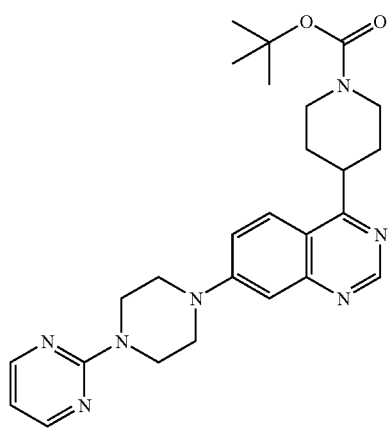

Prepared essentially as described in Example 23 using 1-pyrimidin-2-yl-piperazine in place of 1-methyl-piperazine.

EXAMPLE 82

4-[7-(4-Pyridin-4-yl-piperazin-1-yl)-quinazolin-4-yl]-piperidine-1-carboxylic acid tert-butyl ester

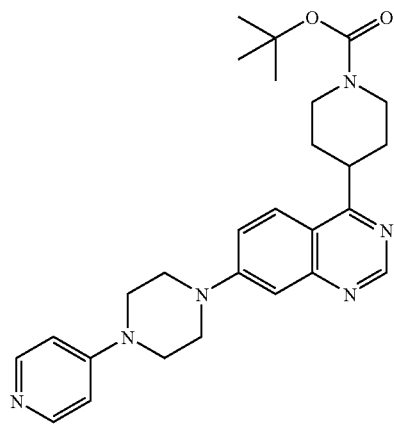

Prepared essentially as described in Example 23 using 1-pyridin-4-yl-piperazine in place of 1-methyl-piperazine.

EXAMPLE 83

4-[7-(4-Fluoro-piperidin-1-yl)-quinazolin-4-yl]-piperidine-1-carboxylic acid tert-butyl ester

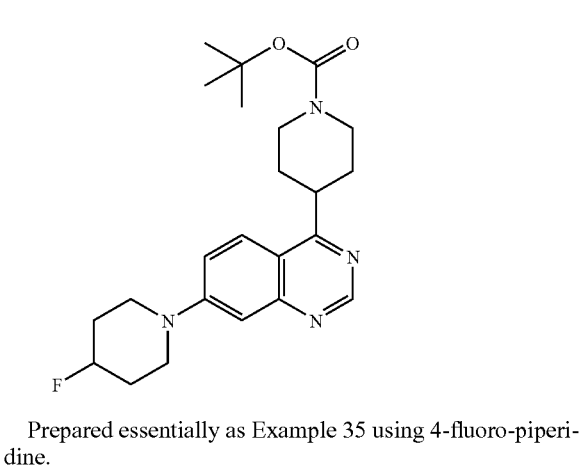

Prepared essentially as Example 35 using 4-fluoro-piperidine.

EXAMPLE 84

4-(4-Piperidin-4-yl-quinazolin-7-yl)-piperazine-1-carboxylic acid ethylamide

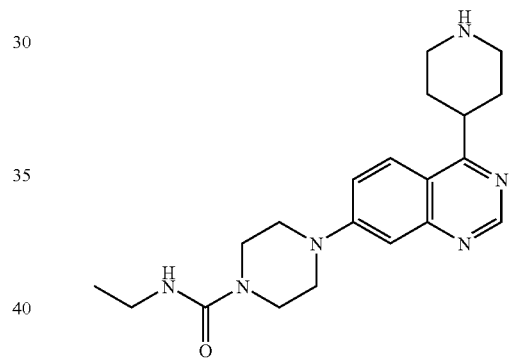

Prepared essentially as described in Example 46 using ethyl isocyanate in place of FMOC-Cl.

EXAMPLE 85

2-Methoxy-1-[4-(4-piperidin-4-yl-quinazolin-7-yl)-piperazin-1-yl]-ethanone

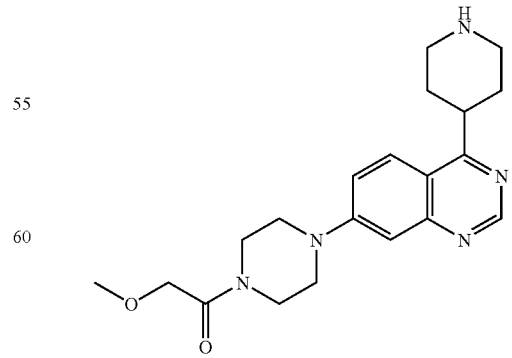

Prepared essentially as described in Example 46 using methoxyacetyl chloride in place of FMOC-Cl.

EXAMPLE 86

2-Hydroxy-1-[4-(4-piperidin-4-yl-quinazolin-7-yl)-piperazin-1-yl]-ethanone

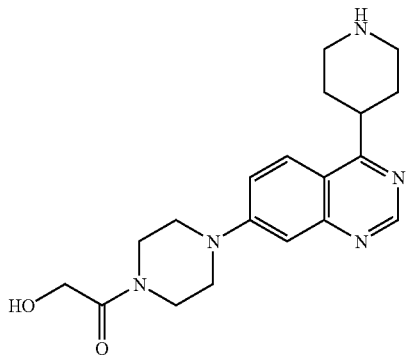

4-(7-Piperazin-1-yl-quinazolin-4-yl)-piperidine-1-carboxylic acid tert-butyl ester (0.1 mmol), prepared as described in Example 45, was added to a mixture of t-butoxyacetic acid (0.15 mmol) and PS-carbodiimide (0.2 mmol) in anhydrous DCM (2 mL). The mixture was shaken at rt overnight. It was then filtered and the resin washed with DCM. The combined filtrate and washings were concentrated in vacuo. To this was then added 3M HCl/MeOH (2 mL) and stirred at rt for 2 h and then concentrated in vacuo.

EXAMPLE 87

1-Methyl-4-[2-(4-piperidin-4-yl-quinazolin-7-yloxy)-ethyl]-piperazin-2-one

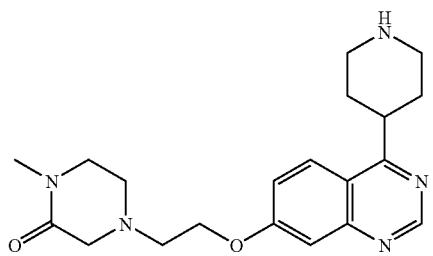

To a solution of 4-[7-(-hydroxy-ethoxy)-quinazolin-4-yl]-piperidine-1-carboxylic acid tert-butyl ester (0.5 mmol), prepared as described in Example 55a, in anhydrous DCM, was added Et₃N (1 mmol) and methanesulfonyl chloride (1 mmol) and the mixture was stirred at rt for 2 h. It was then washed with water (3×), dried over anhydrous MgSO₄, filtered and concentrated in vacuo to obtain crude 4-[7-(3-methanesulfonyloxy-ethoxy)-quinazolin-4-yl]-piperidine-1-carboxylic acid tert-butyl ester. This (0.1 mmol) was dissolved in anhydrous DMSO together with 1-methyl-piperazin-2-one (0.2 mmol) and the mixture was stirred at 100° C. for 2 h and then diluted with water and extracted with DCM. The DCM extract was washed with water (3×), dried over anhydrous MgSO₄, filtered and concentrated in vacuo. To this was added 3M HCl/MeOH (1 mL) and the mixture was stirred at rt for 2 h and then concentrated in vacuo.

EXAMPLE 88

6-Methoxy-4-piperidin-4-yl-quinazoline

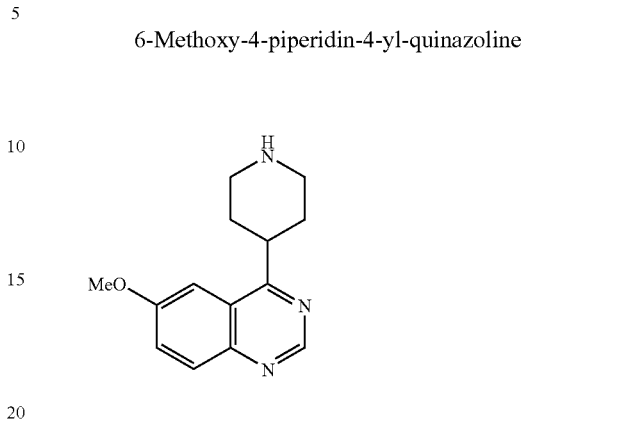

The title compound was prepared from 4-chloro-6-methoxyquinazoline (WO 2001032632 A2, WO 9609294 A1) essentially as described for Example 1, except the methyl ester intermediate was stirred in KOH/MeOH at 100° C. for 3 hr instead of 1 hr.

EXAMPLE 89

4-{7-[3-(1H-Tetrazol-5-yl)-propoxy]-quinazolin-4-yl}-piperidine-1-carboxylic acid tert-butyl ester

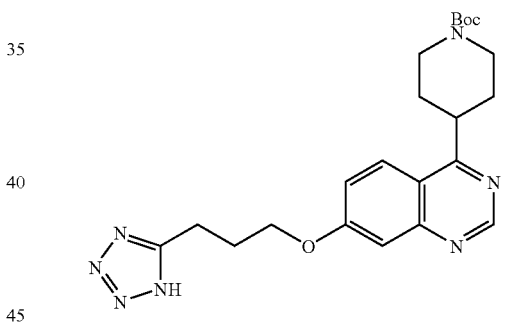

a. 4-[7-(3-Cyano-propoxy)-quinazolin-4-yl]-piperidine-1-carboxylic acid tert-butyl ester

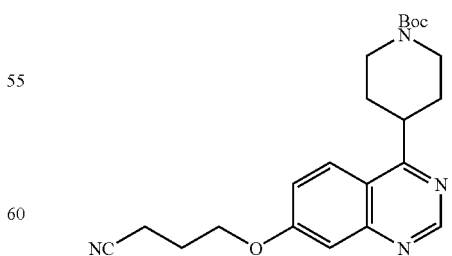

A mixture of 4-hydroxybutyronitrile (24.2 mg, 285 μmol) [*Organometallics* (1996), 15(4), 1236-41], KOtBu (34.8 mg, 311 μmol), and DME was stirred at rt, followed by the addition of 4-(7-Fluoro-quinazolin-4-yl)-piperidine-1-carboxylic acid tert-butyl ester (48.8 mg, 147 μmol) (prepared as described in Example 12b). The resulting homogeneous solution was stirred at rt for 2 hr, and was then directly loaded onto a 5 g Jones silica cartridge pre-equilibrated with 9:1 DCM/acetone, and eluted with 9:1→8:2 DCM/acetone to afford the title intermediate (24.5 mg, 42%) as a colorless oil. LC/MS (ESI) calcd mass 396.2, found 397.1 (MH)+.

b. 4-{7-[3-(1H-Tetrazol-5-yl)-propoxy]-quinazolin-4-yl}-piperidine-1-carboxylic acid tert-butyl ester

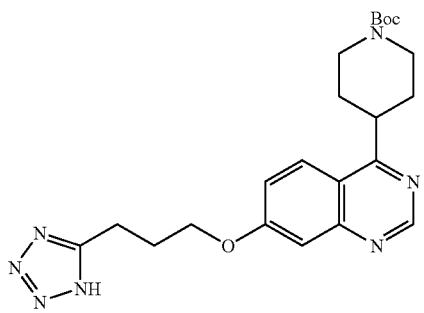

A mixture of 4-[7-(3-Cyano-propoxy)-quinazolin-4-yl]-piperidine-1-carboxylic acid tert-butyl ester (24.5 mg, 62 μmol), as prepared in the preceding step, NaN$_3$ (13.4 mg, 206 μmol), TEA.HCl (25.5 mg, 185 μmol), and toluene (100 μL) was tightly capped and stirred at 100° C. for 6.5 hr. The reaction was then allowed to cool to rt, partitioned with EtOAc (1 mL) and 0.1 M HCl (1 mL). The aqueous layer was then extracted with EtOAc (2×1 mL), the organic layers were combined, dried (Na$_2$SO$_4$), and concentrated. The residue was purified via flash silica chromatography (3:2 EtOAc/acetone) to yield the title intermediate as an off-white solid (12.2 mg, 44%). LC/MS (ESI) calcd mass 439.2, found 440.1 (MH)+.

EXAMPLE 90

4-{6-Fluoro-7-[3-(4-methyl-piperazin-1-yl)-propoxy]-quinazolin-4-yl}-piperidine-1-carboxylic acid tert-butyl ester

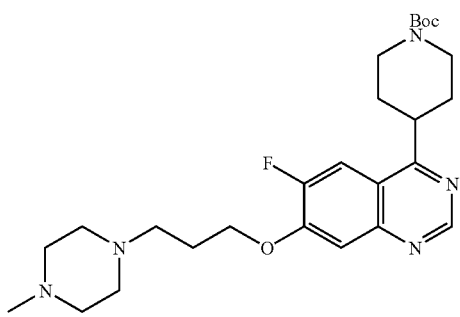

a. 4-Chloro-6,7-difluoro-quinazoline

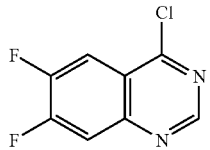

A mixture of 4,5-difluoroanthranilic acid (20.43 g, 118 mmol) and formamidine acetate (13.55 g, 130 mmol) in reagent EtOH was stirred at 120° C. (oil bath) for 3 hr. The reaction was briefly a homogeneous brown solution, and then became an opaque mixture. The reaction was allowed to cool to rt, and the resulting solid was filtered, washed with denatured EtOH (1×10 mL), and allowed to air dry. Powdering with a mortar and pestle provided 4-hydroxy-6,7-difluoro-quinazoline as a beige powder (16.9 g, 79%). 16.6 g of this material (91.1 mmol) was taken up in SOCl$_2$ (66 mL), DCE (66 mL), and DMF (7.05 mL, 91 mmol), and was stirred at 110° C. (oil bath) for 1 hr. The resulting homogeneous amber solution was then concentrated under rotary evaporation, and taken up in toluene (2×100 mL) with repeated rotary evaporation to provide the crude title compound as a beige solid. A portion of this material (8.4 g of 17.7 g total) was taken up in DCM (80 mL) and gently shaken with 2M trisodium citrate (1×40 mL) until a homogeneous clear organic layer resulted. This organic layer was immediately applied (without drying) directly onto a silica flash column (79 mm×6") pre-equilibrated with 1:1 hexanes/EtOAc. Trivial elution with 1:1 hexanes/EtOAc, followed by repeated rotary evaporation from toluene (2×50 mL) of the combined fractions afforded the title compound as a light yellow solid (6.79 g, 78%). $^1$H-NMR (400 MHz, CDCl$_3$) δ 9.05 (s, 1H), 8.05 (dd, 1H), 7.86 (dd, 1H).

b. 4-(6,7-Difluoro-quinazolin-4-yl)-piperidine-1,4-dicarboxylic acid 1-tert-butyl ester 4-methyl ester

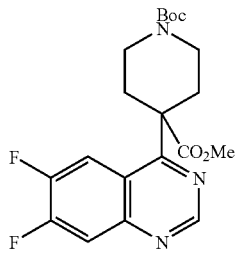

A solution of piperidine-1,4-dicarboxylic acid 1-tert-butyl ester 4-methyl ester (1.27 g, 5.23 mmol) in dry THF (2 mL) was added dropwise over 2 minutes with stirring to 1.01M LiHMDS/THF (5.75 mL, 5.81 mmol) at −78° C. under argon. After 5 min at −78° C., the cold bath was removed and the reaction was allowed to stir at "rt" for 30 min. A portion of this enolate solution (5.1 mL, 3 mmol enolate) was added dropwise over 2-3 min to a stirred homogeneous solution of 4-chloro-6,7-difluoroquinazoline (600 mg, 2.99 mmol) in dry THF (3 mL) at 0° C. under argon. The reaction was stirred for 30 min at 0° C., and was then quenched with 1M NaH$_2$PO$_4$ (50 mL) and extracted with EtOAc (1×50 mL). The organic layer was washed with 4M NaCl (1×50 mL), dried (Na$_2$SO$_4$), and concentrated. The residue was purified with silica flash chromatography (3:1 hexanes/EtOAc) to afford the title compound as a yellow oil (451 mg, 37%). LC/MS (ESI): calcd mass 407.2, found 408.2 (MH)⁺.

c. 4-(6,7-Difluoro-quinazolin-4-yl)-piperidine-1-carboxylic acid tert-butyl ester

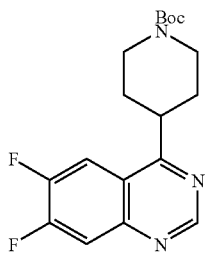

A mixture of 4-(6,7-Difluoro-quinazolin-4-yl)-piperidine-1,4-dicarboxylic acid 1-tert-butyl ester 4-methyl ester (451 mg, 1.11 mmol), as prepared in the previous step, LiCl (89 mg, 2.12 mmol), water (60 μL, 3.3 mmol), and DMSO (430 μL) was stirred at 150° C. for 7.5 hrs with a reflux condenser. The reaction was then allowed to cool to rt, shaken with 1M NaCl (5 mL), and extracted with DCM (1×3 mL) and 9:1 DCM/MeOH (1×3 mL). The organic layers were combined, dried (Na$_2$SO$_4$), and concentrated. The residue was purified by silica flash chromatography (3:1 hex/EtOAc→2:1 eluent) to provide the title compound (151.8 mg, 39%). ¹H-NMR (300 MHz, CDCl$_3$) δ 9.22 (s, 1H), 7.90 (dd, 1H), 7.81 (dd, 1H), 4.33 (br m, 2H), 3.50 (tt, 1H), 2.96 (brt, 2H), 2.11-1.82 (m, 4H), 1.49 (s, 9H). LC/MS (ESI): calcd mass 349.2, found 368.3 (MH.H$_2$O)⁺.

d. 4-{6-Fluoro-7-[3-(4-methyl-piperazin-1-yl)-propoxy]-quinazolin-4-yl}-piperidine-1-carboxylic acid tert-butyl ester

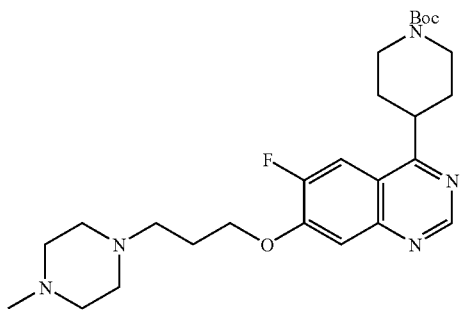

A solution of 1.19M KOtBu in THF (128 μL, 152 μmol) was added dropwise with stirring over 2.5 min to a 0° C. homogeneous solution of 4-(6,7-Difluoro-quinazolin-4-yl)-piperidine-1-carboxylic acid tert-butyl ester (38.1 mg, 109 μmol), as prepared in the previous step, and 3-(4-Methyl-piperazin-1-yl)-propan-1-ol (22.4 mg, 142 μmol) in THF (170 μL). The reaction was stirred at 0° C. for 1.5 hr, and was then partitioned with DCM (2 mL) and 1M NaCl (2 mL). The aq layer was back-extracted with DCM (1×2 mL), and the combined cloudy white organic layers were dried (Na$_2$SO$_4$) and concentrated. The residue was purified by silica flash chromatography (1:2 hex/EtOAc/3% DMEA eluent) to yield the title compound as an off-white foam (32.6 mg, 61%). NOe experiments support the assigned regioisomer. Select ¹H-NMR resonances and nOes (300 MHz, CDCl$_3$) δ 7.73 (d, J=11.4 Hz, 1H), 7.43 (d, J=8.1 Hz, 1H), 3.46 (tt, 1H). Irradiation of the diagnostic methine proton at δ 3.46 generates an nOe to the quinazoline C5 proton at δ 7.73, but not to the quinazoline C8 proton at δ 7.43. The C5 proton has a larger coupling constant than the C8 proton, indicating fluorine substitution at C6 of the quinazoline. LC/MS (ESI): calcd mass 487.3, found 488.3 (MH)⁺.

EXAMPLE 91

4-{6-Fluoro-7-[2-(2-oxo-pyrrolidin-1-yl)-ethoxy]-quinazolin-4-yl}-piperidine-1-carboxylic acid tert-butyl ester

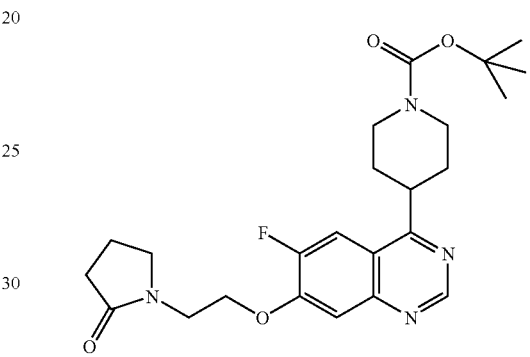

Prepared as for Example 90d using 1-(2-Hydroxy-ethyl)-pyrrolidin-2-one.

EXAMPLE 92

4-{6-Methoxy-7-[3-(4-methyl-piperazin-1-yl)-propoxy]-quinazolin-4-yl}-piperidine-1-carboxylic acid tert-butyl ester

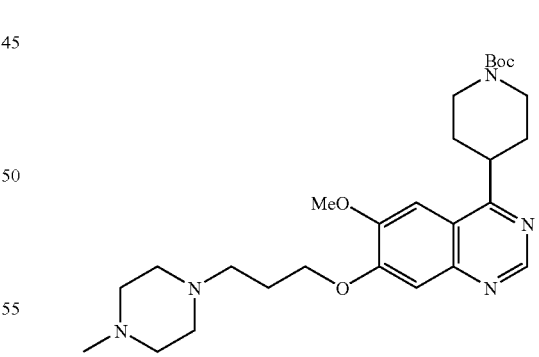

A mixture of 4-{6-Fluoro-7-[3-(4-methyl-piperazin-1-yl)-propoxy]-quinazolin-4-yl}-piperidine-1-carboxylic acid tert-butyl ester (32.6 mg, 66.9 μmol), as prepared in Example 90d, DMSO (50 μL), and 0.31M KOMe/MeOH (270 μL, 83.9 μmol KOMe in 6.4 mmol MeOH) was stirred at 100° C. for 9 hr, and then 110° C. for 2 hr. The resulting pale yellow homogeneous solution was allowed to cool to rt, diluted with DCM (2 mL), and washed with 4M NaCl (1×2 mL). The aq layer was back-extracted with DCM (1×2 mL), and the combined organic layers were dried (Na$_2$SO$_4$) and concentrated. Purification of the residue by silica flash chromatography (1:2 hex/EtOAc→1:2 hex/EtOAc/3% DMEA→9:1 EtOAc/acetone/3% DMEA eluent) afforded the title compound (18.4 mg, 55%). NOe experiments support the assigned regioisomer. Select $^1$H-NMR resonances and nOes (300 MHz, CDCl$_3$) δ 7.34 (s, 1H), 7.24 (s, 1H), 4.04 (s, 3H), 3.51 (m, 1H). Irradiation of the diagnostic methine proton at δ 3.51 generates an nOe to the quinazoline C5 proton at δ 7.24, but not to the quinazoline C8 proton at δ 7.34. Irradiation of the methoxy protons at δ 4.04 generates an nOe to the C5 proton at δ 7.24, but not to the C8 proton at δ 7.34. This indicates methoxy substitution at C6 of the quinazoline. LC/MS (ESI): calcd mass 499.3, found 500.4 (MH)$^+$.

EXAMPLE 93

4-{6-Methoxy-7-[2-(2-oxo-pyrrolidin-1-yl)-ethoxy]-quinazolin-4-yl}-piperidine-1-carboxylic acid tert-butyl ester

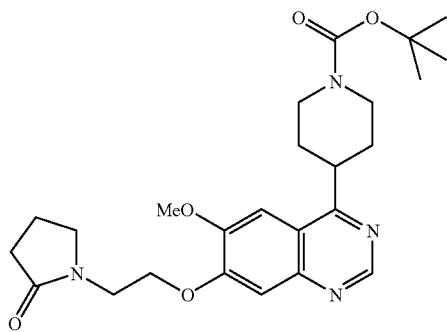

Prepared as for Example 92 using 1-(2-Hydroxy-ethyl)-pyrrolidin-2-one instead of 3-(4-methyl-piperazin-1-yl)-propan-1-ol. LC/MS (ESI): calcd mass 470.3, found 471.3 (MH)$^+$

EXAMPLE 94

4-(6-Fluoro-7-morpholin-4-yl-quinazolin-4-yl)-piperidine-1-carboxylic acid tert-butyl ester

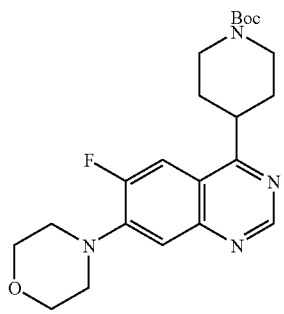

A solution of 4-(6,7-Difluoro-quinazolin-4-yl)-piperidine-1-carboxylic acid tert-butyl ester (37.8 mg, 108 μmol) (preparation in Example 90c) and morpholine (19.8 μL, 227 μmol) in THF (100 μL) and DMSO (50 μL) was heated at 100° C. for 1 hr. The crude reaction was loaded onto a flash silica cartridge (1:1 hexanes/EtOAc eluent) to provide the title compound (40.2 mg, 89%). NOe experiments support the assigned regioisomer. Select $^1$H-NMR resonances and nOes (300 MHz, CDCl$_3$) δ 7.68 (d, J=13.7 Hz, 1H), 7.37 (d, J=8.4 Hz, 1H), 3.45 (tt, 1H), 3.31 (m, 4H). Irradiation of the diagnostic methine proton at δ 3.45 generates an nOe to the quinazoline C5 proton at δ 7.68, but not to the quinazoline C8 proton at δ 7.37. The C5 proton has a larger coupling constant than the C8 proton, indicating fluorine substitution at C6 of the quinazoline. Furthermore, irradiation of the C8 proton at δ 7.37 generates an nOe only to the morpholine C3 protons at δ 3.31, while irradiation of the C5 proton generates an nOe only to the methine proton at δ 3.45. These data indicate morpholine substitution at the quinazoline C7 carbon. LC/MS (ESI): calcd mass 416.2, found 417.3 (MH)$^+$.

EXAMPLE 95

4-(6-Methoxy-7-morpholin-4-yl-quinazolin-4-yl)-piperidine-1-carboxylic acid tert-butyl ester

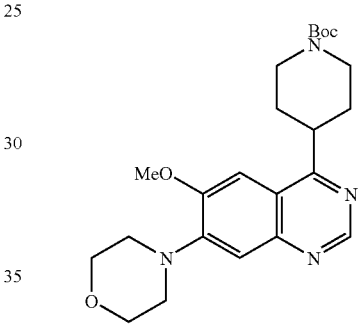

A mixture of 4-(6-Fluoro-7-morpholin-4-yl-quinazolin-4-yl)-piperidine-1-carboxylic acid tert-butyl ester (28.9 mg, 69.5 μmol), as prepared in Example 94a, DMSO (50 μL), and 10M KOMe/MeOH (140 μL, 140 μmol) was stirred in a sealed vial at 100° C. (aluminum block) for 13 hr. The crude reaction was then diluted with toluene and directly loaded onto a silica flash column (1:2 hexanes/EtOAc eluent) to provide the title compound (20.0 mg, 67%). NOe experiments support the assigned regioisomer. Select $^1$H-NMR resonances and nOes (300 MHz, CDCl$_3$) δ 7.36 (s, 1H), 7.25 (s, 1H), 4.05 (s, 3H), 3.51 (m, 1H). Irradiation of the diagnostic methine proton at δ 3.51 generates an nOe to the quinazoline C5 proton at δ 7.25, but not to the quinazoline C8 proton at δ 7.36. Irradiation of the methoxy protons at δ 4.05 generates an nOe to the C5 proton at δ 7.25, but not to the C8 proton at δ 7.36. This indicates methoxy substitution at C6 of the quinazoline. LC/MS (ESI): calcd mass 428.2, found 429.3 (MH)$^+$.

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

We claim:
1. A compound of Formula C:

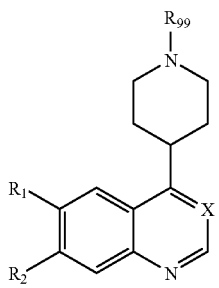

Formula C and N-oxides and stereochemical isomers thereof, wherein:
X is N or CH;
$R_1$ and $R_2$ are independently selected from:

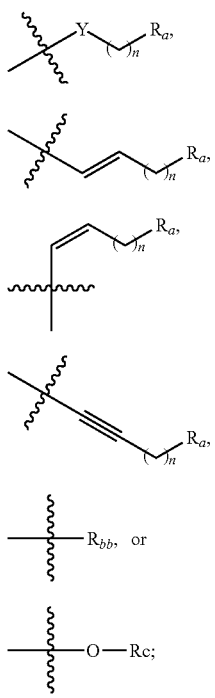

(a-1)

(a-2)

(a-3)

(a-4)

(a-5)

(a-6)

wherein n is 1, 2, 3 or 4;
Y is a direct bond, O, S, NH, or N(alkyl);
$R_a$ is alkoxy, phenoxy, heteroaryl optionally substituted with $R_5$, hydroxyl, alkylamino, dialkylamino, oxazolidinonyl optionally substituted with $R_5$, pyrrolidinonyl optionally substituted with $R_5$, piperidinonyl optionally substituted with $R_5$, piperazinyl-2-one optionally substituted with $R_5$, cyclic heterodionyl optionally substituted with $R_5$, heterocyclyl optionally substituted with $R_5$, squaryl optionally substituted with $R_5$, —COOR$_y$, —CONR$_w$R$_x$, —N(R$_y$)CON(R$_w$)(R$_x$), —N(R$_w$)C(O)OR$_x$, —N(R$_w$)COR$_y$, —SR$_y$, —SOR$_y$, —SO$_2$R$_y$, —NR$_w$SO$_2$R$_y$, —NR$_w$SO$_2$R$_x$, —SO$_3$R$_y$, —OSO$_2$NR$_w$R$_x$, or —SO$_2$NR$_w$R$_x$;
$R_w$ and $R_x$ are independently selected from: hydrogen, alkyl, alkenyl, aralkyl, or heteroaralkyl, or $R_w$ and $R_x$ may optionally be taken together to form a 5 to 7 membered ring, optionally containing a heteromoiety selected from O, NH, N(alkyl), SO, SO$_2$, or S;
$R_y$ is selected from: hydrogen, alkyl, alkenyl, cycloalkyl, phenyl, aralkyl, heteroaralkyl, or heteroaryl;
$R_5$ is one, two, or three substituents independently selected from: halogen, cyano, trifluoromethyl, amino, hydroxyl, heteroaryl, alkoxy, —C(O)alkyl, —SO$_2$alkyl, —C(O)NH(alkyl), —C(O)N(alkyl)$_2$, —C(O)C$_{(1-4)}$alkyl-N(alkyl)$_2$, alkyl, —C$_{(1-4)}$alkyl-OH, —C$_{(1-4)}$alkyl-OCH$_3$, —C(O)C$_{(1-4)}$alkyl-OH, —C(O)C$_{(1-4)}$alkyl-OCH$_3$, a protecting group which is fluoren-9-yl-methyl-oxy carbonyl, dialkylamino, or alkylamino; provided that the same $R_5$ substituent is not present more than once, unless said $R_5$ substituent is halogen, hydroxyl, alkoxy, or alkyl;
$R_{bb}$ is hydrogen provided that both $R_1$ and $R_2$ are not hydrogen; or $R_{bb}$ is alkoxy provided that both $R_1$ and $R_2$ are not alkoxy; or $R_{bb}$ is selected from the group consisting of: halogen, dialkylamino, phenyl optionally substituted with $R_6$, heteroaryl optionally substituted with $R_6$, piperazinyl-2-one optionally substituted with $R_6$, imidazolidinyl-2-one optionally substituted with $R_6$, oxazolidinyl-2-one optionally substituted with $R_6$, or heterocyclyl optionally substituted with $R_6$;
$R_6$ is one, two, or three substituents independently selected from: halogen, cyano, trifluoromethyl, amino, hydroxyl, heteroaryl, alkoxy, —C(O)alkyl, —SO$_2$alkyl, —C(O)NH(alkyl), —C(O)N(alkyl)$_2$, —C(O)C$_{(1-4)}$alkyl-N(alkyl)$_2$, alkyl, —C$_{(1-4)}$alkyl-OH, —C$_{(1-4)}$alkyl-OCH$_3$, —C(O)C$_{(1-4)}$alkyl-OH, —C(O)C$_{(1-4)}$alkyl-OCH$_3$, dialkylamino, or alkylamino; provided that the same $R_6$ substituent is not present more than once, unless said $R_6$ substituent is halogen, hydroxyl, alkoxy, or alkyl;
$R_c$ is heterocyclyl optionally substituted with $R_7$, or heteroaryl; and
$R_7$ is one, two, or three substituents independently selected from: halogen, cyano, trifluoromethyl, amino, hydroxyl, heteroaryl, alkoxy, —C(O)alkyl, —SO$_2$alkyl, —C(O)NH(alkyl), —C(O)N(alkyl)$_2$, —C(O)C$_{(1-4)}$alkyl-N(alkyl)$_2$, alkyl, —C$_{(1-4)}$alkyl-OH, —C$_{(1-4)}$alkyl-OCH$_3$, —C(O)C$_{(1-4)}$alkyl-OH, —C(O)C$_{(1-4)}$alkyl-OCH$_3$, dialkylamino, or alkylamino; provided that the same $R_7$ substituent is not present more than once, unless said $R_7$ substituent is halogen, hydroxyl, alkoxy, or alkyl; and
$R_{99}$ is hydrogen, —CO$_2$-tert-butyl, —CO$_2$CH$_2$Ph, —CO$_2$CH$_2$-9H-fluoren-9-yl, —SO$_2$Ph, or —SO$_2$toluyl).

2. A compound of claim 1, wherein:
$R_w$ and $R_x$ are independently selected from: hydrogen, alkyl, alkenyl, aralkyl, or heteroaralkyl, or $R_w$ and $R_x$ may optionally be taken together to form a ring selected from the group consisting of:

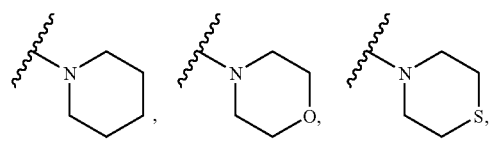

-continued

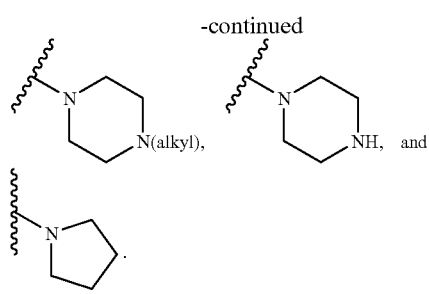

3. A compound of claim 1, wherein:

$R_{bb}$ is hydrogen provided that both $R_1$ and $R_2$ are not hydrogen; or $R_{bb}$ is alkoxy provided that both $R_1$ and $R_2$ are not alkoxy; or $R_{bb}$ is selected from the group consisting of: halogen, dialkylamino, phenyl, heteroaryl, piperazinyl-2-one optionally substituted with $R_6$, imidazolidinyl-2-one optionally substituted with $R_6$, oxazolidinyl-2-one optionally substituted with $R_6$, or heterocyclyl optionally substituted with $R_6$.

4. A compound of claim 3, wherein:

Y is a direct bond, O, or NH;

$R_a$ is alkoxy, heteroaryl optionally substituted with $R_5$, hydroxyl, alkylamino, dialkylamino, oxazolidinonyl optionally substituted with $R_5$, pyrrolidinonyl optionally substituted with $R_5$, piperidinonyl optionally substituted with $R_5$, piperazinyl-2-one optionally substituted with $R_5$, cyclic heterodionyl optionally substituted with $R_5$, heterocyclyl optionally substituted with $R_5$, squaryl optionally substituted with $R_5$, —CONR$_w$R$_x$, —N(R$_y$)CON(R$_w$)(R$_x$), —N(R$_w$)C(O)OR$_x$, —N(R$_w$)COR$_y$, —SR$_y$, —SOR$_y$, —SO$_2$R$_y$, or —NR$_w$SO$_2$R$_y$; and $R_{bb}$ is hydrogen provided that both $R_1$ and $R_2$ are not hydrogen; or $R_{bb}$ is alkoxy provided that both $R_1$ and $R_2$ are not alkoxy; or $R_{bb}$ is selected from the group consisting of: halogen, piperazinyl-2-one optionally substituted with $R_6$, imidazolidinyl-2-one optionally substituted with $R_6$, oxazolidinyl-2-one optionally substituted with $R_6$, or heterocyclyl optionally substituted with $R_6$.

5. A compound of claim 4, wherein:

$R_1$ and $R_2$ are independently selected from:

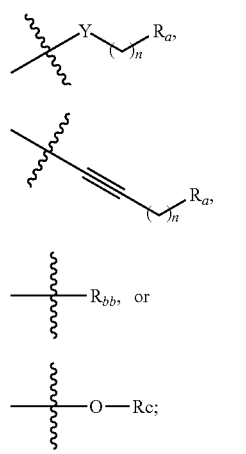

Y is O or NH;

$R_a$ is alkoxy, heteroaryl optionally substituted with $R_5$, hydroxyl, alkylamino, dialkylamino, oxazolidinonyl optionally substituted with $R_5$, pyrrolidinonyl optionally substituted with $R_5$, piperidinonyl optionally substituted with $R_5$, piperazinyl-2-one optionally substituted with $R_5$, heterocyclyl optionally substituted with $R_5$, squaryl optionally substituted with $R_5$, —CONR$_w$R$_x$, —N(R$_y$)CON(R$_w$)(R$_x$), —N(R$_w$)C(O)OR$_x$, —N(R$_w$)COR$_y$, —SO$_2$R$_y$, or —NR$_w$SO$_2$R$_y$;

$R_5$ is one or two substituents selected from: —C(O)alkyl, —SO$_2$alkyl, —C(O)NH(alkyl), —C(O)N(alkyl)$_2$, —C(O)C$_{(1-4)}$alkyl-N(alkyl)$_2$, alkyl, —C$_{(1-4)}$alkyl-OH, —C$_{(1-4)}$alkyl-OCH$_3$, —C(O)C$_{(1-4)}$alkyl-OH, fluoren-9-yl-methyl-oxy carbonyl, or —C(O)C$_{(1-4)}$alkyl-OCH$_3$; provided that the same $R_5$ substituent is not present more than once, unless said $R_5$ substituent is alkyl;

$R_6$ is one or two substituents independently selected from: halogen, hydroxyl, heteroaryl, alkoxy, —C(O)alkyl, —SO$_2$alkyl, —C(O)NH(alkyl), —C(O)N(alkyl)$_2$, —C(O)C$_{(1-4)}$alkyl-N(alkyl)$_2$, alkyl, —C$_{(1-4)}$alkyl-OH, —C$_{(1-4)}$alkyl-OCH$_3$, —C(O)C$_{(1-4)}$alkyl-OH, or —C(O)C$_{(1-4)}$alkyl-OCH$_3$; provided that the same $R_6$ substituent is not present more than once, unless said $R_6$ substituent is halogen, hydroxyl, or alkyl;

$R_c$ is heterocyclyl optionally substituted with $R_7$; and $R_7$ is one substituent selected from: hydroxyl, —C(O)alkyl, —SO$_2$alkyl, alkyl, or —C(O)N(alkyl)$_2$.

6. A compound of claim 5, wherein:

$R_1$ and $R_2$ are independently selected from:

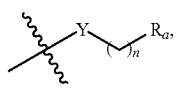

(a-1)

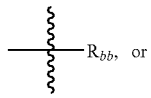

(a-5)

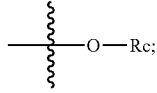

(a-6)

Y is O;

$R_a$ is alkoxy, heteroaryl optionally substituted with $R_5$, hydroxyl, alkylamino, dialkylamino, oxazolidinonyl optionally substituted with $R_5$, pyrrolidinonyl optionally substituted with $R_5$, piperazinyl-2-one optionally substituted with $R_5$, heterocyclyl optionally substituted with $R_5$, —CONR$_w$R$_x$, —N(R$_y$)CON(R$_w$)(R$_x$), —SO$_2$R$_y$, or —NR$_w$SO$_2$R$_y$;

$R_5$ is one substituent selected from: —C(O)alkyl, —SO$_2$alkyl, —C(O)NH(alkyl), —C(O)N(alkyl)$_2$, —C(O)C$_{1-4}$alkyl-N(alkyl)$_2$, alkyl, —C$_{(1-4)}$alkyl-OH, —C$_{(1-4)}$alkyl-OCH$_3$, —C(O)C$_{(1-4)}$alkyl-OH, fluoren-9-yl-methyl-oxy carbonyl, or —C(O)C$_{(1-4)}$alkyl-OCH$_3$;

$R_6$ is one substituent selected from: hydroxyl, alkoxy, —C(O)alkyl, —SO$_2$alkyl, —C(O)NH(alkyl), —C(O)N(alkyl)$_2$, —C(O)C$_{1-4}$alkyl-N(alkyl)$_2$, alkyl, —C$_{(1-4)}$alkyl-OH, —C$_{(1-4)}$alkyl-OCH$_3$, —C(O)C$_{(1-4)}$alkyl-OH, or —C(O)C$_{(1-4)}$alkyl-OCH$_3$; and
$R_7$ is one substituent selected from —C(O)alkyl, —SO$_2$alkyl, or alkyl.
7. A compound selected from the group consisting of:
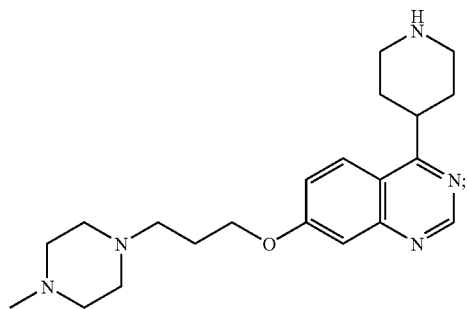
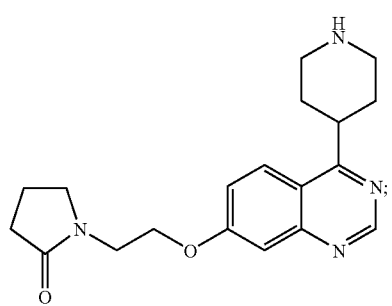
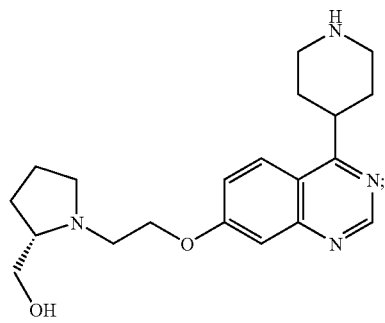
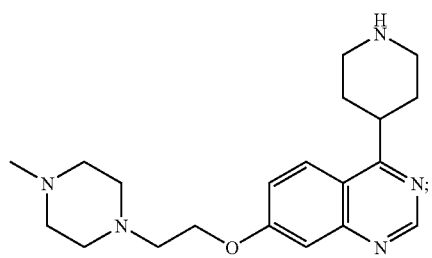
-continued
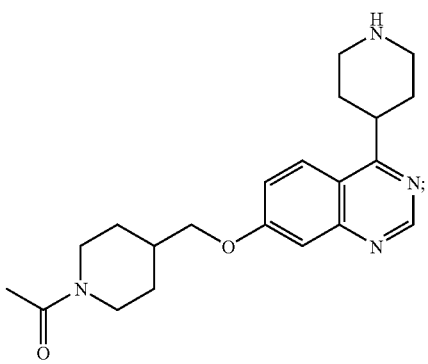
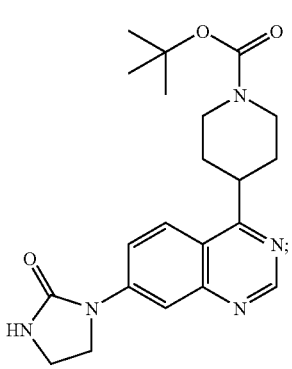
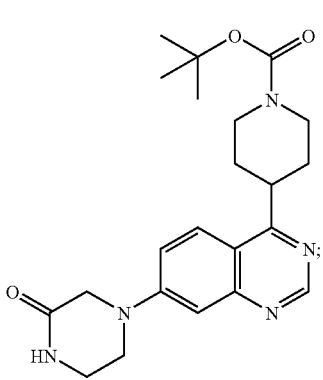
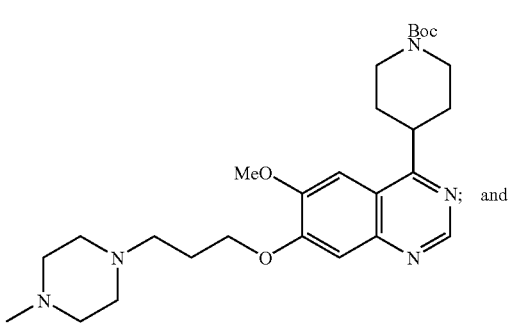

-continued

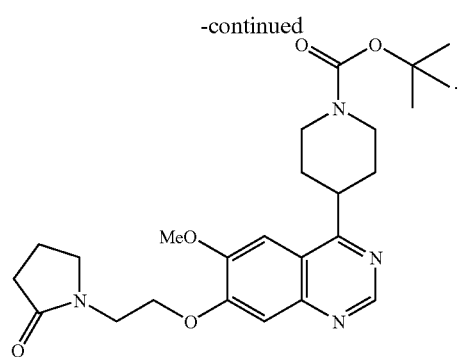

8. A compound selected from the group consisting of:

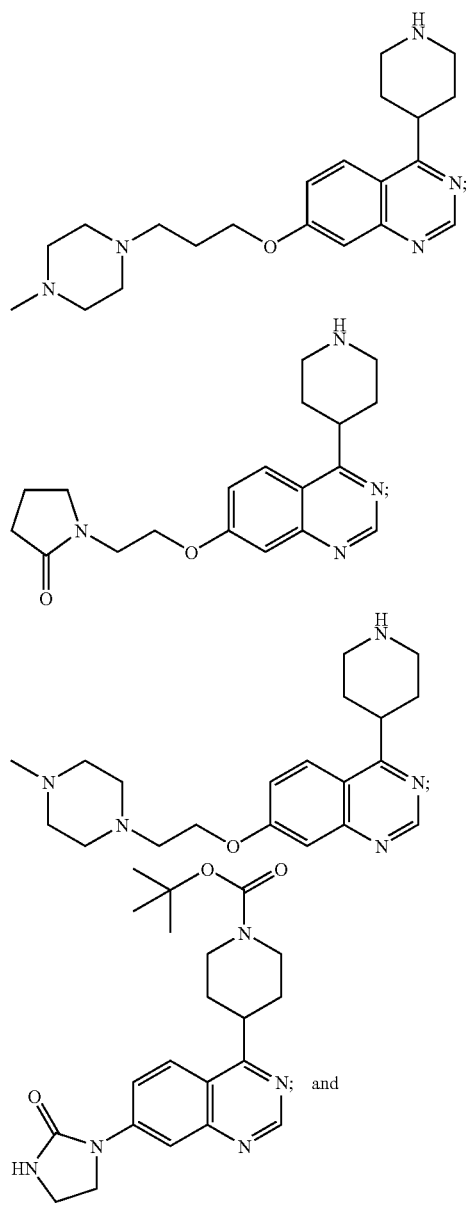

-continued

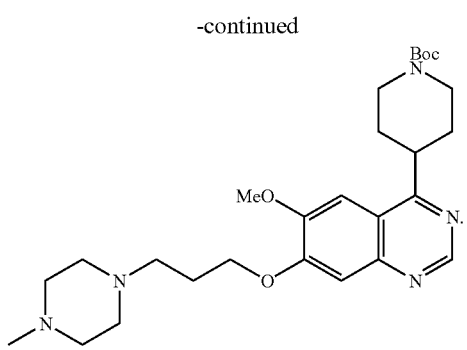

9. A compound that is:

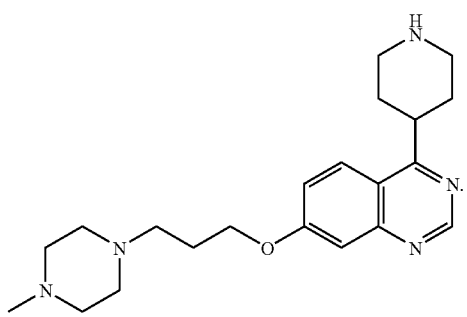

10. A compound of claim 2, wherein:

$R_{bb}$ is hydrogen provided that both $R_1$ and $R_2$ are not hydrogen; or $R_{bb}$ is alkoxy provided that both $R_1$ and $R_2$ are not alkoxy; or $R_{bb}$ is selected from the group consisting of: halogen, dialkylamino, phenyl, heteroaryl, piperazinyl-2-one optionally substituted with $R_6$, imidazolidinyl-2-one optionally substituted with $R_6$, oxazolidinyl-2-one optionally substituted with $R_6$, or heterocyclyl optionally substituted with $R_6$.

11. A compound of claim 1, wherein:

$R_{bb}$ is hydrogen provided that both $R_1$ and $R_2$ are not hydrogen; or $R_{bb}$ is alkoxy provided that both $R_1$ and $R_2$ are not alkoxy; or $R_{bb}$ is selected from the group consisting of: halogen, dialkylamino, phenyl, heteroaryl, piperazinyl-2-one optionally substituted with $R_6$, imidazolidinyl-2-one optionally substituted with $R_6$, oxazolidinyl-2-one optionally substituted with $R_6$, or heterocyclyl optionally substituted with $R_6$.

12. A compound of claim 2, wherein $R_{99}$ is hydrogen, —$CO_2$-tert-butyl, —$CO_2CH_2Ph$, —$CO_2CH_2$-9H-fluoren-9-yl, —$SO_2Ph$, or —$SO_2$toluyl).

* * * * *